United States Patent
Shapiro et al.

(10) Patent No.: US 6,266,569 B1
(45) Date of Patent: Jul. 24, 2001

(54) METHOD AND SYSTEM OF COMPUTING SIMILAR TO A TURING MACHINE

(75) Inventors: Ehud Shapiro, Nataf (IE); Kanchana S. G. Karunaratne, San Diego, CA (US)

(73) Assignee: Zephyrien International N.V., Curacao (AN)

( * ) Notice: Subject to any disclaimer, the term of this patent is extended or adjusted under 35 U.S.C. 154(b) by 0 days.

(21) Appl. No.: 09/184,178

(22) Filed: Nov. 2, 1998

Related U.S. Application Data

(60) Provisional application No. 60/098,502, filed on Aug. 31, 1998.

(51) Int. Cl.⁷ .................................................. G05B 15/00

(52) U.S. Cl. ..................................................... 700/1

(58) Field of Search ..................................... 435/4

(56) References Cited

U.S. PATENT DOCUMENTS

| | | |
|---|---|---|
| 5,270,163 | 12/1993 | Gold et al. . |
| 5,439,829 | 8/1995 | Anderson et al. . |
| 5,766,855 | 6/1998 | Buchardt et al. . |
| 5,804,373 * | 9/1998 | Schweitzer et al. ............. 435/6 |
| 5,843,661 * | 12/1998 | Rothemund ..................... 435/6 |

OTHER PUBLICATIONS

Howard, Computing with DNA, Computer World [online], [retrieved on Aug. 24, 2000]. Retrieved from the internet <http://www.cs.man.ac.uk/aig/staff/toby/writing/PCW/cna.htm>, 2000.*

Y. Watanabe et al, "A unique enzyme from Saccharothrix sp. Catalyzing D–amino acid transfer", Biochim Biophys Acta 1337, 1997, p.p 40–46.

K.E. Drexler, "An Approach to the Development of General Capabilities for Molecular Manipulation" Proc. Natl. Acad. Sci. USA 78, No. 9, Sep. 1981 p.p. 5275–5278.

J. Liu et al, "Fullerene Pipes", Science vol.280, May 1998 p.p. 1253–1256.

J.M Michelsen et al, "Assembler Construction by Proximal Probe", The Fifth Foresight Conference on Molecular Nanotechnology, Nov. 1997 Palo–Alto California.

H. Nakajima et al, "Dipeptide Synthesis Catalyzed by aminoacyl–tRNA synthetases from *Bacillus stearothermophilus*", Int. J. Protein Res. 28, 1986, p.p. 179–185.

R.E. Offord, "Chemical Approaches to Protein Engineering", Protein Design and the Development of New Therapeutics and Vaccines, Plenum NY 1990, p.p. 253–282.

(List continued on next page.)

*Primary Examiner*—John S. Brusca
(74) *Attorney, Agent, or Firm*—Irah H. Donner; Hale and Dorr LLP

(57) ABSTRACT

A Brownian Turing machine includes a multiplicity of alphabet elements, multiple state transition elements and a single enzymatic unit. The alphabet elements define a plurality of different types of information. The state transition elements define how the machine can change state. The enzymatic unit receives dimers one at a time, wherein each dimer is comprised of one state transition element combined to one alphabet element. The enzymatic unit determines if a dimer is an allowable next dimer and, if it is, connects the state transition element of the allowed dimer to a history tape of the history of at least one change of state. The enzymatic unit also modifies an alphabet tape, comprising at least two alphabet elements connected together, with the alphabet element of the allowed dimer in accordance with the state transition defined by the state transition element of the allowed dimer. The alphabet elements, state transition elements and enzymatic unit can be mechanical, chemical or biological elements.

8 Claims, 78 Drawing Sheets

OTHER PUBLICATIONS

H.F. Gaertner et al, "Site–Specific Religation of G–CSF Fragments through a Thioether Bond", Bioconjugate Chemistry, vol. 5, 1994, p.p. 333–338.

J.E. Hale, "Irreversible, Oriented Immobilization of Antibodies to Cobalt–Iminodiacetate Resin for USA as Immunoaffinity Media", Analytical Biochemistry, vol. 231, 1995, p.p. 46–49.

P.E. Nielsen et al, "Sequence–Selective Recognition of DNA by Strand Displacement with a Thymine–Substituted Polyamide", Science 254, 1991, p.p. 1497–1500.

S.F. Parmley et al, "Antibody–selectable filamentous fd phage vectors: affinity purification of target genes", Gene 73, 1988, p.p. 305–318.

P. Soumillion et al, "Phage Display of Enzymes and In Vitro Selection for Catalytic Activity" Appl. Biochem Biotechnol 47, 1994, p.p. 175–189.

Q. Ouyang et al, "DNA Solution of the Maximal Clique Problem", Science vol. 278, Oct. 1997, p.p. 446–449.

* cited by examiner

METHOD AND SYSTEM OF COMPUTING SIMILAR TO A TURING MACHINE

This application claims the benefit of U.S. Provisional Application No. 60/098,502, filed Aug. 31, 1998.

FIELD OF THE INVENTION

The present invention relates generally to computational devices based on Brownian motion of components, and miniaturization and molecular implementation of such devices.

BACKGROUND OF THE INVENTION

Alan Turing conceived the Turing machine in the 1930's as a basic and fundamental abstract computation device, to be used as an instrument for studying the mathematical concept of computation and computability.

A Turing machine 10, shown in FIG. 1, consists of an infinite storage tape 12 divided into tape cells 14, each cell 14 is capable of storing a single symbol, and a read/write head 16 connecting the tape 12 to a finite control 11. The machine 10 operates according to a control program, consisting of a finite number of state-transition rules, which are quintuples of the form <S,A,S',A',Dir>. Such a rule is interpreted as follows: If the finite control 11 is in state S, and the tape cell 14 of the read/write head 16 contains the symbol A, then change the control state to S', replace the symbol A by A', and move the read/write head 16 one cell 14 in direction Dir (Dir is either "left" or "right"). The Turing machine 10 begins its operation with a finite input written on the otherwise blank tape 12, the read/write head 16 located on the left-most non-blank symbol, and the control in a designated initial state. The computation progresses according to the control program, and terminates when no State-transition rule applies. The content of the non-blank part of tape 12 upon termination is considered the output of the computation.

During the 1930's other mathematical models of computation were developed, including the Lambda Calculus by Alonzo Church and the Primitive Recursive by Kurt Goedel. Following proofs that all these models are equivalent in their computational power, "Church's Thesis" was formulated, stating that all conceivable computational models, past and future, will turn out to be computationally equivalent to each other and in particular to the Turing machine.

While mathematically as powerful as any other computational model, the Turing machine was never implemented as a practical computation device. Turing envisioned his machine being operated by a human being, called "computer" that follows the rules of the control program and uses markers, pencil and an eraser to implement the read/write head 16.

In the 1940's, von Neumann and colleagues conceived the stored-program electronic computer, on which all modern computers are based.

In the 1970's, Charles Bennett performed a theoretical investigation of physical computation devices based on the Turing machine model. Bennett was motivated by the observation that the standard electronic computers are inherently energy-inefficient since their basic "store to memory" operation irreversibly erases the content of the memory location. Bennett believed that due to thermodynamic considerations computation devices that proceed in a reversible way would be more efficient, and he proposed two conceptual implementations of the Turing machine model that are reversible. One of these conceptual implementations, which he called "Brownian computer" since its operation was based on the Brownian motion of molecules, is a precursor to our invention. In Bennett's Brownian computer, named "hypothetical enzymatic Turing machine", the tape is a macromolecule consisting of a structural backbone bearing tape symbols and a head marker, and each quintuple of the control program is realized by a specific enzyme that effects the transition by removing and adding a tape symbol, and moving the location of the head marker. [Reference: Charles, H. Bennett, The Thermodynamics of Computation—A Review, International Journal of Theoretical Physics, Vol. 21, No. 12, 1982, pp.905–940].

More recently, interest in molecular computation devices resumed following the work of Adelman [Leonard M. Adelman, Molecular computation of solutions to combinatorial problems, Science, 266:1021–1024, 1994] in 1994, who showed how DNA segments combined with DNA related enzymes can be used to effect computations. Adelman's method was based on creating a test-tube solution consisting of DNA segments and performing "biological steps", effected by a human or a robot, which include adding certain enzymes to the solution, dividing the solution into several tubes, and/or changing the temperature of the solution. At the end of these steps the result of the computation is extracted via standard biological tools. Following that paper numerous proposals were made on how to implement a DNA-based Turing machine using DNA and related enzymes [Most of this work was reported in the four Proceedings of the Meetings on DNA Based Computers, DIMACS, 1995, 1996, 1997, 1998, and are reviewed in Eric Winfree's Ph.D. Thesis, Algorithmic Self-Assembly of DNA, Caltech, May, 1998]. These proposals fall into two broad classes: one class requires each step of the computation to be effected by a "biological step" as in Adelman's method. The second class [Erik Winfree, Simulations of Computing by Self-Assembly, Preliminary Proceedings of the Fourth International Meeting on DNA Based Computers, DIAMACS, Jun. 15–19, 1998, University of Pennsylvania, edited by Lila Kari, Harvey Rubin and David Harlan Wood, pages 213–239, and references thereto] creates a set of molecules that "self-assemble" in a way that effects a computation. Our invention belongs to that class.

SUMMARY OF THE INVENTION

An object of the present invention is to provide a mechanical working model of simple computation device similar to the Turing Machine. It can be seen that this extrapolates into molecular type implementations.

The technology of the Polymerase Chain Reaction (hereafter referred to as PCR) is similar in concept to this invention, however, whereas PCR is limited to the duplication of DNA, the present invention can be shown to perform useful computational output that can be executed in the form of a program. As any modern day computer can be shown to be reduced to a Turing machine in concept, thus any solvable problem could be solved by the Turing machine.

Thus, the invention can be seen as both a description of a computation device that can be readily operated by a human, or a robot, as envisioned by Alan Turing, as well as a specification for a molecular computation device, which can be driven by Brownian motion, as envisioned by Charles Bennet. The invention constitutes a specification for such a molecular computation device in that it describes the properties of the monomers as well as the enzyme components required by any molecular embodiment of the device.

The applications of such a molecular computation device are as an alternative to the existing computers, and more importantly, the integration of computational steps in sequences of biochemical reactions with therapeutic and/or biochemical purposes.

For convenience of implementation, our invention realizes a variant of the Turing machine in which the read/write head is located between cells, rather than on a cell. In a "move left" transition (Dir="left") the head reads the content of the cell to the left, writes on it, and moves one cell to the left. In a "move right" transition the symmetric description applies.

The invention is a Turing machine based on Brownian motion and consisting of three subsystems: an information storage tape, a history tape and an enzyme. The information storage tape is a polymer consisting of alphabet monomers that represent the content of the machine's tape and one state-transition monomer that represents the location of the machine's read/write head as well as its state. The history tape is a polymer of tstate-transition monomers used in the computation, to which are attached alphabet monomers which were displaced ("deleted") during the computation. The last monomer in the history tape is the state-transition monomer in the information storage tape. The "active site" of the computation is the state-transition monomer that is at the junction of the information storage tape and the history tape. The active site is enclosed by an enzyme that enables the computation to progress with valid transitions only.

For its operation the machine requires a potentially unlimited supply of each of the alphabet monomers and the state-transition monomers.

State-transition monomers represent potential transitions of the Turing machine, which include the current state and current tape symbol (the tape symbol adjacent to the state-transition monomer in the direction of movement), next state, next tape symbol and direction of movement. To effect a transition, a state-transition monomer forms a dimer with the alphabet monomer that represents the symbol to be written during the transition.

The enzyme allows such dimers to approach the active site, but only dimers that match the current state and current tape symbol can effect a transition. In a transition the current state-transition monomer and the current alphabet monomer are displaced from the information storage tape, and are replaced by the incoming dimer. In the process the displaced state-transition monomer, to which the displaced alphabet monomer is attached, continues to be part of the history tape, and the incoming state-transition monomer becomes the new terminal of the history tape.

The computation ends when the machine reaches a terminal state. The content of the information storage tape upon termination can be viewed as the output of the computation.

A simple extension to the Turing machine allows the machine to "erase" the information storage tape to the left or to the right of the read/write head in one transition, effectively discharging the left or right segment of the information storage polymer into the environment. Hence the machine can effectively create any desired polymer of alphabet monomers, in any number of copies, in the course of the computation. A molecular implementation of the Turing machine may use biologically significant monomers (e.g. nucleic acids or amino acids) as alphabet monomers. An ensemble of such machines might be used as a factory for producing biologically significant polymers.

Furthermore, since the machine can perform arbitrary computations in the course of producing such polymers, it can be "programmed" to do so only under a certain schedule, or only when certain external conditions arise, as described in the next section. The ability has clear pharmaceutical applications.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 2:
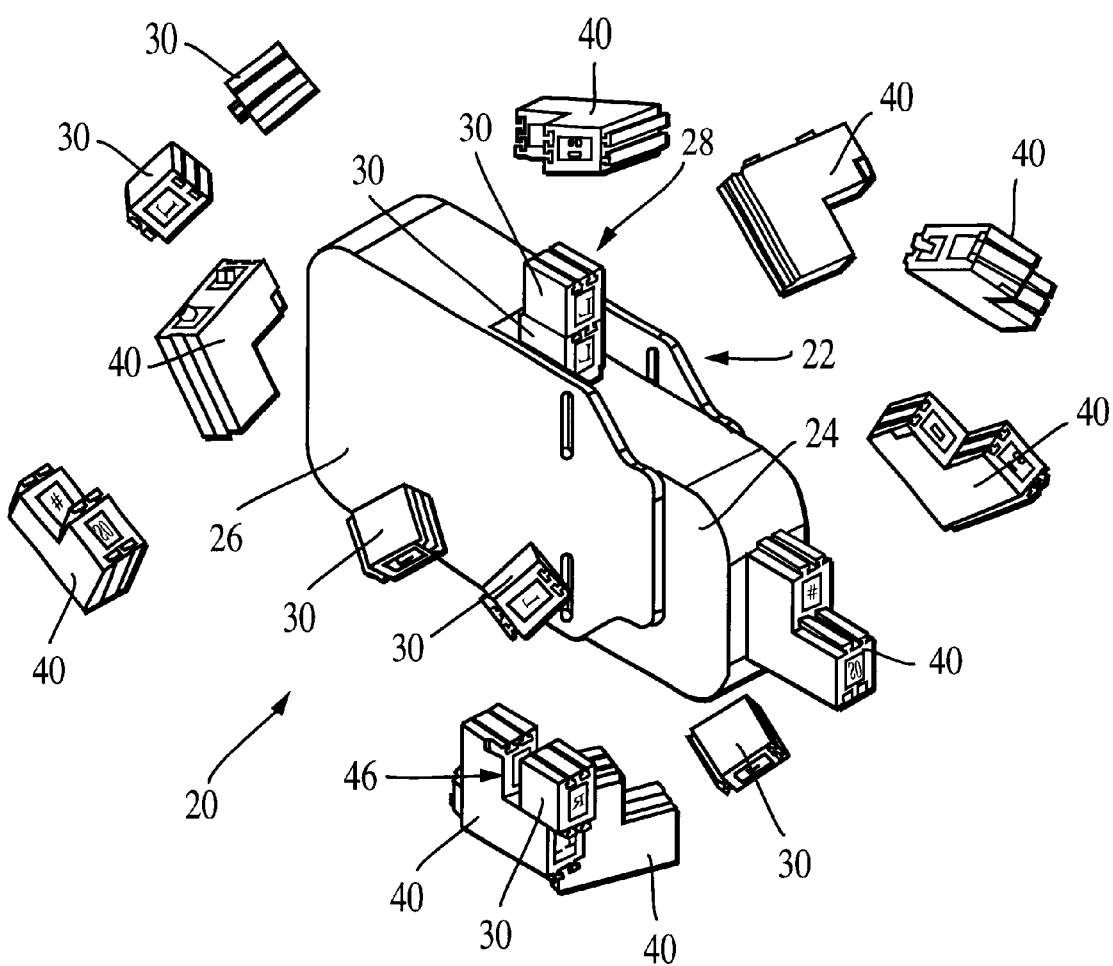
FIG. 2 is a schematic illustration of a Turing machine constructed and operative in accordance with a preferred embodiment of the present invention.

FIG. 2 is a schematic illustration of a Turing machine, generally referenced 20, constructed and operative in accordance with a preferred embodiment of the present invention. The preferred embodiment illustrated in FIG. 2 is an implementation of the Turing machine 20 with mechanical components. The operation of the Turing machine 20 is based on the external driven motion of these components.

During the course of the description, machine 20 is referenced by using the terms Left, Right, Up and Down. This is done purely for the purpose of clarity and explanation. The machine does not rely on orientation or gravity to function. This extends through into the molecular and other implementations of the machine.

Additionally, although hereinbelow for purposes of clarity the generally referenced numerical 20 is referred to as a Turing machine 20, it is understood that the term Turing Machine refers to a system implementing the Turing machine, and its components, and as described hereinbelow.

Turing Machine 20 comprises an enzyme 22, which comprises two connected parts; a two section enzyme 24 and a three section enzyme 26. Enzyme 22 holds a storage tape 28, which comprises a plurality of alphabet monomers 30 and a single state-transition monomer 40, strung in a sequence.

Alphabet monomers 30 represent the content of the cells of the Turing machine tape 12. Alternatively, alphabet monomers are known as tape monomers, however for purposes of clarity, herein the term alphabet monomers will be used.

State-transition monomers 40 are directional monomers, available as either a left state-transition monomer 42 or a right state-transition 44, and represent potential transitions of the Turing machine, which include the current state and current tape symbol, next state, next tape symbol and direction of movement.

A more detailed description of enzyme 22 and both of the monomers 40 and 30 is included hereinbelow in reference to FIGS. 3–7.

A matched state-transition monomer 40 and alphabet monomer 30 form a state-transition dimer 46. The process, description and criteria for dimer matching will be described hereinbelow.

The Turing machine 20 operates in the presence of an abundant supply of additional free-flowing state-transition monomers 40 and alphabet monomers 30.

The environment can affect the progress and course of the computation by controlling the availability of state transition monomers 40 and alphabet monomers 30. In a deterministic Turing machine, the environment can suspend the computation in a particular state S, by not making available state transition monomers with source state S. In a non-deterministic Turing machine that can proceed from state S to either state S' or state S", the environment can allow the computation to progress from S to S', but not to S", by making available state transition monomers 40 of the first kind but not of the second kind.

An extension of this mechanical embodiment into other implementations is conceivable, for example a mixture of suitable polymers and an enzymatic processor in a container of some sort where billions of parallel processes could take place simultaneously. The explanation that follows describes in detail the operation of a mechanical 'Enzymatic Turing Machine'. It can be seen that this mechanical model can be extended into the bio-chemical world as well as other types of molecular and sub molecular fields.

Figure 29:
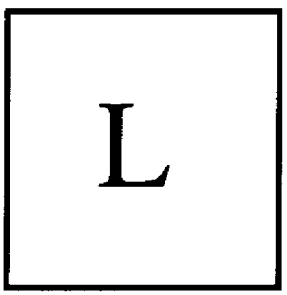
FIG. 29 is a schematic illustration of sample calculations in accordance with a preferred embodiment of the present invention.
Figure 29:
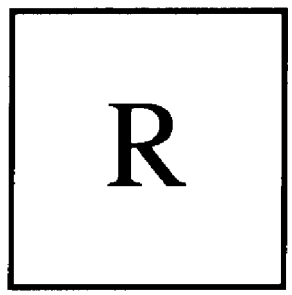
Figure 30A:
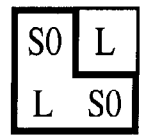
FIGS. 30a–30h, sometimes referred to collectively as FIG. 30, are further schematic illustrations of sample calculations in accordance with a preferred embodiment of the present invention.
Figure 30B:
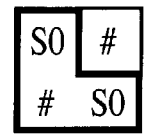
Figure 30C:
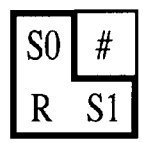
Figure 30D:
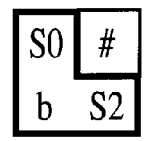
Figure 30E:
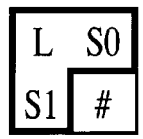
Figure 30F:
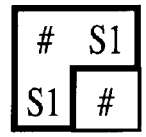
Figure 30G:
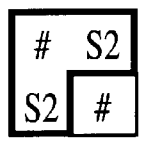
Figure 30H:
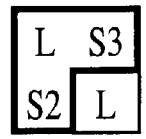
Figure 89:
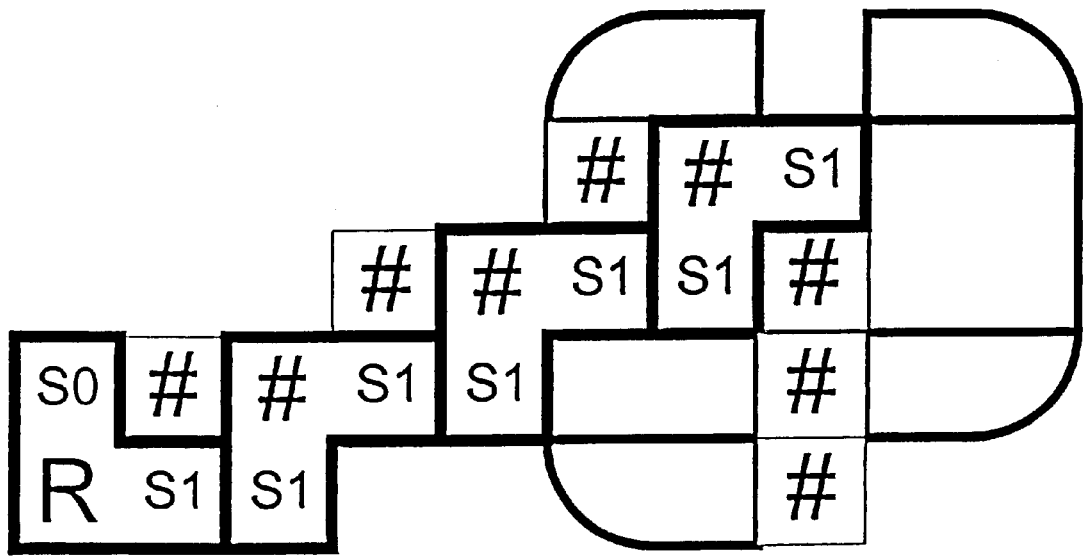

Technically there are two forms of output that are realized by this system. They can be most clearly seen from the progression of the computation as depicted in FIGS. 29–89, where detailed examples are shown. The primary output is the storage tape 28, which is a string of alphabet monomers 30 that can be interpreted to derive the result of the computation. The result may be encoded in the state the system is left in after computation ceases, or in a particular pattern left in the storage tape 28.

The secondary output is the string of used or processed state-transition monomers, known as a state-transition history polymer 160. This string of monomers, or polymer, reflects the entire computation history. Practically this polymer can be used for debugging or trace purposes, to validate and verify 'programs', as well as to analyze the systems performance and accuracy. Theoretically, the embodiment of a string of used tape monomers 140 indicates that in Charles Bennet's sense of a "Brownian Computer" the system is reversible. No memory content is ever actually erased as all old state and tape monomers are preserved in this second output string.

While the current descriptions cover a physical and molecular implementation, it should be noted that there are many diverse forms of implementation of this approach, for example but not limited to:

Magnetic tape, using magnetic domains or larger areas for data storage; Optical pits and bumps; Data storage areas, as to be some form of energy source, or well, atomic forces, gravitational forces, electrostatic charge, photonic energy states in semiconductors or other materials; and/or implementation as a standing wave or current in a superconducting material or field.

Additionally, there are many deconvolution methodologies, or means of interpreting the output form systems, for example but not limited to:

Mass Spectroscopy; Visual Inspection, either un-aided or with magnification, including electron microscopes, and confocal types, not limited to the visible spectrum; Electrical charge detection (Current); Electrical Potential detection (Voltage); Audio or sonic interpretation; Classical or Quantum wave mechanics principles; Using SQUID technology to sense system state; Scintillation type detection, radioisotope detection; and/or Atomic force microscopy; Indirect methods, of detection, using a intermediate process. Any of the above means and others could be used to scan the results from the machine after or during processing. In the mechanical embodiment described herein we cover a visible, and physically easy to manipulate and deconvolute methodology.

Figure 3:
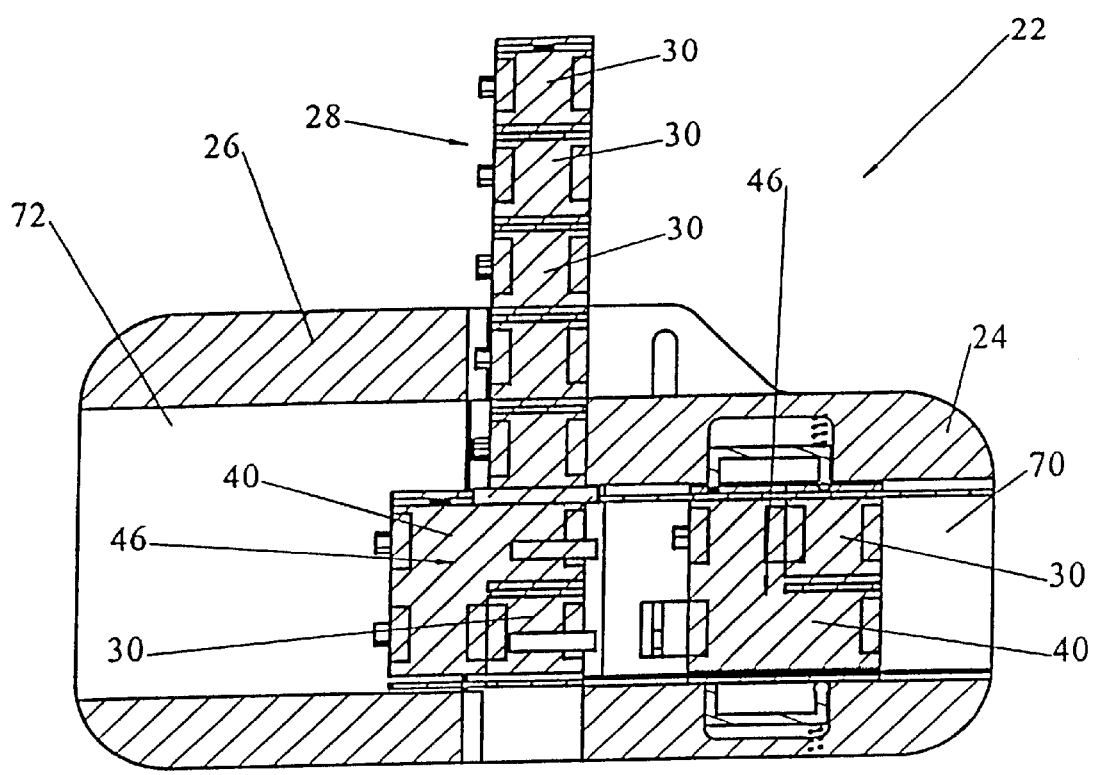
FIG. 3 is a sectional view of the enzyme showing various components in process through the enzyme, operative in accordance with a preferred embodiment of the present invention.

Reference is now made to FIG. 3, a sectional view of enzyme 22 showing various monomers in process through the enzyme 22. The computation of the Turing machine 20 consists of a repetition of a basic step in which dimer 46 enters the enzyme 22 through the two section enzyme 24 and, under certain conditions to be specified in detail below, displaces the existing state-transition monomer 40, and possibly also one of its adjacent alphabet monomers 30, from the tape. The displaced monomers leave the enzyme 22 through the three section enzyme 26.

Alphabet Monomers and State-transition Monomers

Figure 4:
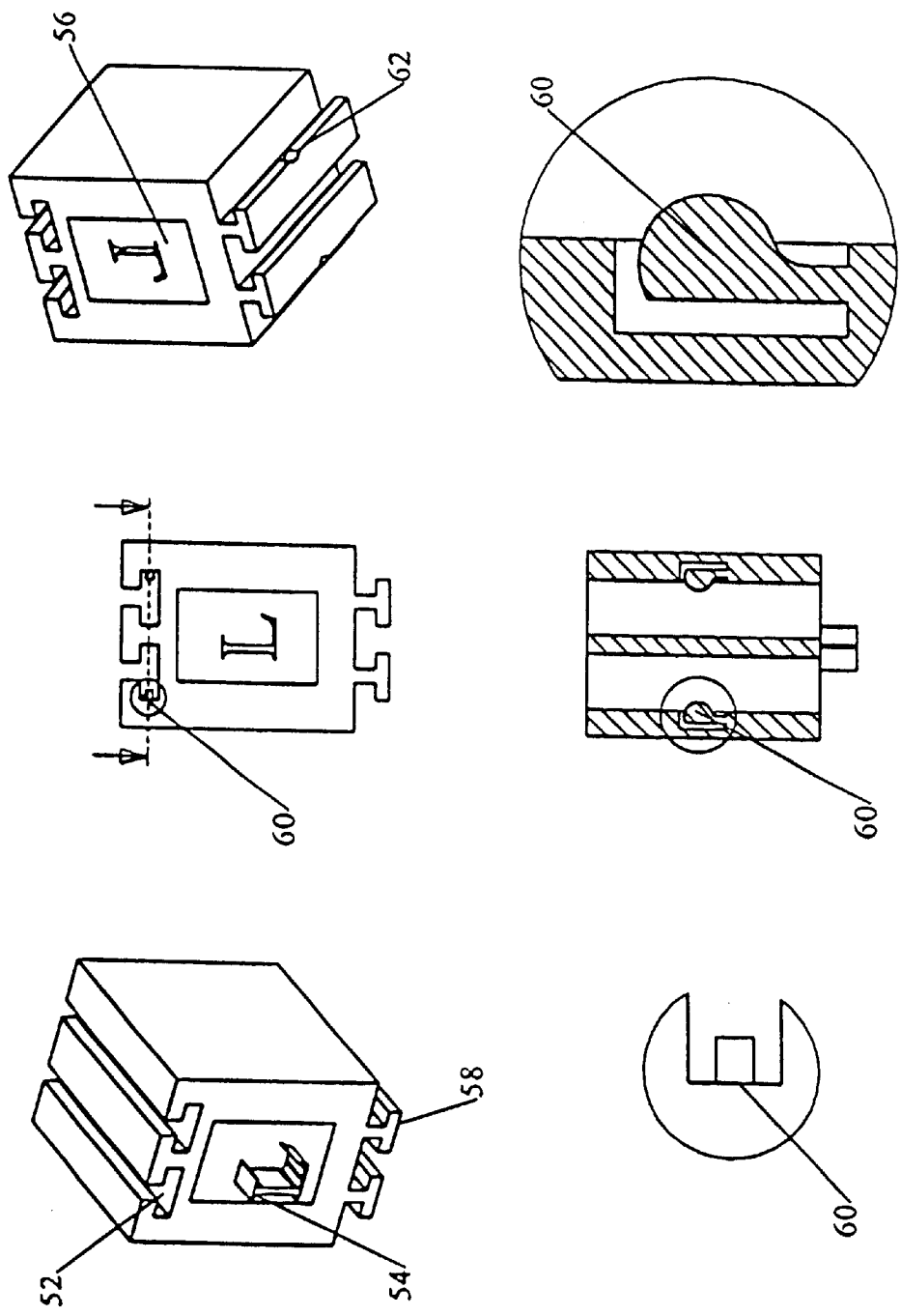
FIG. 4 is a schematic illustration of an alphabet monomer.

Reference is now made to FIG. 4, a detailed view of alphabet monomer 30, in this preferred embodiment, a type "L" alphabet monomer.

Alphabet monomers 30 comprise a T-slot 52, a letter protrusion 54, a letter indentation 56, a T-bar 58, a knob 60, and a notch 62. Alphabet monomers 30 can be assembled into a sequence representing the non-blank content of the tape 12.

T-slot 52 enables alphabet monomers 30 to be interlocked with another alphabet monomer 30 to create a long storage tape 28. T-slot 52 interlocks with the T-bar 58. T-bar 58 protrudes down from the alphabet monomer 30, and interlocks with the T-slot 52 of the next alphabet monomer 30 in the alphabet monomer chain (storage tape 28). In some instances described in detail below, T-slot 52 interlocks alphabet monomer 30 with state transition monomer 40.

Letter protrusion 54 is the feature of the alphabet monomer 30 which keys the part. In FIG. 4, the exemplary alphabet monomer 30 illustrated is an 'L' type part, and such the letter protrusion 54 is a positive or protruding 'L' used on the forward edge or direction of travel. Note that the converse of letter protrusion 54 is letter indentation 56, the negative edge or pocket that is used on the rearward edge of travel. Letter indention 56 will only accept matching letter protrusion 54, i.e. letter indentation L will only match letter protrusion L.

Knob 60 enables the adjacent alphabet monomers 30 to be locked together in such a manner that it is not easy for them to slide apart once they have been assembled. A notch 62 engages with knob 60 to produce the interlocking nature of the alphabet monomers 30.

Figure 5:
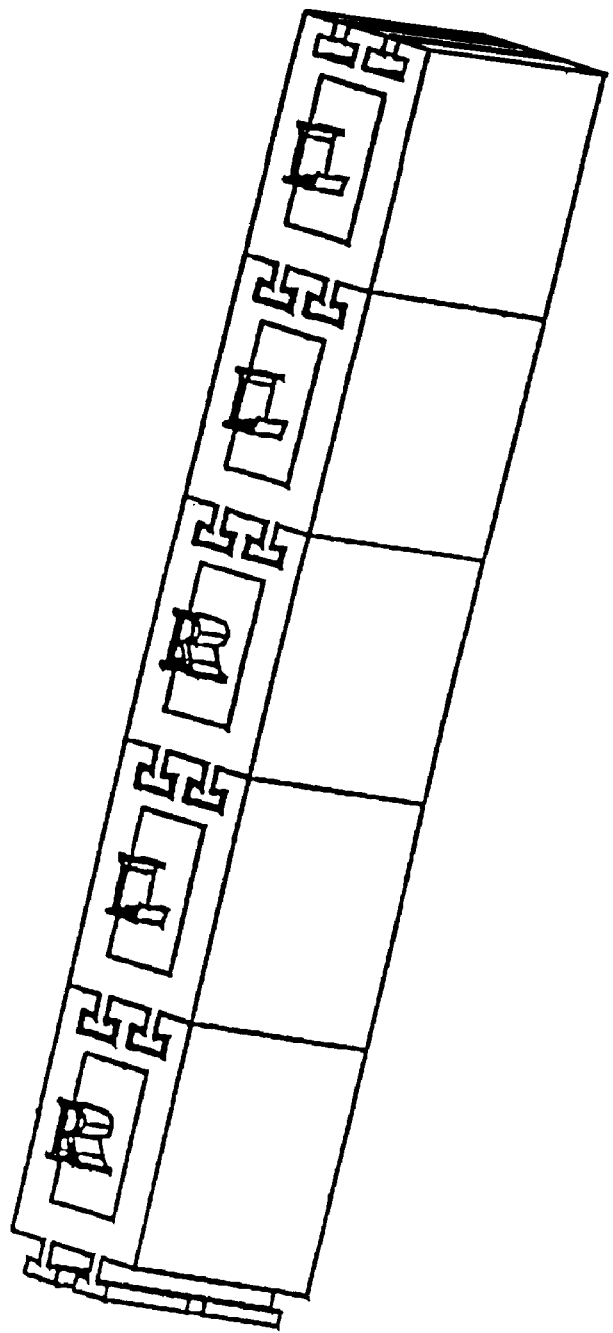
FIG. 5 is a schematic illustration of a collection of interlocked alphabet monomers.

FIG. 5 is a collection of interlocked alphabet monomers 30, known as a storage tape 28 of monomers 30, and which is the output from the enzyme 22, or specifically the enzymatic computational device, as discussed hereinabove in reference to FIG. 2. The alphabet monomers 30 are assembled according to the program encoded in the state-transition monomers 40, or directional monomers. The resulting output of interlocked alphabet monomers 30 can be interpreted in some fashion to derive the output.

As shown in FIGS. 4 and 5, alphabet monomers 30 are designed so that they can be strung together into a "tape" 28, and so that the symbol each monomer represents can be sensed both from the sides. The sensing is done by state-transition monomers, as explained hereinbelow. Tape monomers are cubes, 1 unit long in each dimension.

Figure 6:
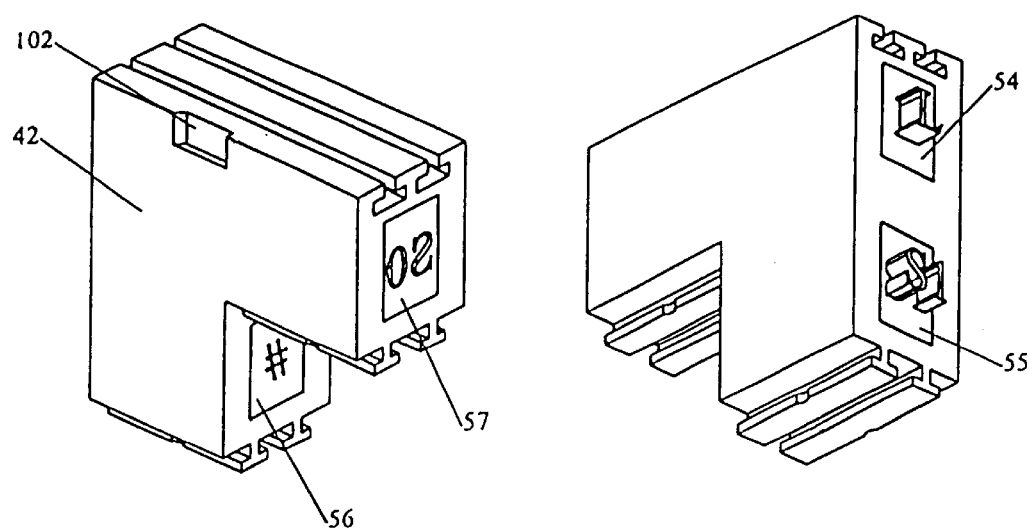
FIG. 6 is a schematic illustration of a plurality of left state-transition monomers.
Figure 7:
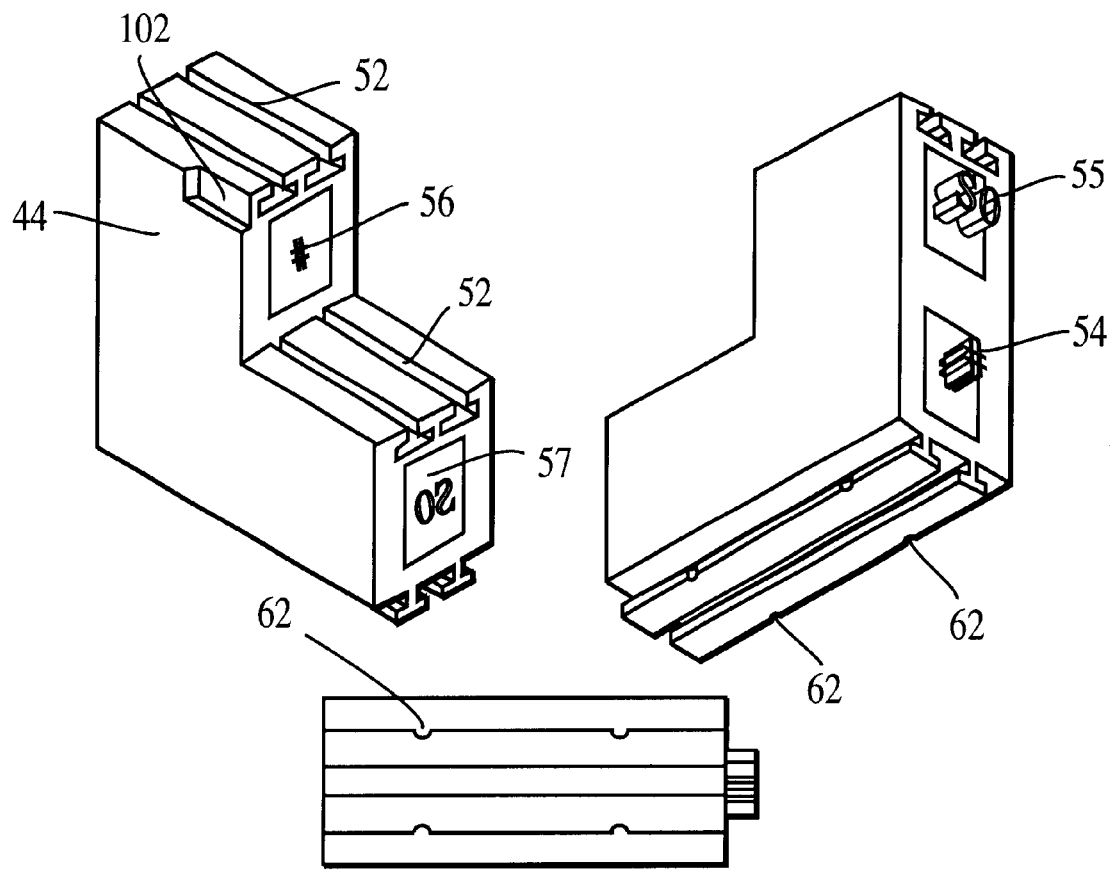
FIG. 7 is a schematic illustration of a plurality of right state-transition monomers.

Reference is now made jointly to FIGS. 6 and 7 which illustrate left state-transition monomer 42 and right state-transition monomer 44, respectively, which represent the quintuples of the Turing machine control program.

The state-transition monomer 40, either right or left, when combined with the appropriate single alphabet monomer 30, create either the right or left state-transition dimer 46, respectively. The resultant state-transition dimer 46 implements the transition, either right or left, that it represents.

The state-transition monomer 40 embedded into the storage tape 28 represents the location of the read/write head 16 as well as the current state of the control. Left direction state-transition monomer 42, will move the read write head one position left after processing. Conversely, right direction state-transition monomer 44, will move the read write head one position right after processing.

State-transition monomers 40, both right and left, comprise T-slot 52, a state indentation 57, letter indentation 56, a state protrusion 55, and letter protrusion 54. State-transition monomers 40 additionally have a second discriminator socket 63 former therein.

The T-slot 52 located on state-transition monomer 40 interlocks with T-bars 58 on alphabet monomer 30 and creates a connection that is retained as the monomers 30 and 40 are processed by the enzyme 22. The T-bars 58 also lock the state-transition monomers 40 and alphabet monomers 30 into place as they pass through the enzyme 22.

State indentation 57 is a negative edge or pocket used on the rearward edge of travel and keys the exit state of the enzyme 22, also known as the enzymatic processor. State indentation 57 is also the transition state that the read/write head 16 is in after processing.

Letter protrusion 54 is a positive or protruding symbol used on the forward edge or direction of travel and matches only to the appropriate type of alphabet monomer 30 as the other half of the dimer pair. State protrusion 55 is a positive or protruding symbol used on the forward edge or direction of travel and defines the previous state of the machine.

Socket 63 which will be described in detail hereinbelow in reference to FIGS. 16–19, is utilized by enzyme 22 in the discrimination process.

State-transition monomers 40 are shaped so that each monomer 40 represents a particular transition rule. As an example, FIG. 6 shows a left state-transition monomer 42 implementing the transition <S1, L, S0, #, left>. In this preferred embodiment, state indentation 57 keys the exit state of the enzyme 22 as the S0 state, letter indentation 56 forces a '#' type alphabet monomer 30 to be the other half of the dimer 46 pair, state protrusion 55 requires the previous state of the machine 20 to be S1, and letter protrusion 54 requires the adjacent tape monomer 30 to be an L type monomer.

The bottom part of the left state transition monomer 42 senses the state S1 and the symbol 'L' to its left. The cavity on the lower-right quadrant accommodates the alphabet monomer 30 representing the symbol '#', and the top-left quadrant represents the new state S0.

Reference is now made to FIG. 7, which illustrates the symmetric right state-transition monomer 44. In this example the letter indentation 56 key will only accept an alphabet monomer 30 of the # type, state indentation 57 keys the exit state of the enzyme 22 as being the S0 state, state protrusion 55 requires the previous state of the machine 20 to be S0 in order to be a valid instruction set and letter protrusion 54 requires the adjacent tape monomer 30 to be an # type.

As shown in FIG. 6 and FIG. 7, in order to enable correct transitions, State-transition monomers 40, both left and right, monomers 44 and 42 respectively, are two-units wide, two units high, and one-unit deep.

The Enzyme

Figure 8:
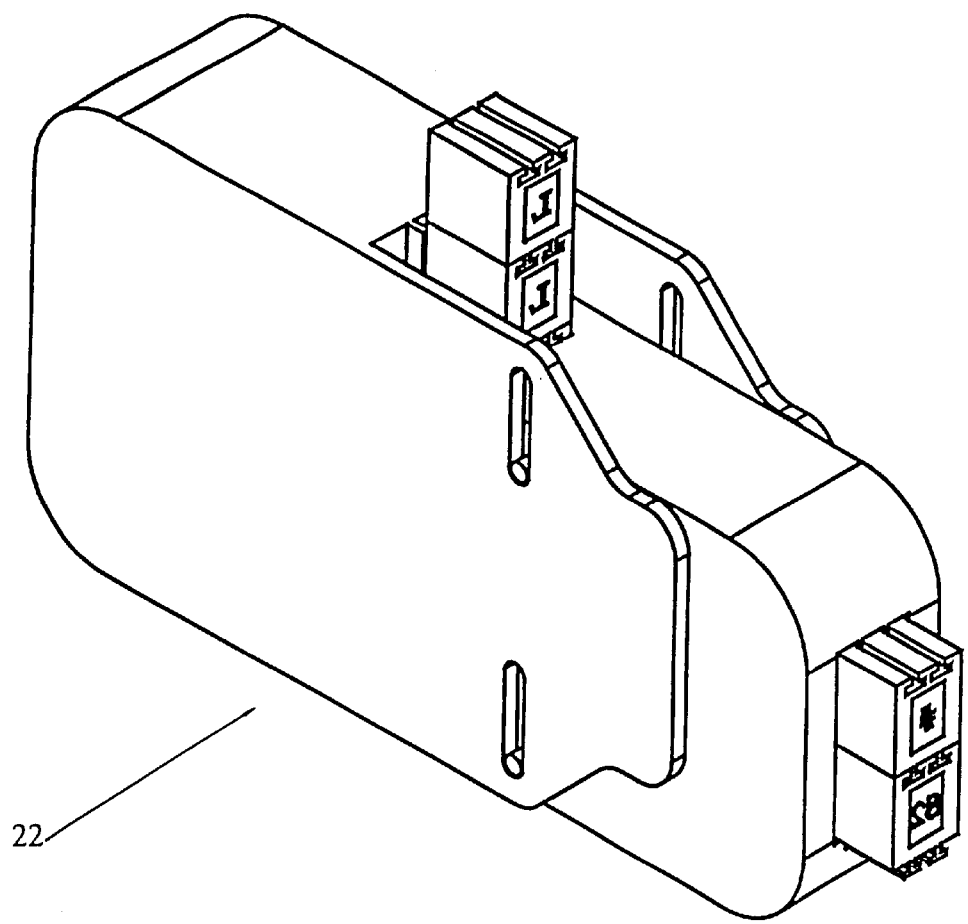
FIG. 8 is a schematic illustration of an enzyme processing a dimer.

The state of the computation is realized by a polymer consisting of alphabet monomers 30, representing the content of the storage tape 28, and by one state-transition monomer 40, representing both the location of the read/write head 16 and the state of the control. Reference is now made to FIG. 8, an illustration of the enzyme 22 "holding" the storage tape 28 and the state-transition monomer 40. Enzyme 22 provides for the modification of storage tape 28 according to the transition rules, as illustrated in FIG. 9 and described herein below in reference to that figure.

Figure 9:
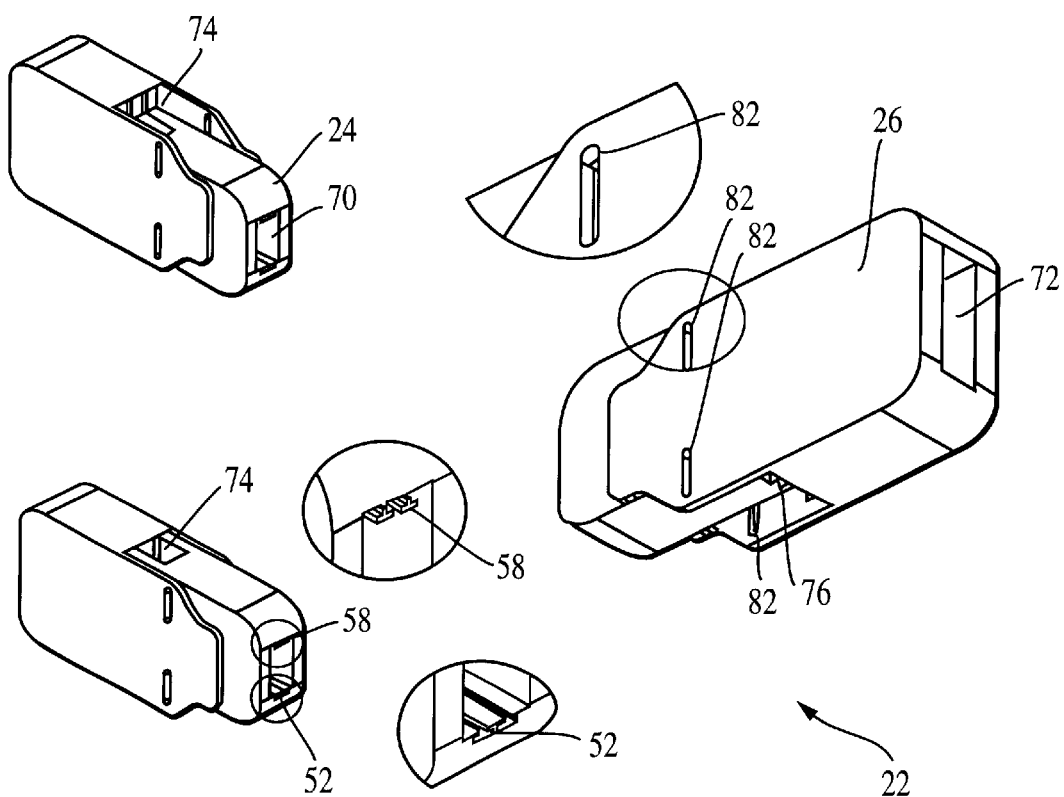
FIG. 9 is a schematic illustration of the enzyme's various components.

As shown in FIG. 9 the enzyme 22 has four "tunnels", a top tunnel 70, a bottom tunnel 72, a left tunnel 74, and a right tunnel 76.

The left tunnel 74 and right tunnel 76 contain the portions of the storage tape 28 to the left and to the right of the state-transition monomer 40. The left and right tunnels, 74 and 76 respectively, allow for movement of the storage tape 28, to the left and to the right, which is needed to effect transitions. The left and right tunnels, 74 and 76 respectively, are one unit wide and one unit high.

The top tunnel 70 passes through the two section enzyme 24 and allows the entry of dimers 46 consisting of a state-transition monomer 40 and a matching alphabet monomer 30. As explained hereinabove in reference to FIGS. 6 and 7, the enzyme 22 has been left in a certain state as defined by the exiting state-transition monomer 40 and its paired alphabet monomer 30. Only the appropriate dimers 46 with the correct states and letter types will be accepted. Components other than the appropriate dimer 46, such as single monomers or non-matching dimers will be rejected by features inside the top tunnel 70. These features will be described in detail hereinbelow in reference to FIGS. 11–24. The top tunnel 70 is two units wide and one unit deep.

The bottom tunnel 72 passes through the three section enzyme 26 and allows for the used state-transition monomers 46 and alphabet monomers 30 to pass through. The exiting state-transition monomer 40, as well as the overwritten tape monomer 30, if any, are displaced by the entering state-transition dimer. The enzyme 22 is structured so that the current State-transition Dimer and the tape monomer 30 to its left, if any, can be displaced only if the bottom of an entering "move left" State-transition Dimer matches the current state and the symbol to its left. Symmetrically, a "move right" State-transition Dimer can displace the current state and the tape monomer 30 to its right, if any, only if its bottom section matches the current state and the symbol to its right. The bottom tunnel 72 is three units wide and one unit deep.

In order to assure correct orientation of the entering dimer 46, enzyme 22 comprises T-bars 58 and T-slots 52. If the entering dimer 46 is oriented correctly, the T-bars 58 and T-slots 52 of enzyme 22 match with the corresponding T-bars 58 and T-slots 52 located on the entering dimer 46. If the entering dimer 46 presents itself upside down, the T-bars 58 and T-slots 52 will not match and the dimer 46 is rejected from the enzyme 22.

Figure 10:
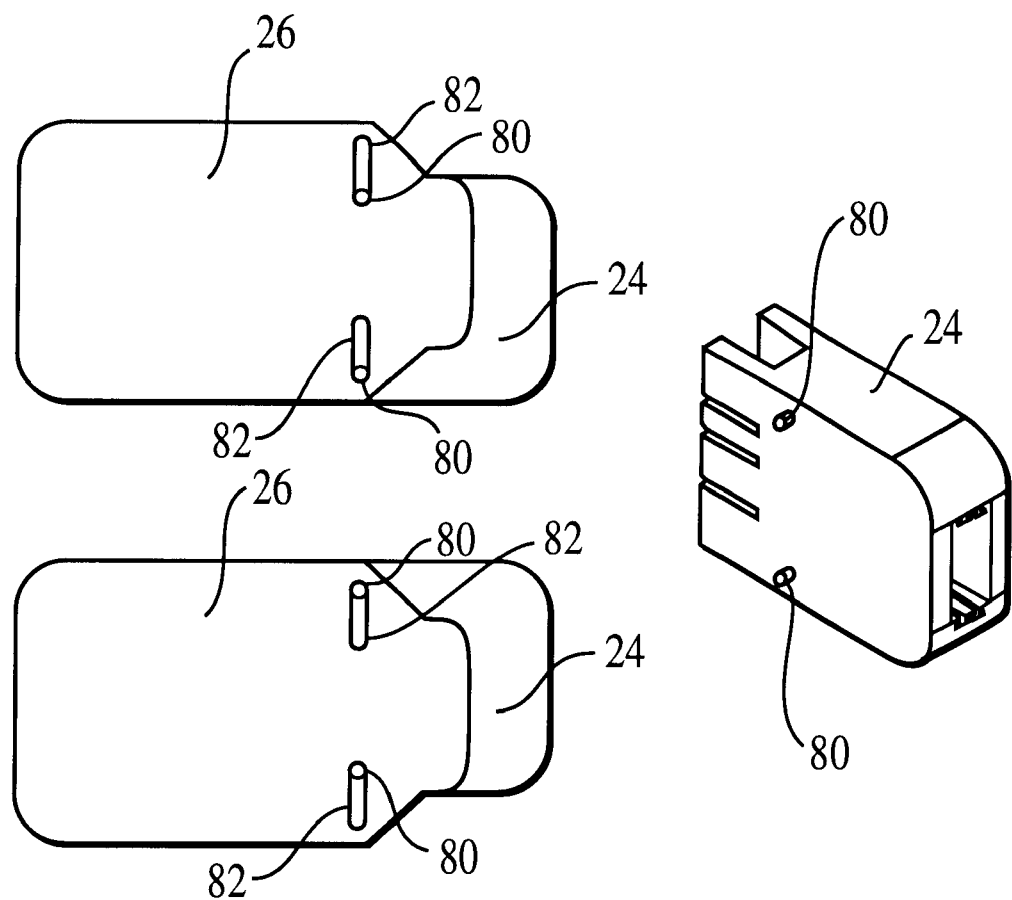
FIG. 10 is a schematic illustration of the enzyme's movement mechanism.

Reference is now made to FIG. 10, which illustrates a preferred embodiment of enzyme 22 and an example of a mechanism which affords movement between the top and the bottom part therein, the two section enzyme 24 and the three section enzyme 26, respectively. Please note that while the preferred embodiment discussed herein refers to a top and a bottom part, these terms are relative only and used for purposes of clarity of explanation only.

In order to provide movement of one part relative to the other, enzyme 22 comprises links 80 and slots 82. Preferably four slots 82 are located on the three section enzyme 26 and four links 80 are located on the two section enzyme 28. The four links 80 engage with associated slots 82 and only allow for relative motion equal to the height of one single alphabet monomer 30. The movement is either to the left or right, providing for the top tunnel 70, which is two units wide, to be aligned to the left or to the right of the bottom tunnel 72, which is three units wide, thus enabling a move left, or a move right transition, respectively.

In a preferred embodiment Turing machine 20 has some essential features embodied therein. Detailed examples of each feature in particular shall be covered and then a description of the overall processing function will follow.
Discrimination against Direction Monomers with no Alphabet Monomer.

In order to prevent entrance by state-transition monomers 40 with no alphabet monomers 30 or mismatched state-transition monomers 40 or mismatched alphabet monomers 30, the Turing machine 20 has implemented two stages of discrimination. To be discussed now in reference to FIGS. 11–15 is a first discriminator 90. Second discriminator 100 will be discussed further hereinbelow.

Figure 11:
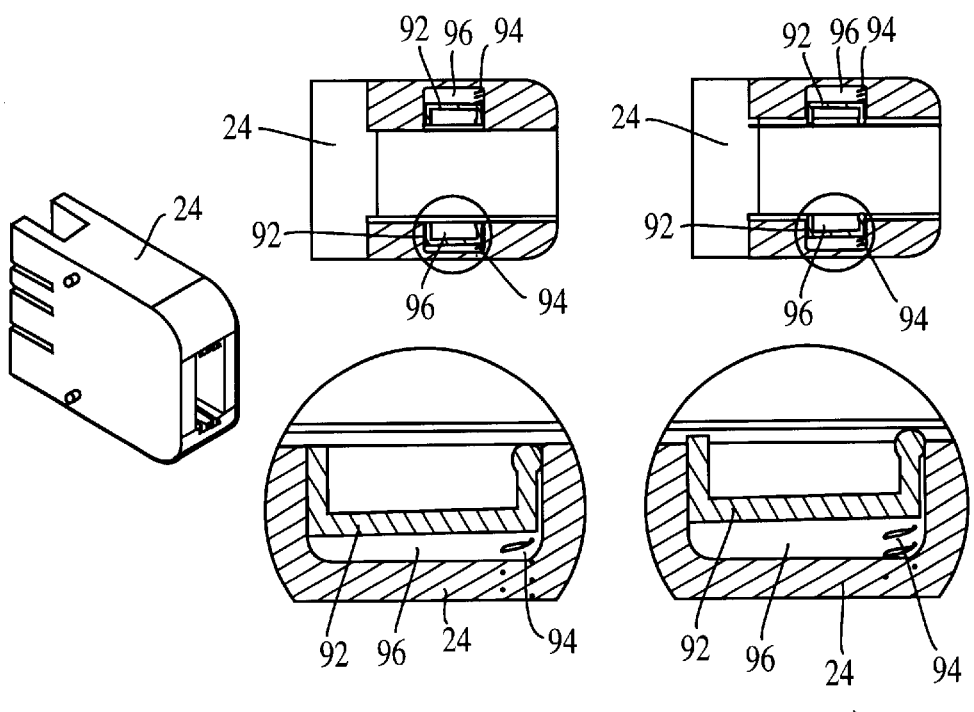
FIGS. 11–15 are sectional views of the two section enzyme and of the enzyme's first discrimination mechanism.

Reference is now made to FIG. 11, a sectional view of the two section enzyme 24. Discriminator 90 in the two section enzyme 24 comprises a plurality of spring loaded bars 92, located in a plurality of pockets 96. Preferably enzyme 24 comprises two spring bars 92 located in two pockets 96.

As shown in FIG. 11, the first discriminator 90 is located in the two section enzyme 24, and discriminates against state-transition monomers 40 with no alphabet monomer 30. The discrimination by the two section enzyme 24 is accomplished by using two spring loaded bars 92.

In a preferred embodiment state-transition monomer 40 endeavors to enter the two section enzyme 24 through the top tunnel 70. If the state-transition monomer 40 has a matching alphabet monomer 30, then the T-bars 58 and T-slots 52 of the appropriate monomers and enzyme match, and press the spring bars 92 into their pocket 96. If, however, state-transition monomer 40 entering does not have a matching alphabet monomer 30, then the T-bars 58 and T-slots 52 of the appropriate monomers and enzyme do not match, and spring bars 92 are free to spring out of their pockets 96, thereby barring the entrance of the mismatched monomers.

Figure 12:
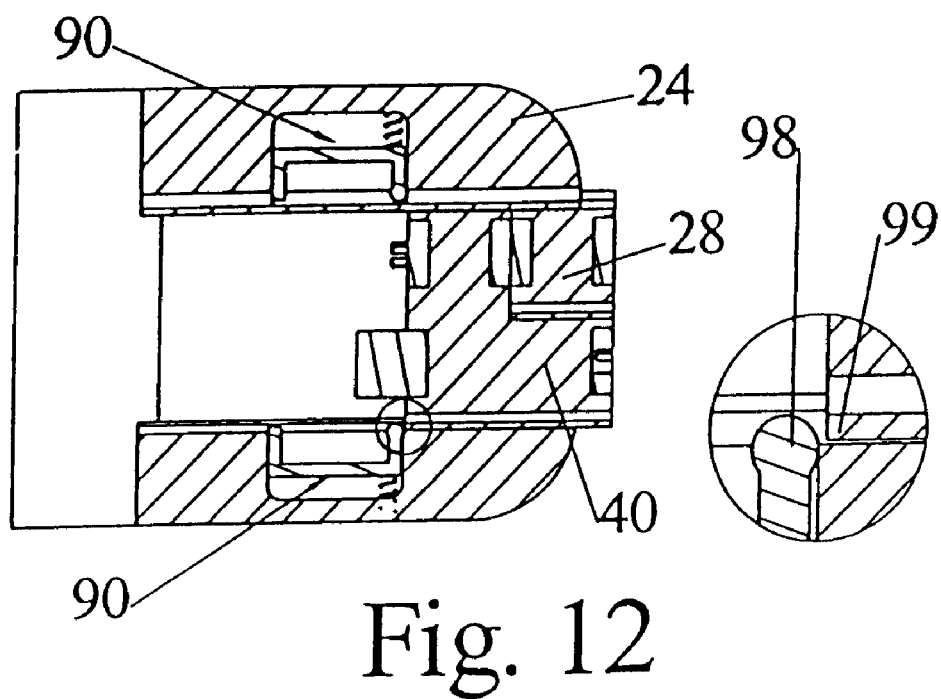

Referring now to FIG. 12, which illustrates the discrimination process in more detail. As shown clearly in FIG. 12, spring bars 92 include roller 98. The state-transition dimer 40 and alphabet monomer 30 enters via the top tunnel 70 into the two section enzyme 24. As shown in the figure, just prior to discrimination, a front edge 99 of the state-transition dimer 46 is about to push the roller sections 98 of the spring bars 92 out of the way.

Figure 14:
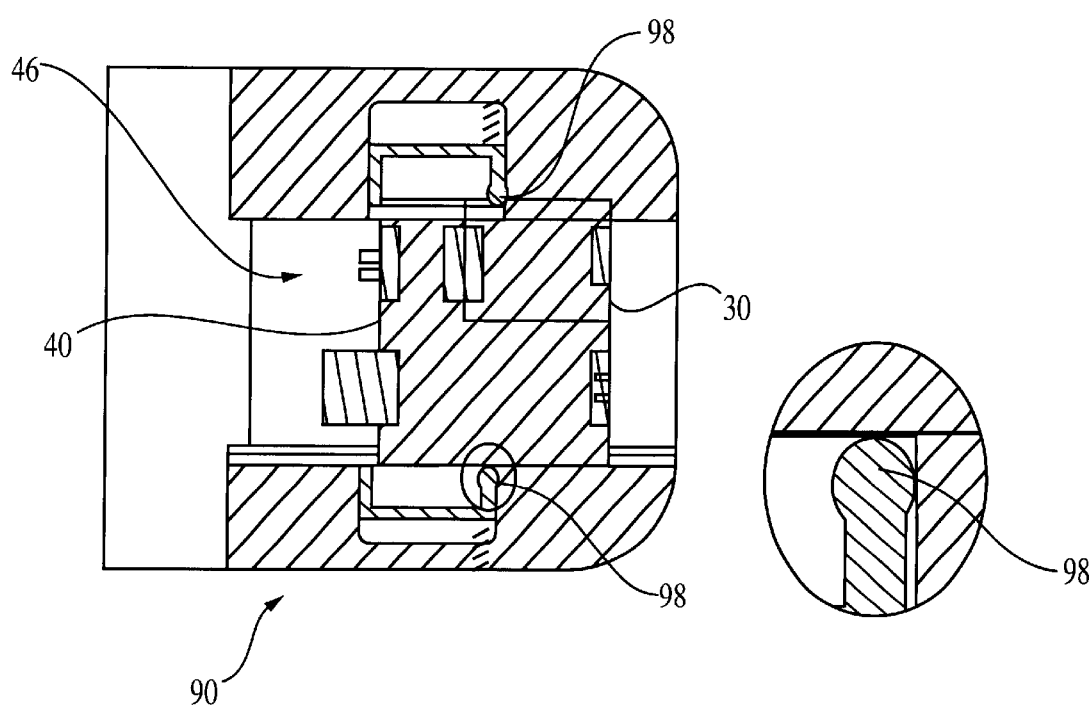

In FIG. 14 the state-transition monomer 40 and alphabet monomer 30, are mismatched and cannot mate correctly. The letter protrusion 54 of the alphabet monomer 30 does not match the letter indentation 56 of the state-transition monomer 40, therefore preventing contact between the two monomers.

Therefore, due to the gap between the monomers, after the state-transition monomer 40 passed the roller 98 of discriminator 90, the spring bar 92 springs down out of its position in pocket 96. A leading edge 91 of the bar 92 halts the progress of the state-transition monomer 40, while roller 98, the back end of spring bar 92, enters into the gap between the monomers and halts the progress of the alphabet monomer 30.

Figure 13:
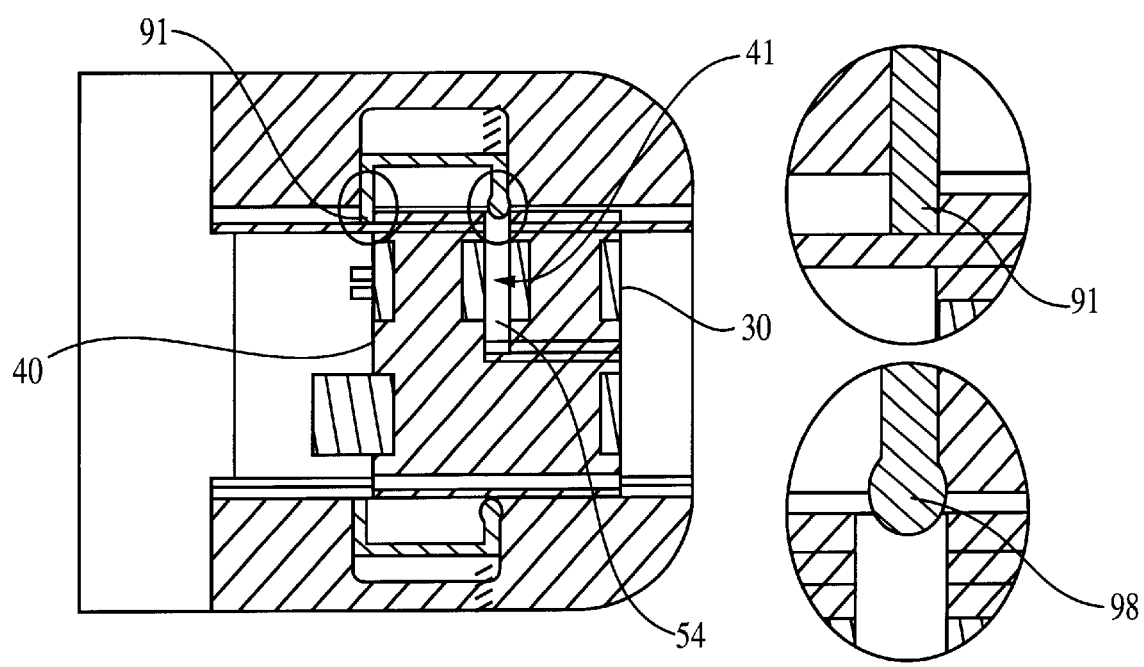

In FIG. 13, the state-transition dimer 40 is midway through the discrimination mechanism 90. In this particular instance the state-transition monomer 40 and the alphabet monomer 30 are complementary, creating a dimer 46, and therefore the discriminator 90 does not impede the progress of the dimer pair through the system.

Figure 15:
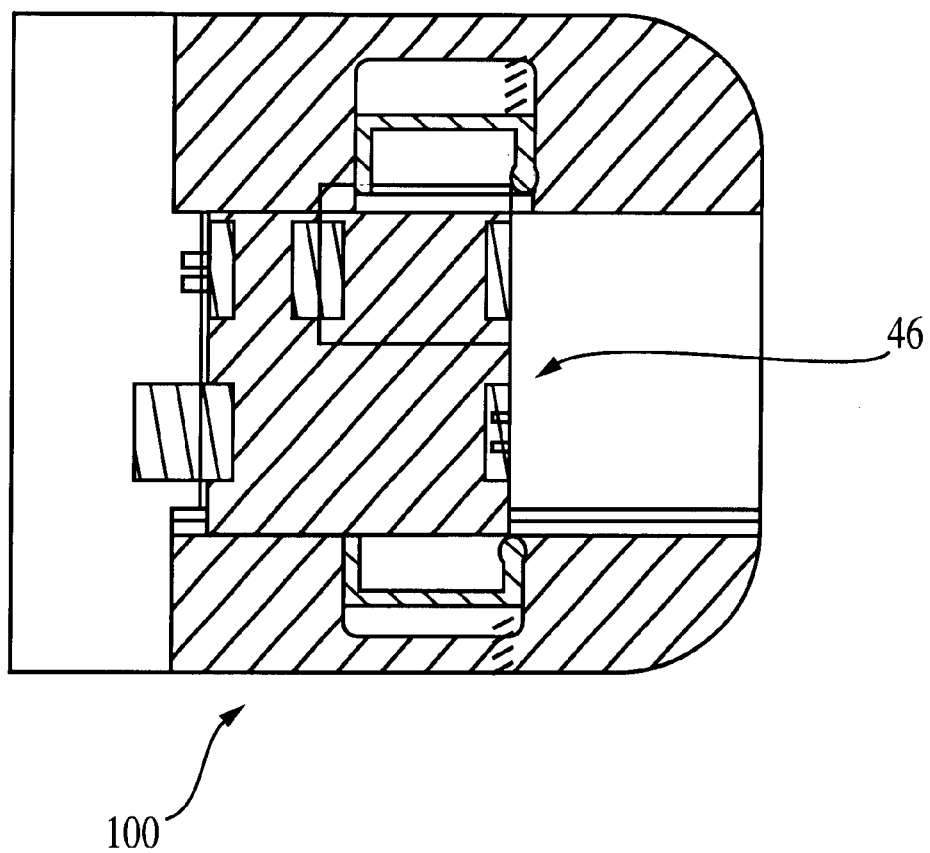

In FIG. 15, the matched dimer 46 is past first enzyme 22 and presented to second discriminator mechanism 100, while this occurs the first mechanism 90 is still retracted and allows the dimer 46 to return should the second discriminator 100 not allow passage.

Figure 16:
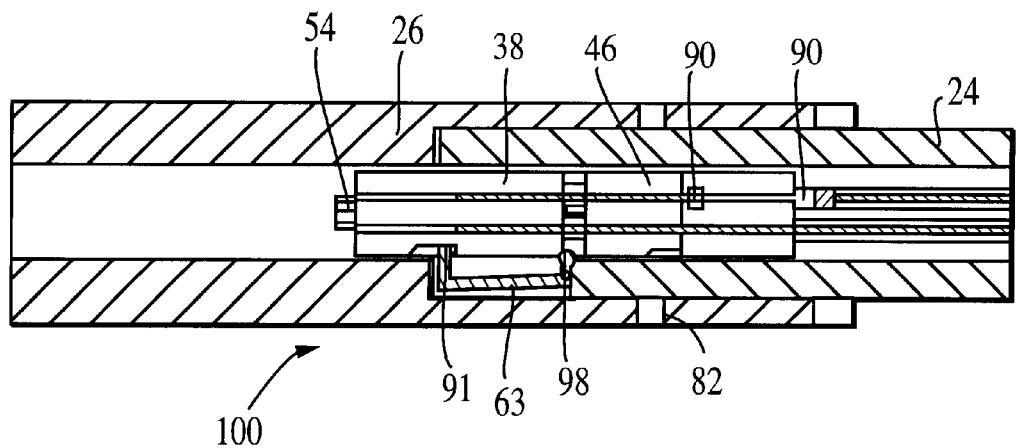
FIGS. 16–19 are sectional views of the enzyme's second discrimination mechanism.

The spacing and shape of the mechanism is such that a second dimer pair 46 can not gain access to pass the first discriminator erroneously.
Discrimination of Dimers which are mismatched to the Tape Monomer Reference is now made to FIGS. 16–19 which illustrate the second level of discrimination as performed by second discriminator 100. As illustrated in FIG. 16, the discriminator 100 is situated between the two section enzyme 24 and the three section enzyme 26. Similar to first discriminator 90, the second discriminator 100 comprises spring loaded bar 92, the leading edge 91 of bar 92, pockets 96 formed therein and roller 98. Note that in all cases the bar 92 of discriminator 100 is spring loaded towards the three section enzyme 26, and not in the reverse direction.

After the dimer entering 46 has successfully passed the first discrimination 90, it must successfully match with the current system state of the enzyme 22. The current system state is represented by state indentation 57 of the existing dimer 46 currently in the top tunnel 70.

The existing dimer 46, which is barring the path of the entering dimer 46, is the last link, or monomer, in the history polymer 160, which was previously processed by enzyme 22. Each of the other links, or monomers, in the history polymer 160were received by enzyme 22, successfully matched with the current system state, and processed out through the enzyme 22. Thus storage tape 28 is a polymer holding the history of the previous successful meshes or processes.

Referring now to FIG. 16, the entering dimer 46 approaches the existing state-transition monomer 40, which is part of the existing dimer 46 currently in the enzyme 22. The letter protrusion 54 and the state protrusion 55 of the entering state-transition monomer 40 must mate with the corresponding letter indentation 56 and state indentation 57 on the existing state-transition monomer 40. If they do not mate then a gap exists between the two state-transition monomers 40.

The resultant gap prevents the entering dimer 46 from making contact with the roller 98 and compressing the spring bar 92. Thus the spring bar 92 is free to spring up, causing leading edge 91 of bar 92 to mesh with socket 63 of the existing state-transition monomer 40. Additionally, roller 98 springs up and blocks the entrance of entering state-transition monomer 40.

The entering dimer 46 therefore cannot be processed due to mismatch of the state indentation 57 of current system state (the existing state-transition monomer 40) and the state protrusion 55 of the entering dimer 46. The existing state-transition monomer 40 is latched in place by leading edge 91 until a matching dimer 46 is presented.

Figure 17:
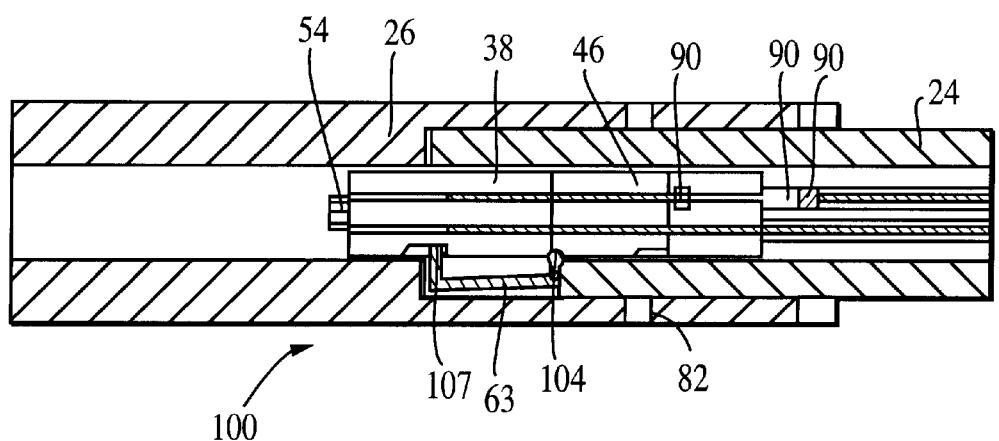

FIG. 17 illustrates an example of a successful mesh between the entering dimer 46 and the existing dimer 46. In this instance the entering dimer 46 matches the current system state as represented by the existing state-transition monomer 40. Thus the letter protrusion 54 of the entering state-transition monomer 40 meshes with the letter indentation 56 of the existing state-transition monomer 40. As the entering dimer 46 and the existing dimer 46 mesh, the bar 92 is pushed out of the way, and leading edge 91 releases socket 63. Additionally roller 98 is compressed and ceases to interfere with the progress of the entering dimer 46, allowing the approaching state-transition monomer 40 to act on the existing state-transition monomer 40.

Figure 18:
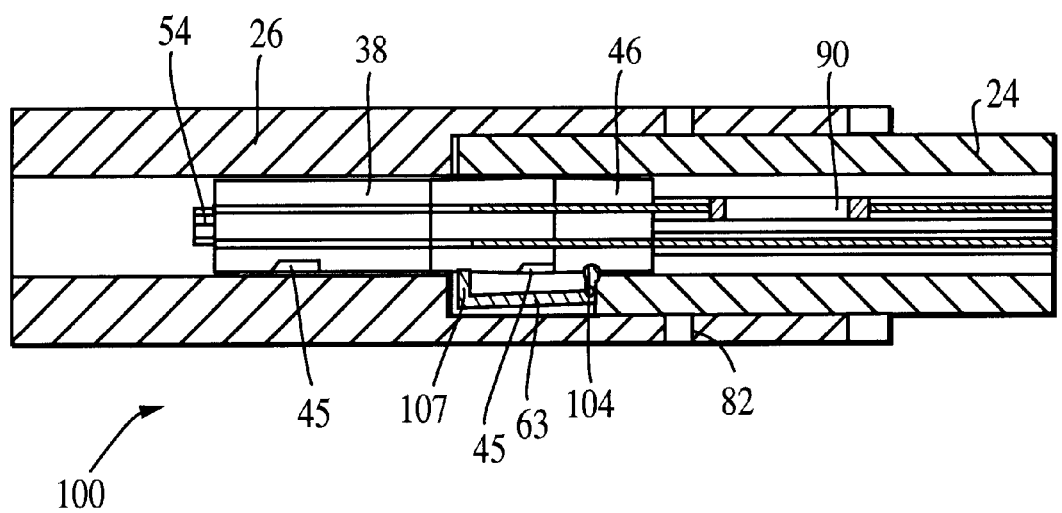

Reference is now made to FIG. 18 which illustrates the entering dimer 46 pushing through the discriminator 100 and acting on the storage tape 28, changing the system state and advancing the tape left or right, according to the type of state-transition monomer 40 contained within the entering dimer 46. The bar 92 is retracted as the processing occurs, but as the dimer 46 pushes through the socket 63 will be caught by the leading edge 91, thus holding the dimer 46 in place, and readying discriminator 100 ready for the next operation.

Figure 19:
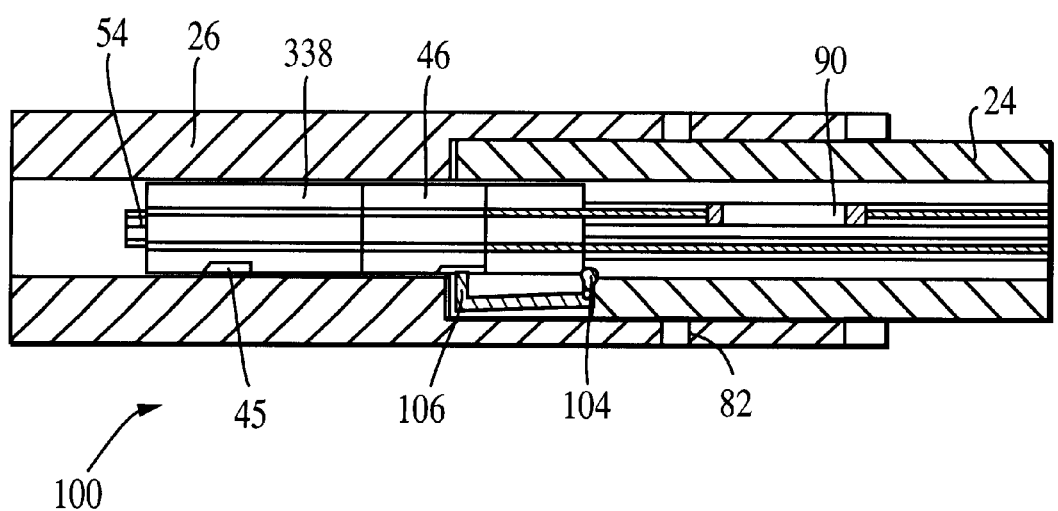

FIG. 19 illustrates an example where the entering dimer 46 has successfully moved through the discriminator 100, attached to the storage tape 28, and the discriminator 100 has reset itself waiting for the next approaching dimer 46.

Extension of the Tape Monomer to the Left or Right

For the correct functioning of the enzyme 22, the end conditions of the storage tape 28 must be considered. In a preferred embodiment it is assumed that the enzyme 22 has some form of data, such as storage tape 28, and the read/write head 16 is at the left or right end of the tape.

When the machine 20 is processing the middle of the storage tape 28 a typical valid left or right state-transition dimer 46 would consist of a system state protrusion 55 and a tape monomer protrusion 54, e.g. S0 and. However at the end conditions of the storage tape 28, extension is permitted, thus a different tape monomer protrusion is needed, and to this end, in a preferred embodiment, a special blank state-transition dimer 146 is implemented comprising a blank detector 110 and an associated blank feature curve 112. Dimer 146 adds extra elements to the extremities of the tape monomer.

Figure 20:
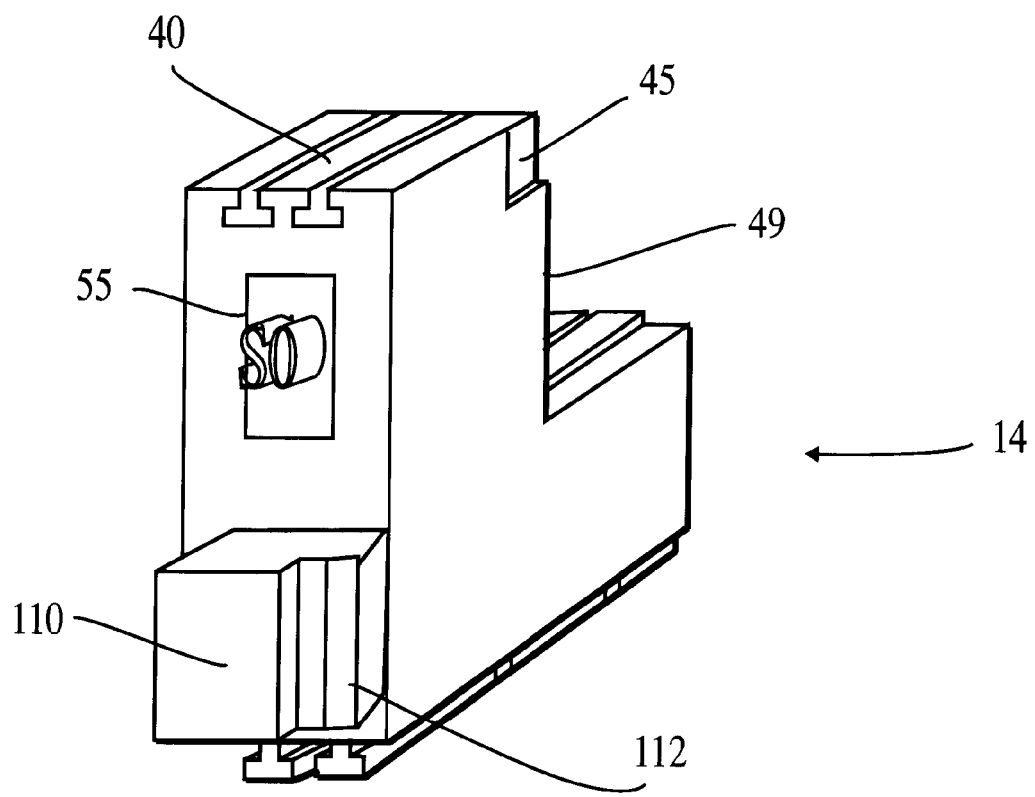
FIGS. 20–26 are sectional views of the enzyme's third discrimination mechanism and a blank state-transition dimer.

FIG. 20, referred to now, is a model representation illustrating implementation of the blank state transition dimer 146. The blank state-transition dimer 146 in FIG. 20 is right state-transition monomer 40 having the tape end condition state requirement of S0 represented by the state protrusion 55, and the special blank detector 110 with the curve 112 whose function and purpose will be explained in detail in reference to FIGS. 20–23. Although not shown in FIG. 20, the appropriate alphabet monomer 30 matching this state-transition monomer 40, and thus creating a blank transition dimer 146, is a # type monomer. This will be the extended element. The alphabet monomer type is for example purposes only, and can be any suitable required type.

Figure 21:
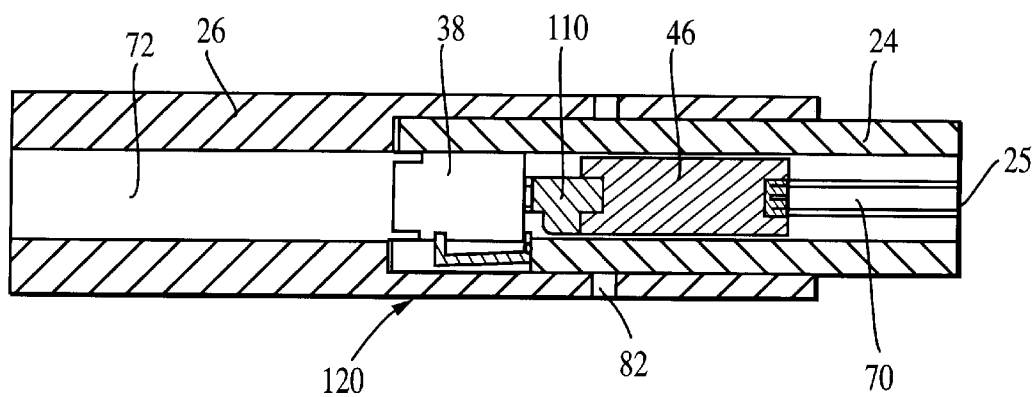
Figure 22:
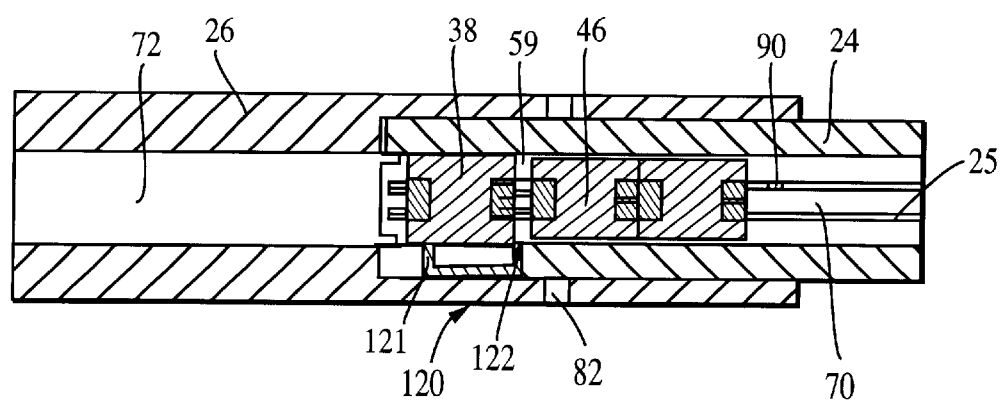
Figure 23:
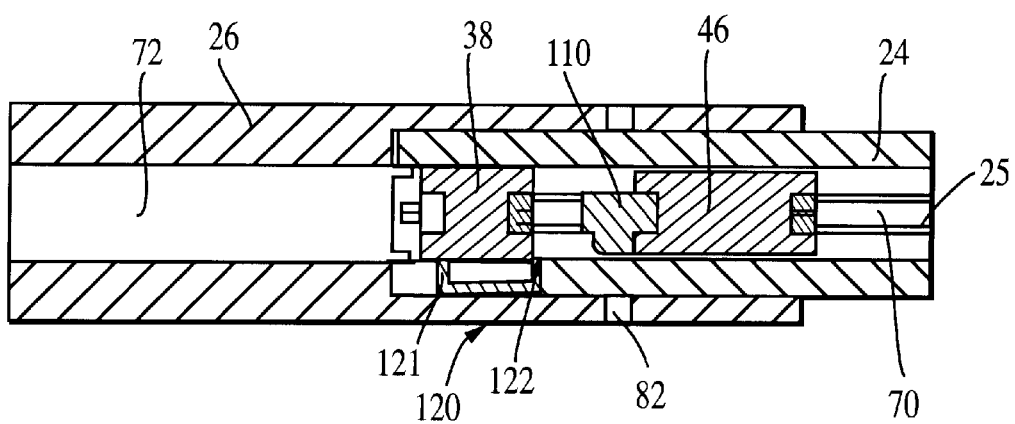

Reference is now made to FIGS. 21–23, an example of the implementation of the blank state-transition dimer 146 and a third discriminator 120. Discriminator 120 comprises an end sensor 121 and a point mechanism 122.

In the case illustrated in FIG. 21 the current system state is blank, as represented by a blank or flat state protrusion 55. As the blank state-transition dimer 46 approaches the storage tape 28, the curve 112 on the blank feature engages with the mechanism 120 and pushes it out of the way. The dimer 146 can now interact with the storage tape 28 to extend it.

In FIG. 22 the current system state position is occupied, the blank discrimination mechanism 120 is pushed aside by the contact between the mechanism end sensor 121 and the current system state monomer. Therefore the point mechanism 122 does not interfere with the approach of the entering dimer 46.

In FIG. 23, as the blank dimer 146 approaches the current tape state, the front of the blank detector 110 interferes with the state-transition monomer 40, and the mechanism 122 cannot be pushed out of the way. This stops the blank dimer 146 from acting on the storage tape 28.

Figure 24:
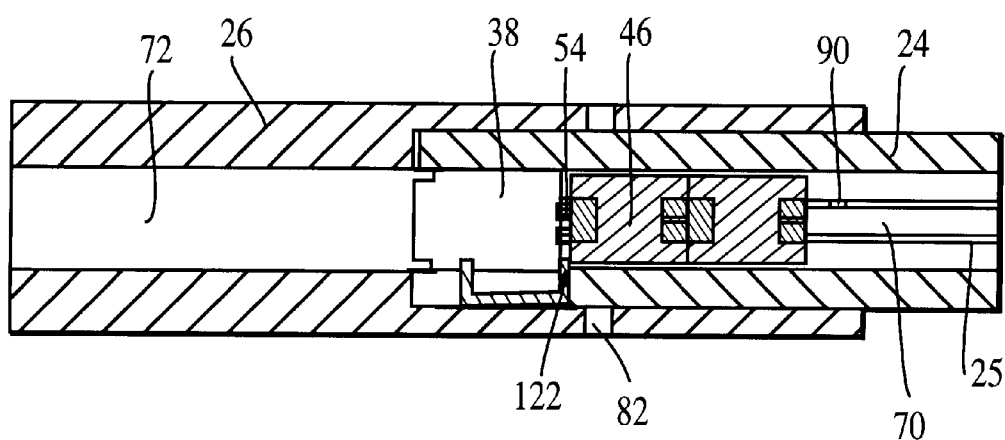

In this case shown in FIG. 24, a non-blank dimer 46 is attempting to act on a blank section of storage tape 28. Since the state protrusion 55 is blank or flat, there is no force to keep discriminator 120 retracted from the path of the non-blank dimer 46, thus the dimer is rejected from the enzyme 22 by the mechanism 122.

Figure 25:
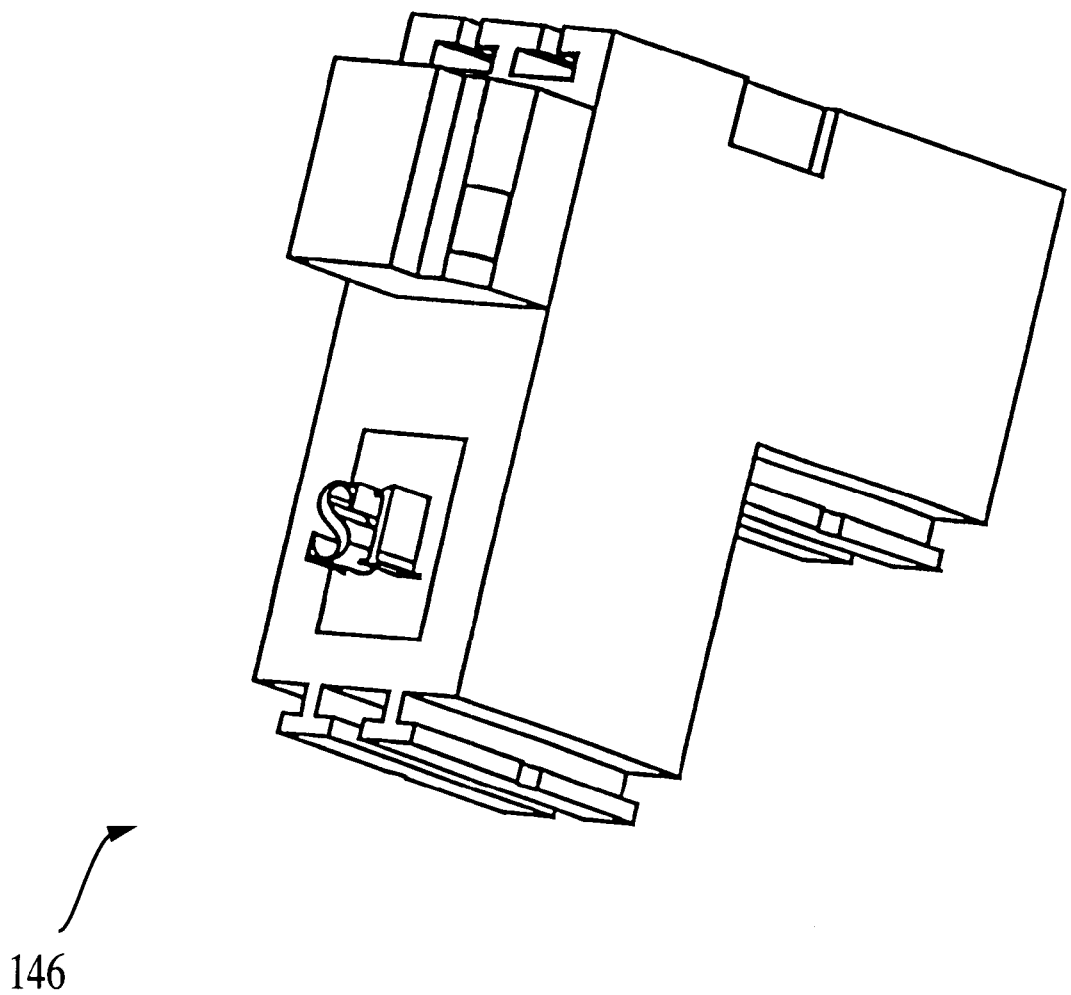

The example in FIGS. 20–24 illustrate the blank state-transition dimer 146 with a tape extension to the right. FIG. 25 illustrates a symmetric extend left blank state-transition dimer 146. Just as the previous example described the end condition, there is a corresponding mechanism for handling the left end condition.

Figure 26:
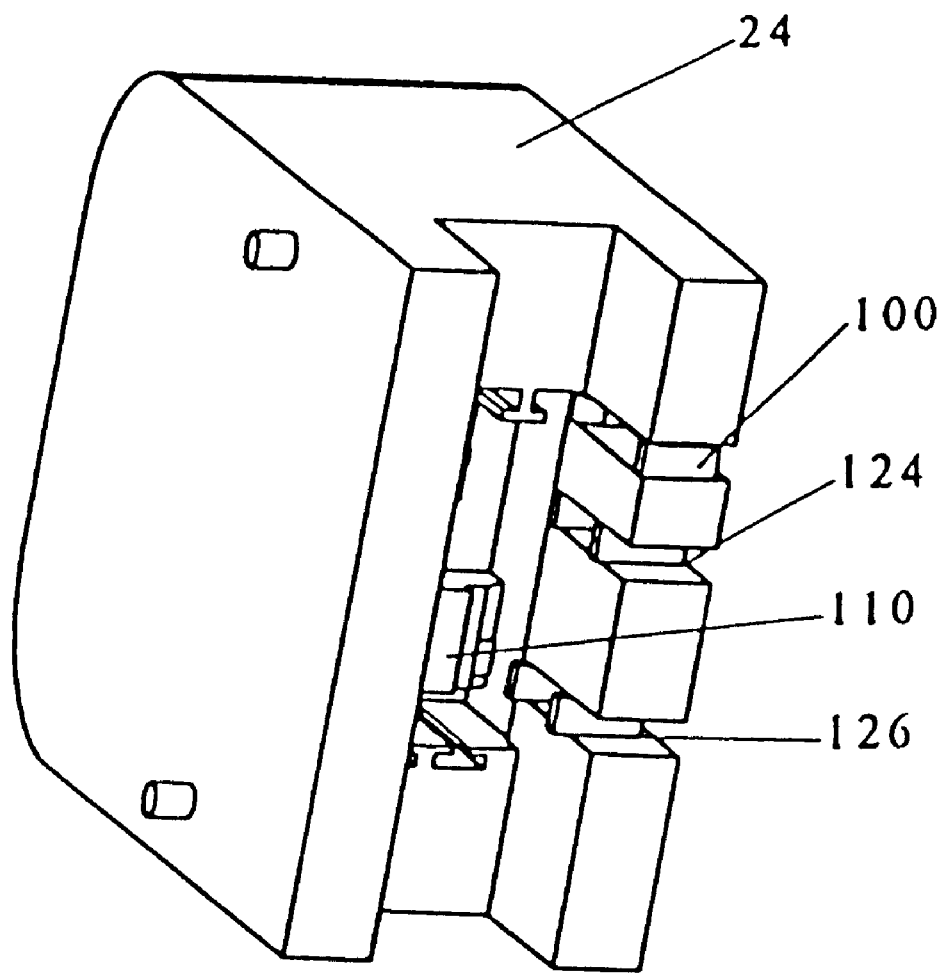

Reference is now made to FIG. 26 which illustrates the right, left and blank discriminator elements of the two section enzyme 24. The two section enzyme 24 comprises a left detector 124, the blank detector 110, and a right detector 126.

Left detector 124 detects and correctly processes tape extensions to the left. Right detector 126 detects and correctly processes tape extension to the right.

Movement

As in previous proposals for computation devices based on random Brownian motion, referenced above, the device described herein is designed to be driven by random movement of its components. The following movements are necessary in order to effect progress of a computation:

- Movement of alphabet monomers 30 and state-transition monomers 40 to form dimers 46.
- Movement of such dimers 46 into the two section enzyme 24.
- Movement of the two section enzyme 24 of the enzyme 22 relative to the three section enzyme 26.
- Movement of the storage tape 28 relative to the enzyme 22.
- Movement of dimers 46 in the two section enzyme 24, pushing out a state-transition monomer 40 and a alphabet monomer 30 through the three section enzyme 26.
- Movement of redundant state-transition monomers 40 and alphabet monomers 30 through the three section enzyme 26.

The machine 20 is designed so that only certain random movements can affect the computation, namely those that correspond to correct transitions of the underlying Turing machine, whereas other random movements do not affect the computation. In particular, random movements of dimers 46 which represent illegal transitions for the Turing machine 20, as well as movement of dimers 46 in case the two section enzyme 24 is not positioned correctly relative to the storage tape 28 and/or relative to the three section enzyme 26, are rejected by the discrimination mechanisms 90, 100 and 120 of the enzyme 22.

The ability of the storage tape 28 to move in the left and right tunnels 74 and 76, respectively, and the ability of the two and three section enzymes, 24 and 26, respectively, of the enzyme 22 to move one unit to the left or to the right relative to each other, is utilized as follows.

Movement of the storage tape 28 is needed to enable the computation to progress in the following cases:

If the current state-transition monomer 40 is a "move left" transition, the monomer 40 is aligned to the left of the three section enzyme 26, and the next transition is also "move left", thus the tape has to move one unit to the right to enable the next transition.

If the current State-transition monomer 40 is a "move right" transition, the monomer 40 is aligned to the right of the three section enzyme 26, and the next transition is also "move right", thus the tape has to move one unit to the left to enable the next transition.

Figure 27:
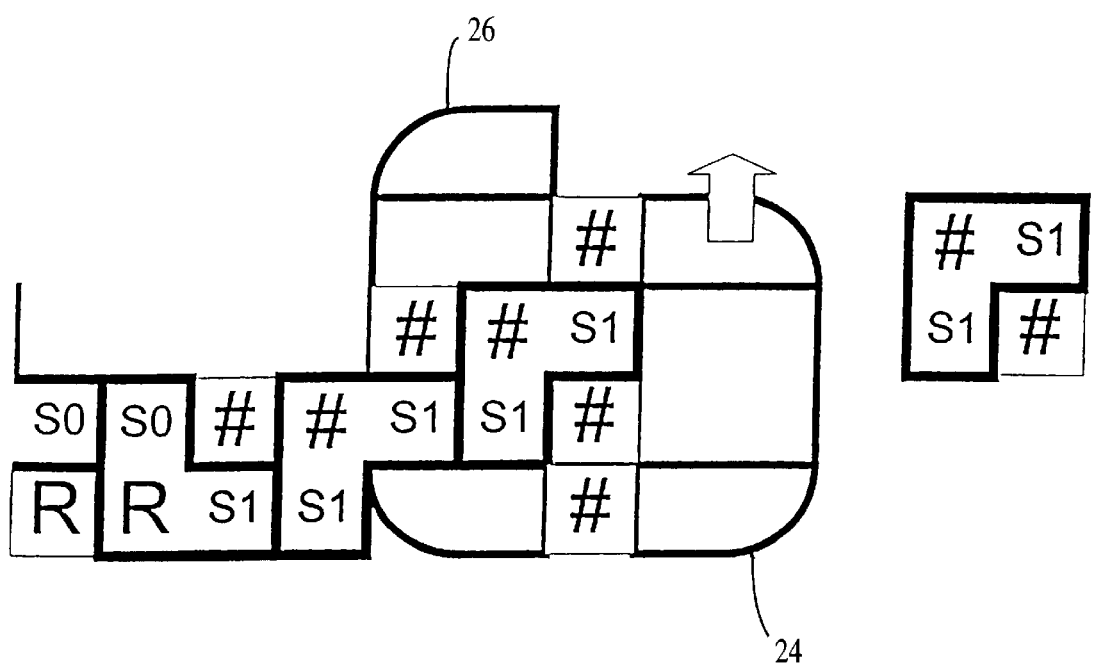
FIG. 27 is an illustration of the two section enzyme relative to the three section enzyme.

Reference is now made to FIG. 27, an illustration of the two section enzyme 24 relative to the three section enzyme 26. Movement of the two section enzyme 24 relative to the three section enzyme 26 is needed to enable the computation to progress in the following cases:

If the two section enzyme 24 is aligned to the left of the three section enzyme 26 and the next transition is "move right", then two and three section enzymes, 24 and 26, respectively, have to move so that the two section enzyme 24 is aligned to the right of the three section enzyme 26.

As an example, in FIG. 27, if the two section enzyme 24 is aligned to the right of the three section enzyme 26 and the next transition is "move left", then two and three section enzymes, 24 and 26, respectively, have to move so that the two section enzyme 24 is aligned to the left of the three section enzyme 26.

Examples of Enzyme 22 Computation

Figure 28:
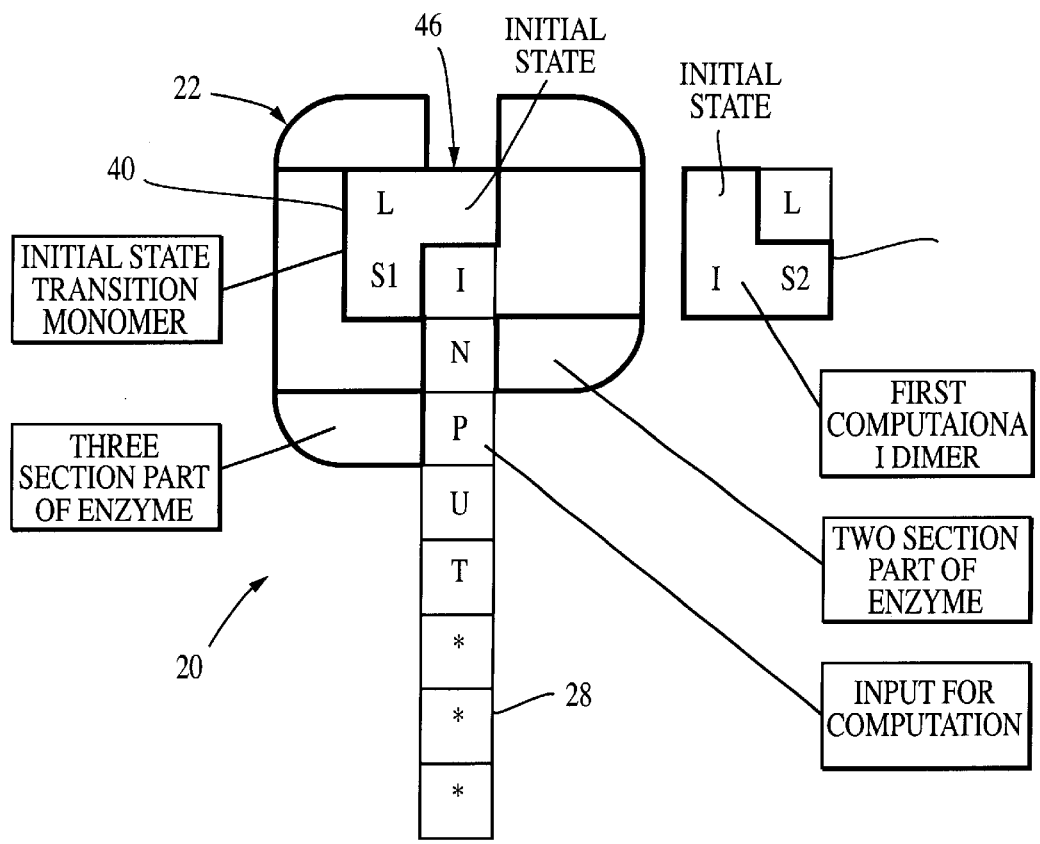
FIG. 28 is a schematic illustration of a computation performed by the Turing machine operative in accordance with a preferred embodiment of the present invention.

Reference is now made to FIG. 28, a schematic illustration of a computation performed by the Turing machine 20.

The computation begins with the enzyme 22 containing a state-transition monomer 40 representing the initial state, attached to the left of a string of tape monomers 30 representing the input of the computation. The computation progresses by a dimer 46, consisting of a state-transition monomer 40 attached to a tape monomer 28 entering the enzyme 22 and displacing the existing state-transition monomer 40 and possibly also its adjacent tape monomer 30.

In the mechanical implementation of this enzyme 22, the physical interaction of state-transition dimers 46, alphabet monomers 30 and the enzyme 22 is facilitated by physical manipulation. Note that while intelligence may be used to speed up processing by selecting the correct dimers, execution of the incorrect dimer 46 cannot proceed, due to the various mechanisms inside the enzyme 22. In the molecular implementation and the physical implementation, processing can occur in an automatic fashion, using Brownian motion or another interactive force or motion. The discrimination mechanisms in the enzymes 22 prevent incorrect execution in the mechanical model and the molecular model. Thus so long as there is system motion, processing will occur and a result can be obtained. The speed of processing depends on many factors, such as but not limited to, density of components, speed of motion, presence of intelligence/guiding force or random motion.

The following examples, FIGS. 29–33, illustrate sample components and a progressive sample calculation. Unlike FIG. 28 which contained a detailed illustration, for purposes of brevity the FIGS. 29–33 do not show the discrimination of incorrect dimer 46 to system state matching, nor do they show that in a false state how Brownian or other motion can rectify the false state, nor do they show irrelevant Brownian movements.

Consider the problem to determine whether an expression consisting of left and right parenthesis is balanced. For examples, ( ), (( )), ((( )( ))) are all balanced expressions, whereas (( )( ))) is not.

Reference is now made to FIG. 29, a sample expression ( ) represented as alphabet monomers 30, and specifically a left parenthesis is represented with the letter 'L' and a right parenthesis is represented with the letter 'R'.

Figure 1:
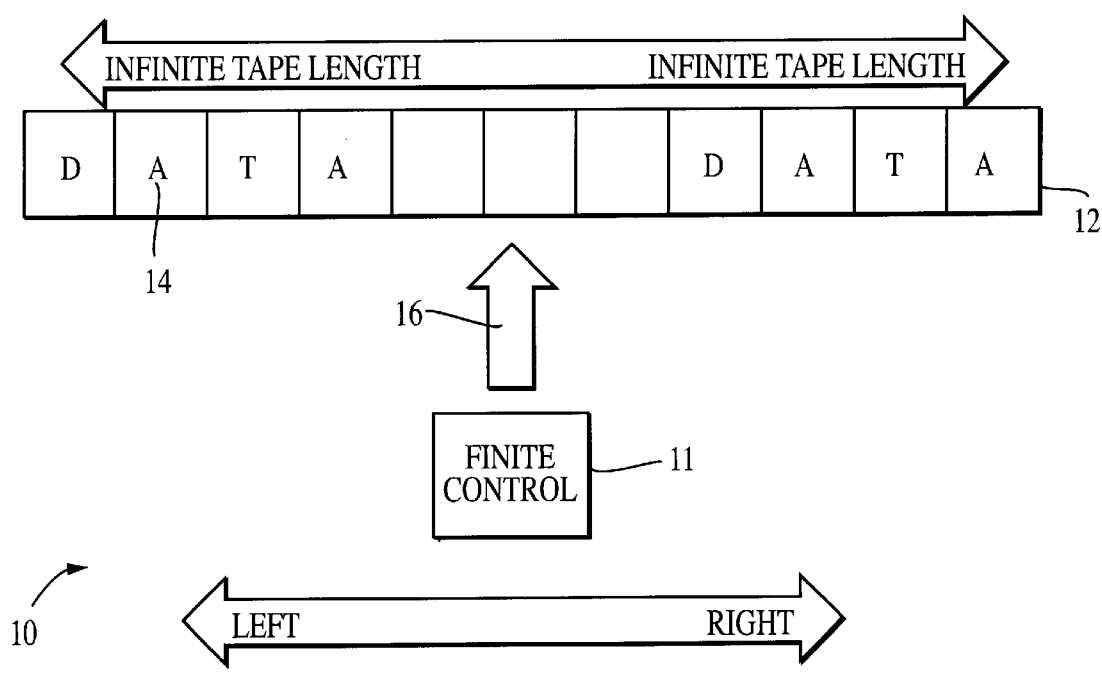
FIG. 1 is a schematic illustration of a prior art Turing machine.

Reference is now made to FIGS. 30 A–H, an illustration of a table of valid state-transition dimers 40. Using a schematic similar to the quintuples described hereinabove in reference to FIG. 1, the system testing for balanced expressions has 4 states, represented by S0, S1, S2, and S3. 'b' is an element that senses the end of tape condition, and '#' is an alphabet monomer used for processing.

If the original string is balanced then the storage tape 28 will consist entirely of '#' elements and end in the accepting state S2. If there are is an excess of 'R' type elements then the system halts in state S1. If there an excess of 'L' type elements the system halts in a state S3. It is assumed that the system always starts at the left end in state S0

Examples of Unbalanced Strings

Figure 31A:
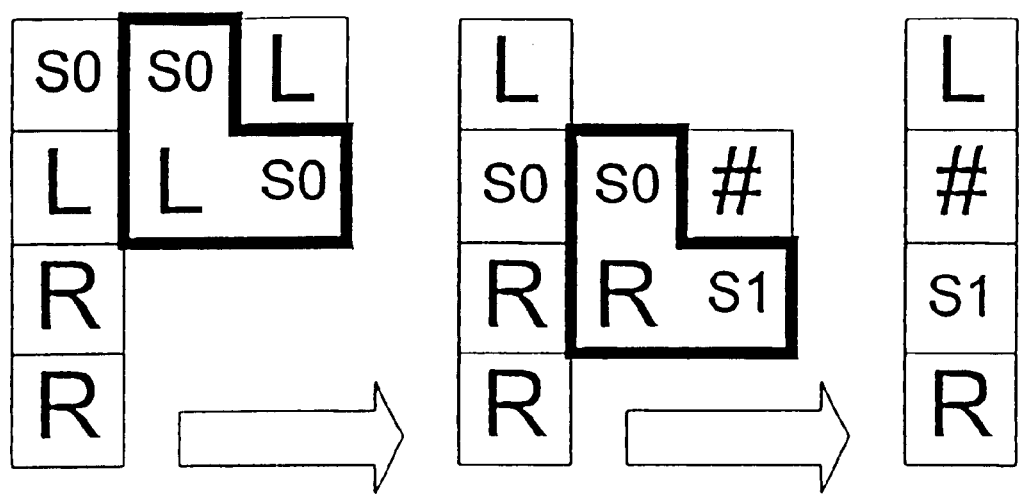
FIGS. 31a–31e, sometimes referred to collectively as FIG. 31, are further schematic illustrations of sample calculations in accordance with a preferred embodiment of the present invention.

Reference is now made to FIGS. 31A–E, the first example of an unbalanced string and consists of the expression LRR. As illustrated in FIG. 31A, the initial system tape of S0, L, R, R is processed by <S0, L, S0, right> This results in a tape state of L, S0, R, R which is processed by <S0, R, S1, #, right> This results in a tape state of L, #, S1, R.

Figure 31B:
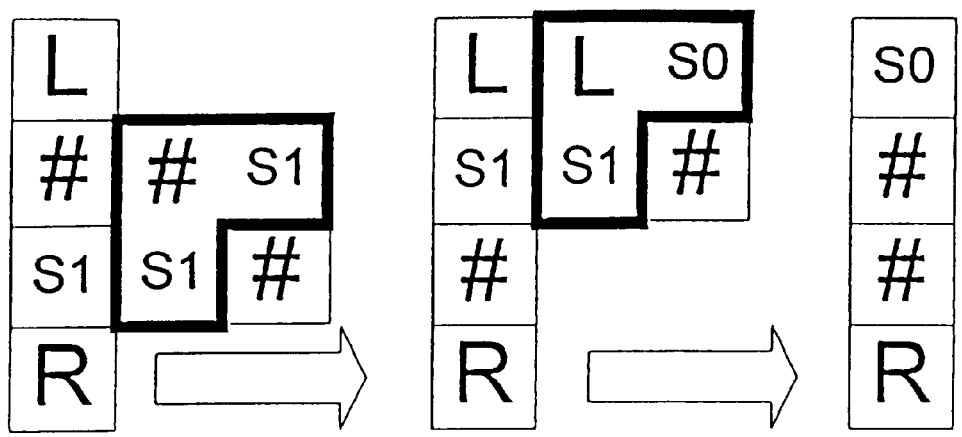

Reference is now made to FIG. 31B, the result from the previous actions yielded a tape state of L, #, S1, R. This result is processed by <S1, #, S1, #, left>. This results in a tape state of L, S1, #, R which is processed by <S1, L, S0, #, left>. This results in a tape state of S0, #, #, R.

Figure 31C:
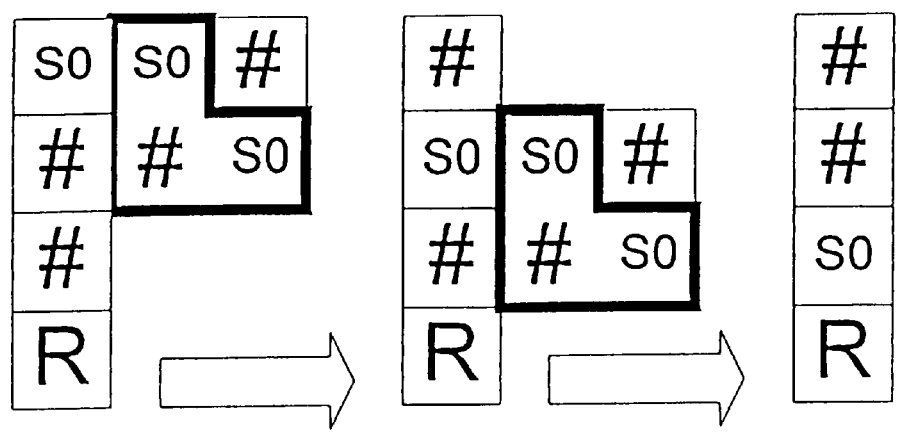

Reference is now made to FIG. 31C, the result from the previous actions yielded a tape state of S0, #, #, R. This result is processed by <S0, #, S0, #, right>. This results in a tape state of #, S0, #, R which is processed by <S0, #, S0, #, right> This results in a tape state of #, #, S0, R.

Figure 31D:
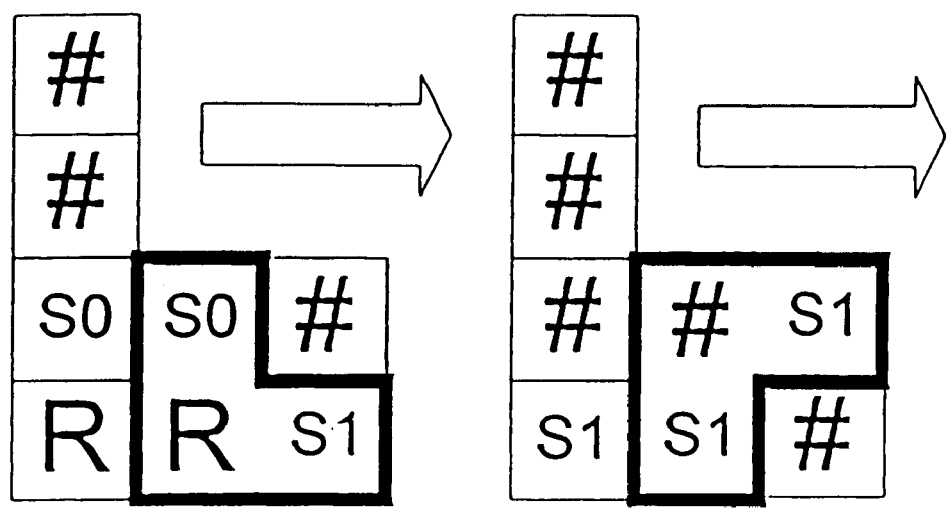

Reference is now made to FIG. 31D, the result from the previous actions yielded a tape state of #, #, S0, R. This result is processed by <S0, R, S1, #, right>. This results in a tape state of #, #, #, S1 which is processed by S1, #, S1, #, left>. This results in a tape state of #, #, S1, #.

Figure 31E:
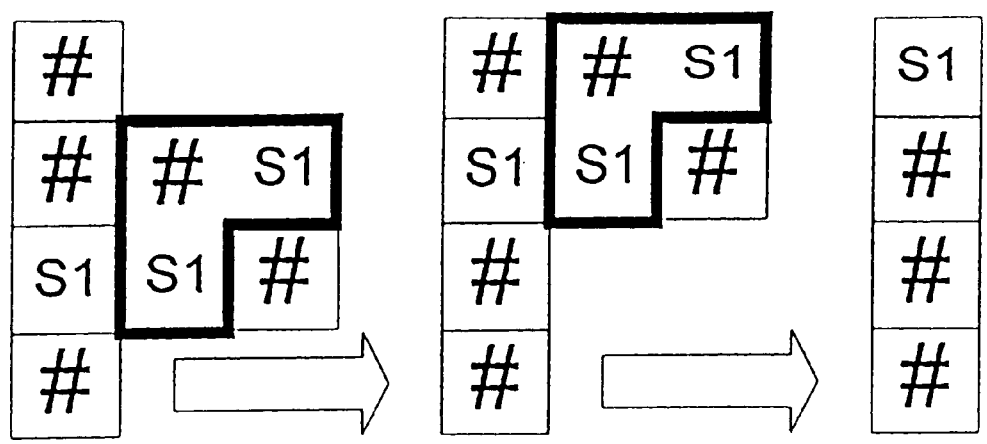
Figure 32A:
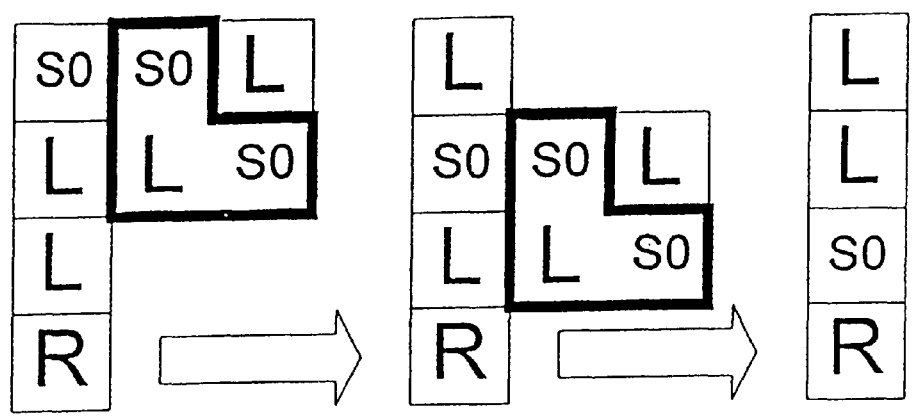
FIGS. 32a–32f, sometimes referred to collectively as FIG. 32, are further schematic illustrations of sample calculations in accordance with a preferred embodiment of the present invention.
Figure 32B:
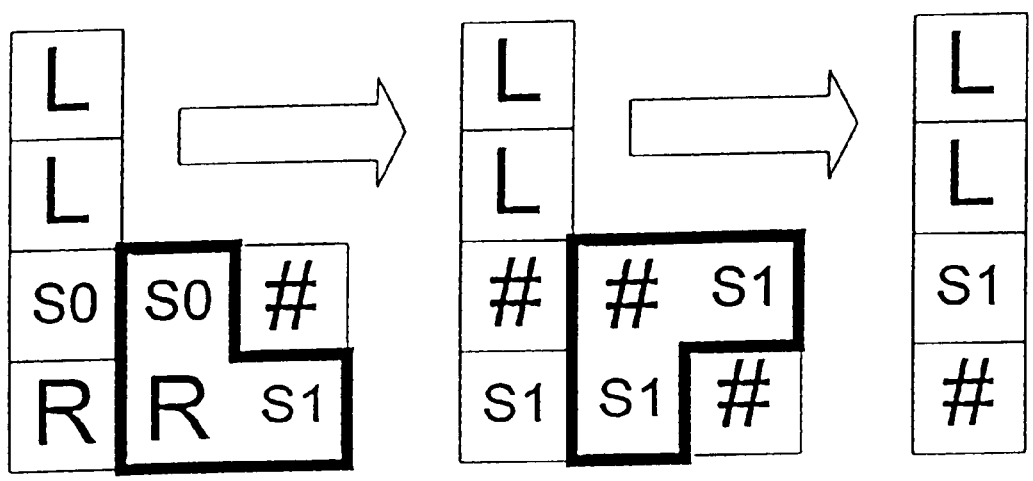
Figure 32C:
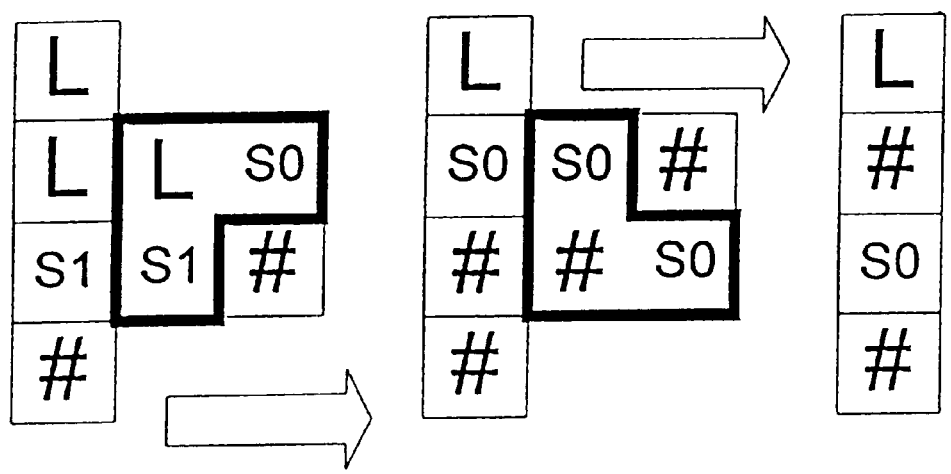
Figure 32D:
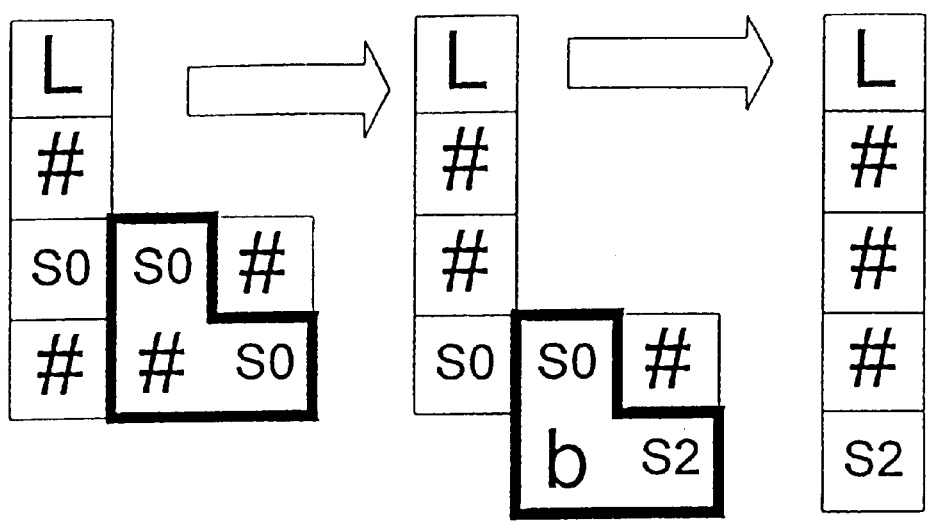
Figure 32E:
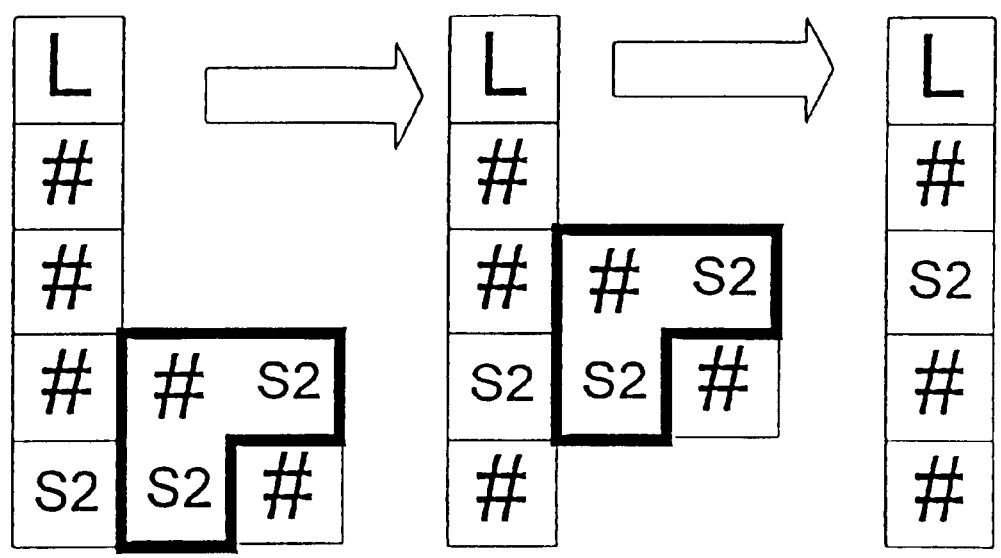
Figure 32F:
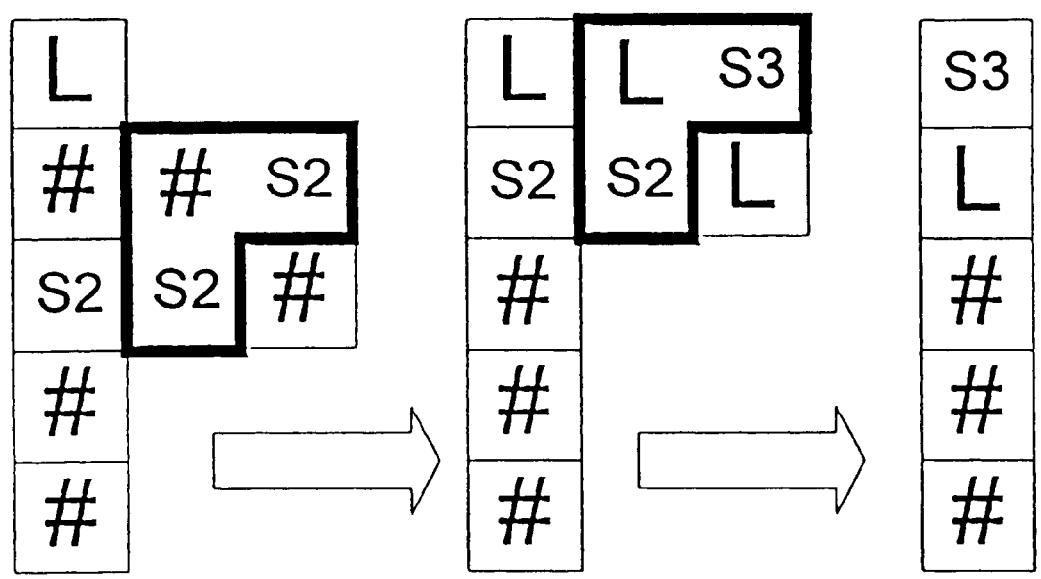
Figure 33A:
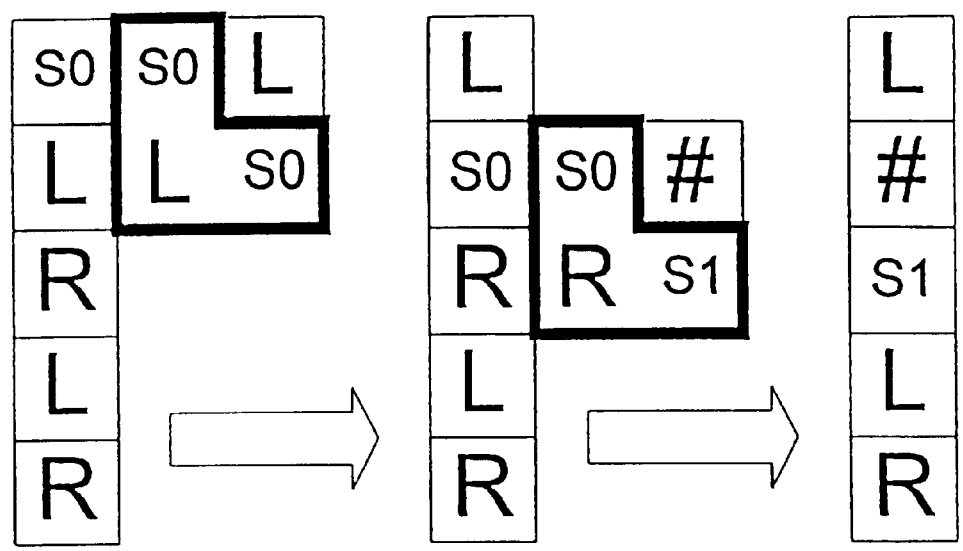
FIGS. 33a–33i, sometimes referred to collectively as FIG. 33, are further schematic illustrations of sample calculations in accordance with a preferred embodiment of the present invention.
Figure 33B:
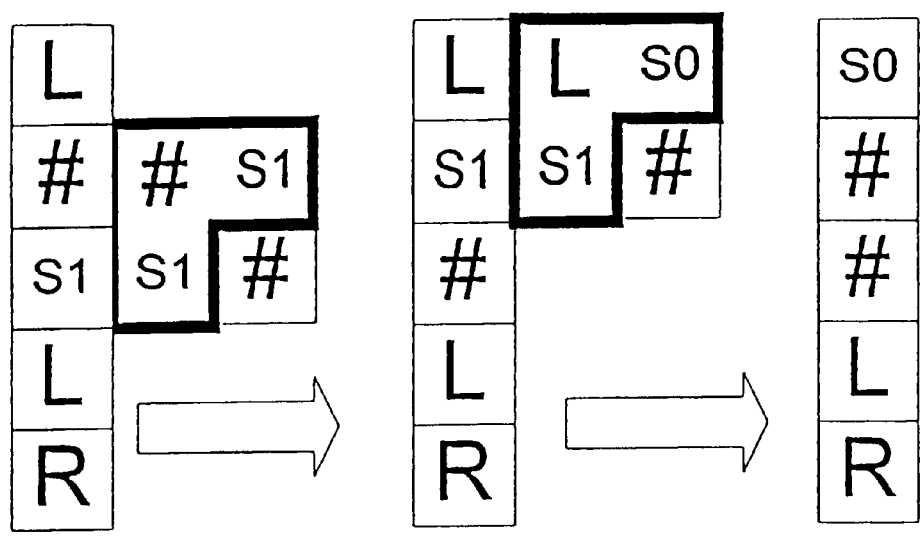
Figure 33C:
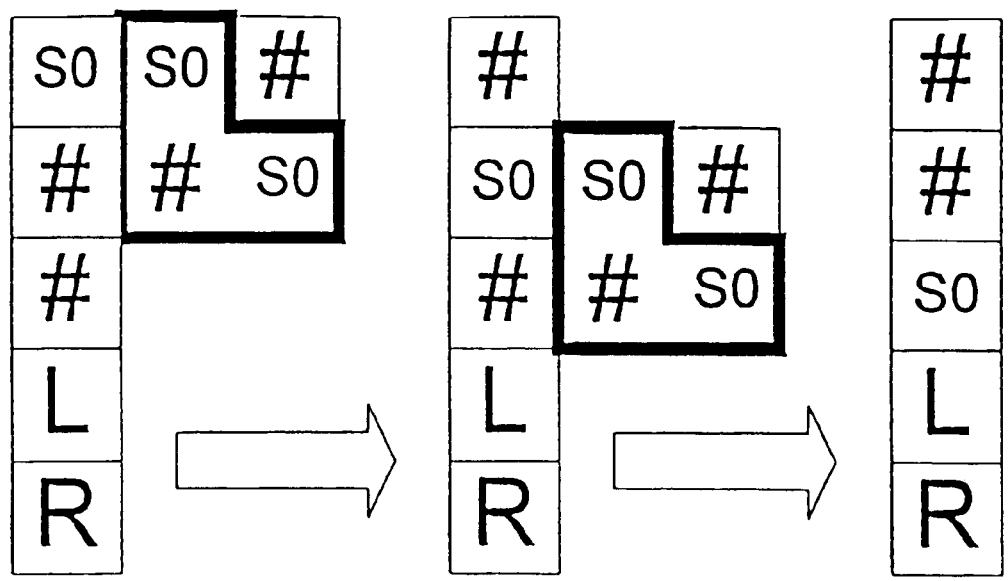
Figure 33D:
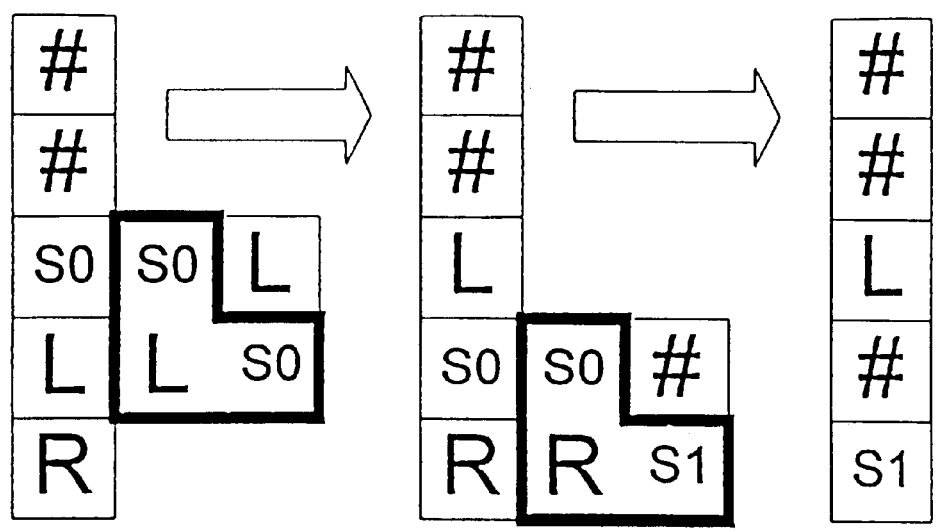
Figure 33E:
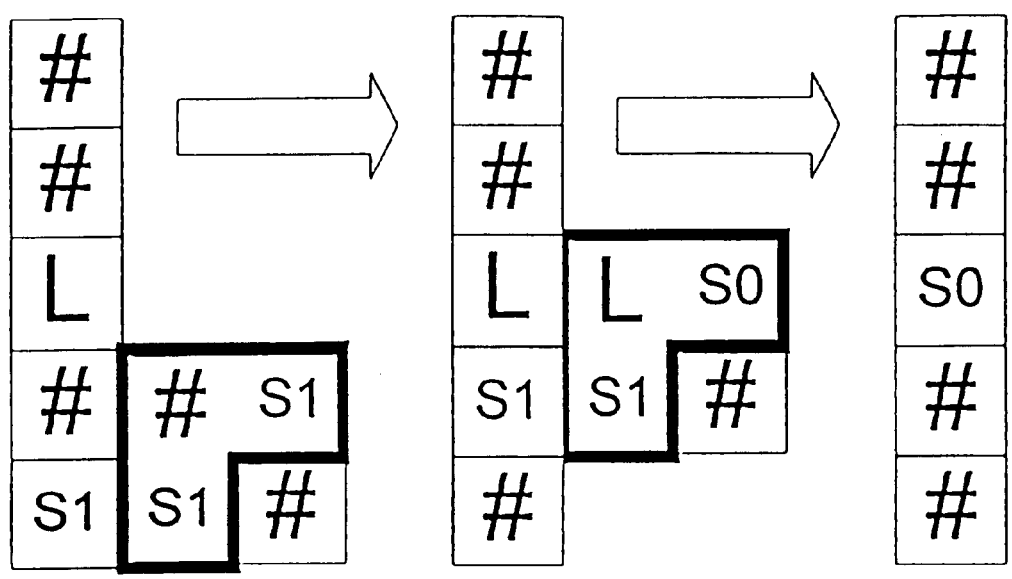
Figure 33F:
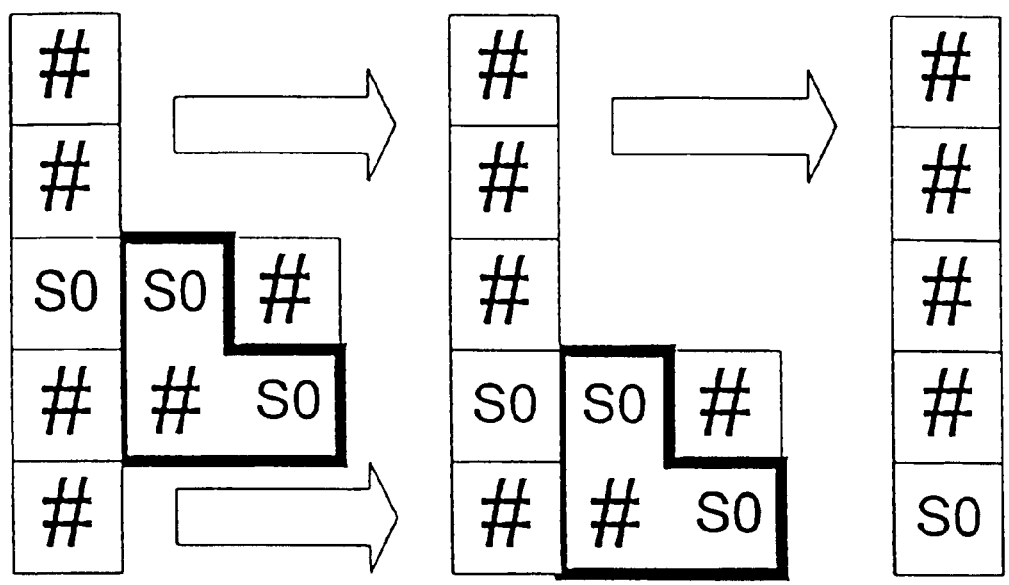
Figure 33G:
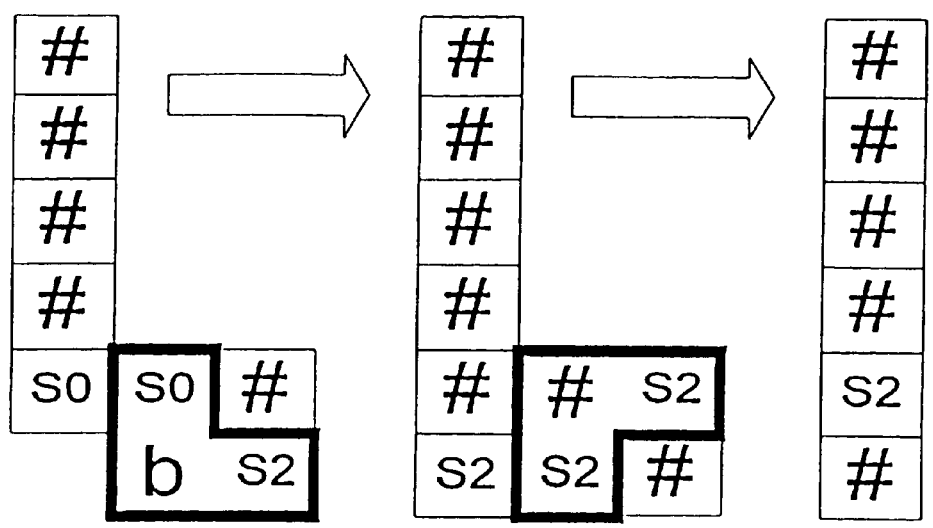
Figure 33H:
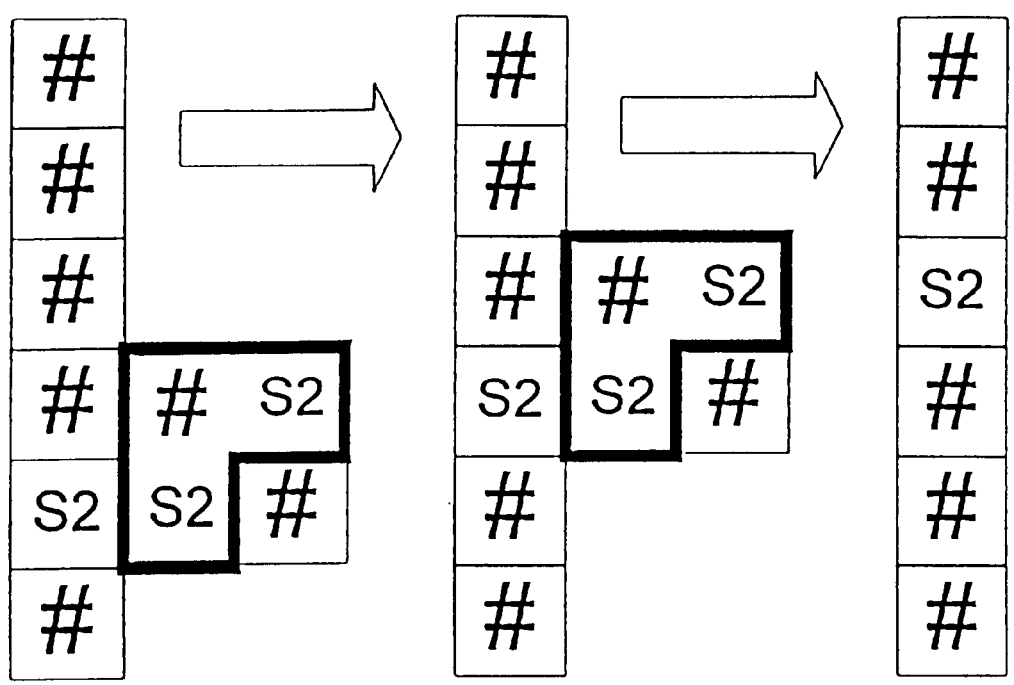
Figure 33I:
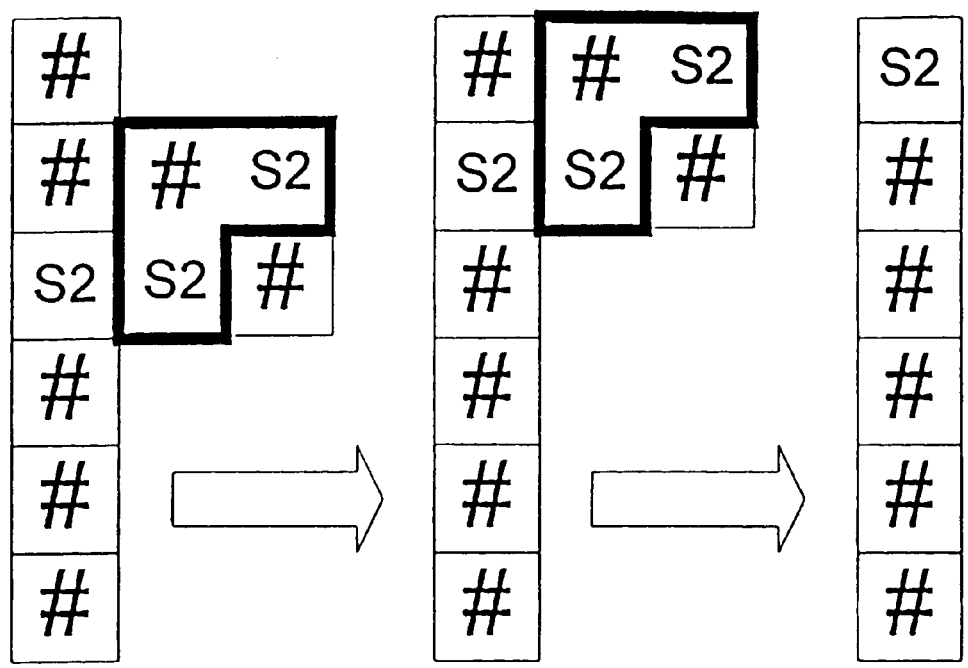

Reference is now made to FIG. 31E, the result from the previous actions yielded a tape state of #, #, S1, #. This result is processed by <S1, #, S1, #, left>. This results in a tape state of #, S1, #, # which is processed by <S1, #, S1, #, left > This results in a tape state of S1, #, #, #. The system halts in state S1, successfully detecting that the input tape consists of an unbalanced expression with an excess of 'R' characters.

Reference is now made to FIGS. 32 A–F, a second example of unbalanced string and consists of the expression LLR. Here the system halts in state S3, successfully detecting that the input tape consists of an unbalanced expression with an excess of 'L' characters.

Reference is now made to FIGS. 33 A–I, an example of a balanced string and consists of the expression LRLR. The system is now in a final accepting state. The output consists entirely of the element "#", the final system state is S2. The system successfully detected that the input tape is balanced.

Example Calculation

Figure 34:
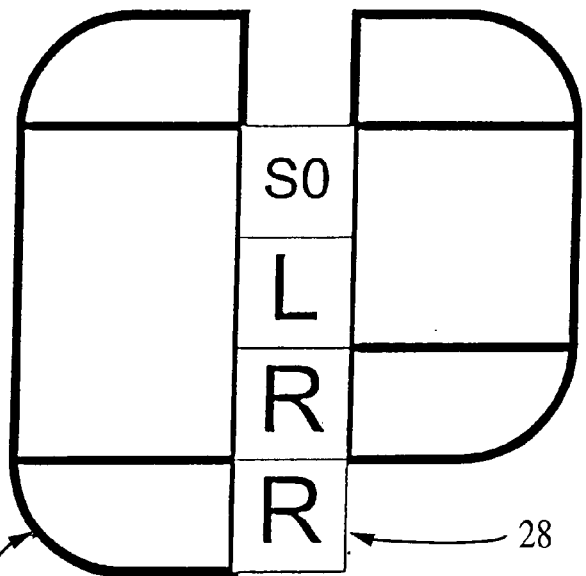
FIGS. 34–89 are additional schematic illustrations of sample calculations in accordance with a preferred embodiment of the present invention.

Reference is now made to FIGS. 34–89, an illustrated series of an example Turing machine 20 calculation, operative in accordance with a preferred embodiment of the present invention.

Figure 35:
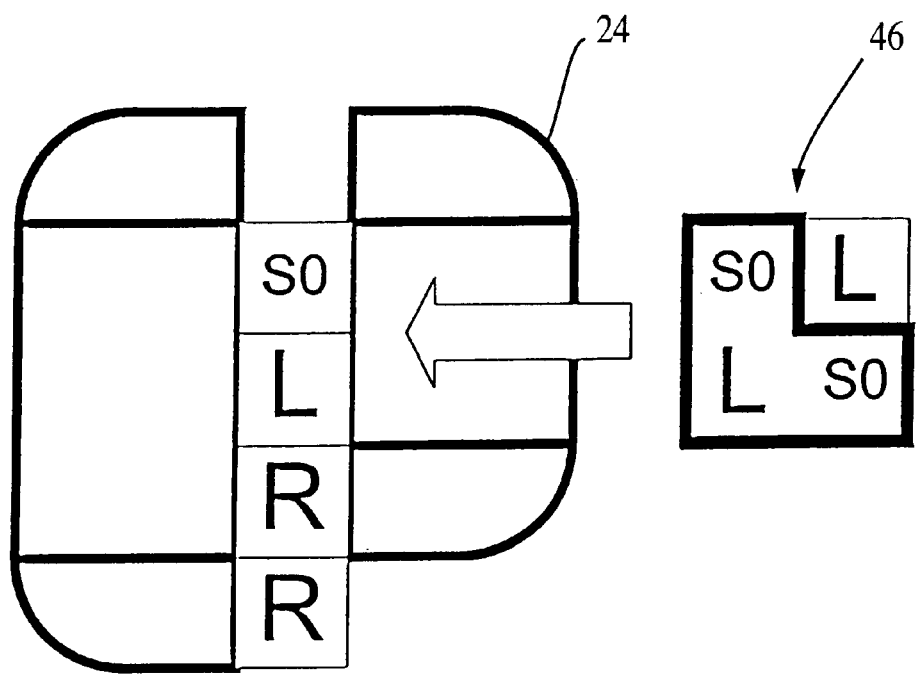
Figure 36:
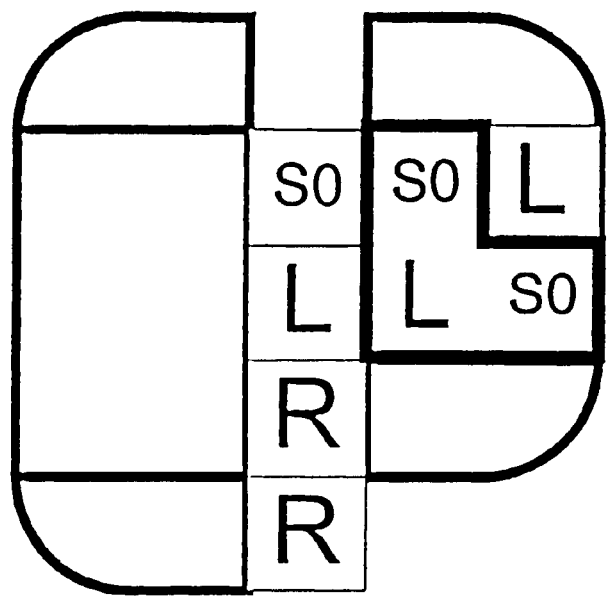

In FIG. 34 the system is in its initial state, an input storage tape 28 of initial state S0,L,R,R is present in the enzyme 22. The matching state-transition dimer 46<S0, L, S0, L, right> of FIG. 35 presents itself to the two section enzyme 24, then in FIG. 36, the dimer 46<S0, L, S0, L, right> successfully mates with the storage tape 28.

Figure 37:
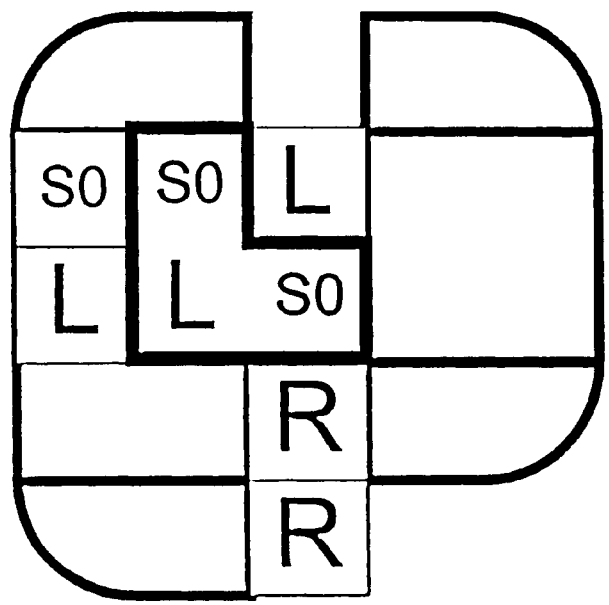
Figure 38:
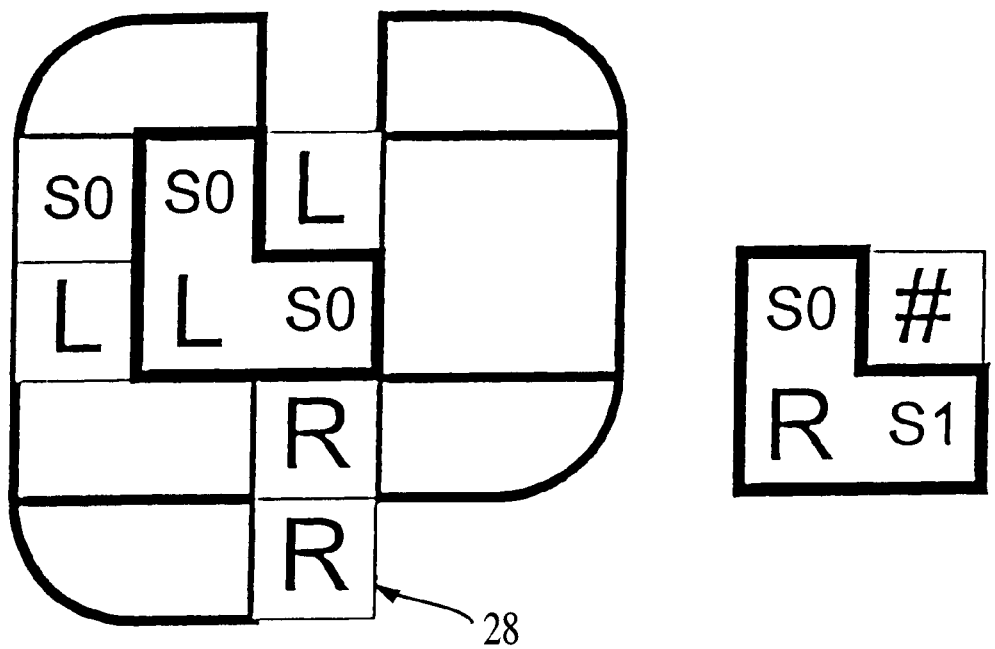

As shown in FIG. 37 the dimer 46<S0, L, S0, L, right> successfully 'processes' the storage tape 28, changes its state, and moves the read/write head 16 one step right in the process. In FIG. 38 dimer 46<S0, R, S, #, right> presents itself, however the enzyme 22 is incorrectly formatted to accept this.

Figure 39:
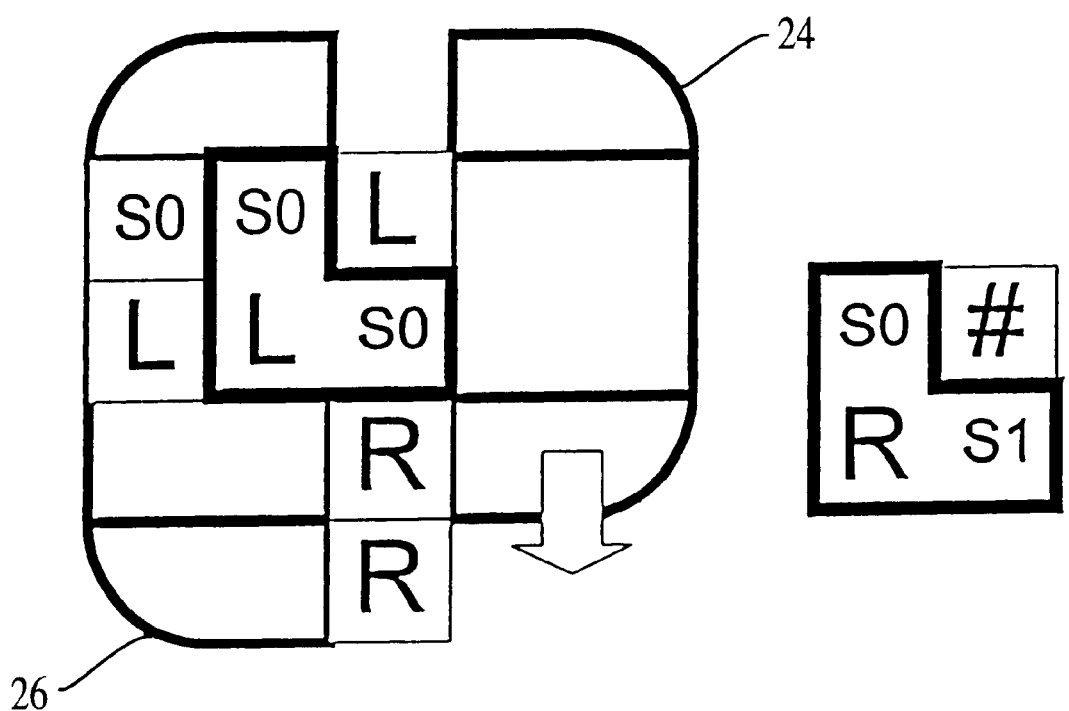

Through Brownian motion or other means, as shown in FIG. 39, the enzyme 22 reconfigures such that the two section enzyme 24 moves relative to the three section enzyme 26 and the storage tape 28.

Figure 40:
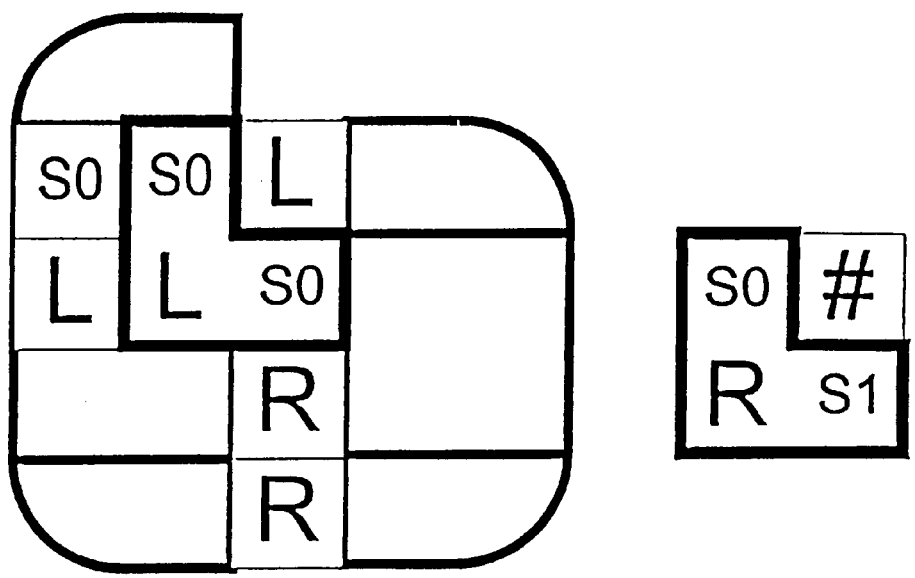

FIG. 40 shows that the enzyme 22 is correctly formatted to process the approaching dimer 46. It should be noted, that in a process not described herein, the enzyme 22 may have reformatted while the dimer 46 was inside the two section enzyme 24. It is additionally important to note that essentially at some point the enzyme 22 reformats itself either through sensing the incompatibility of the approaching dimer 46 or through random process.

Furthermore noted herein is that part of this sensing and random process is the compatibility discrimination characteristics of the enzyme itself, where it only processes dimers 46 that are compatible with the storage tape 28 and the current system state.

Figure 41:
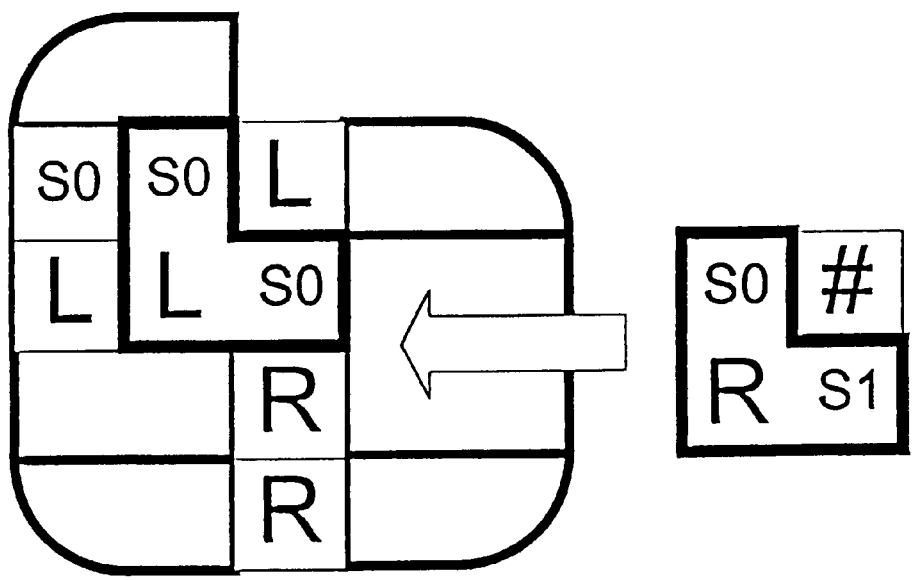
Figure 42:
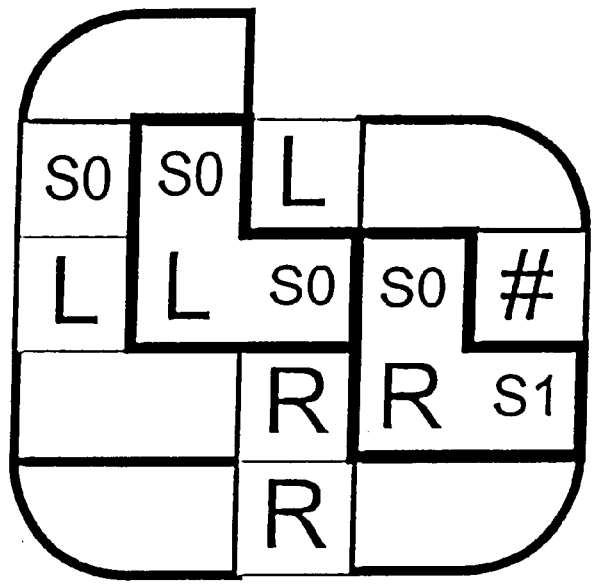
Figure 43:
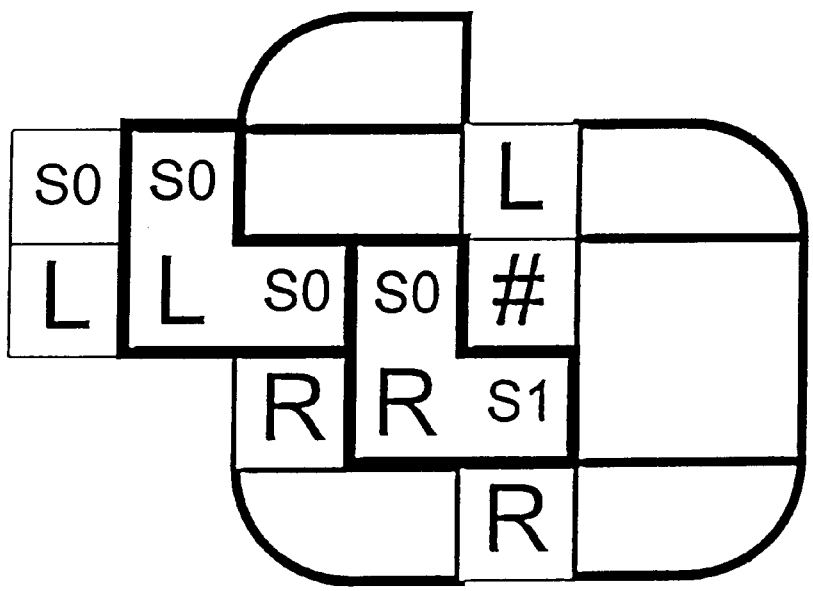

As shown in FIG. 41, the enzyme 22 is correctly formatted, and the dimer 46 approaches the two section enzyme 24, and from there passes into the body. In FIG. 42 the dimer 46 has successfully meshed with the storage tape 28 having passed all of the enzyme discrimination mechanisms. The dimer 46 in FIG. 43 has processed the storage tape 28, displaced the 'R' element, replaced it with a '#' element, moved the storage tape 28 read/write head 16 to the right and changed the system state to that of 'S1'.

Figure 44:
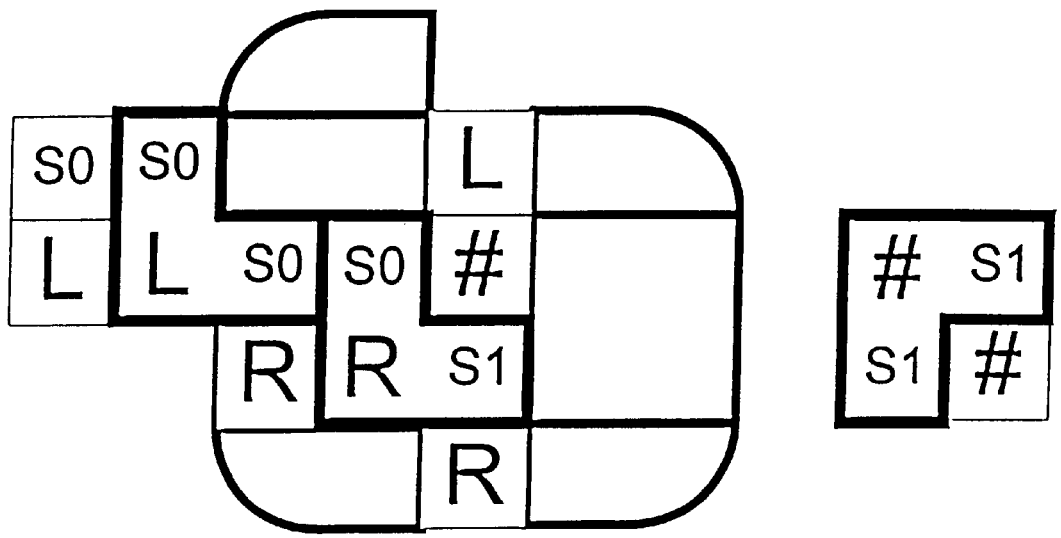
Figure 45:
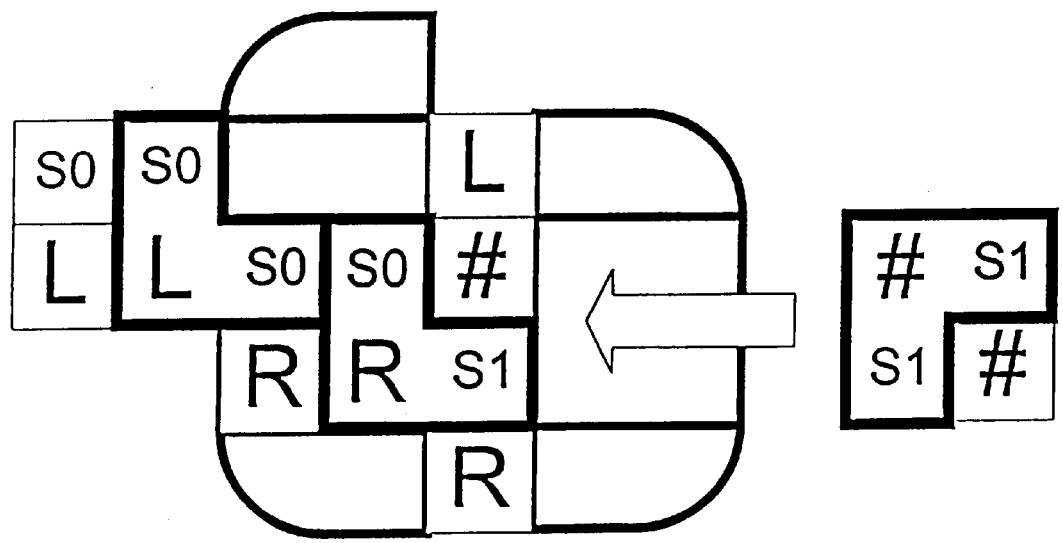

In FIG. 44 the dimer 46<S1, #, S1, #, left> presents itself, in this case the enzyme 22 is correctly formatted to accept this dimer 46. FIG. 45 shows dimer 46 entering the two section enzyme 24.

Figure 46:
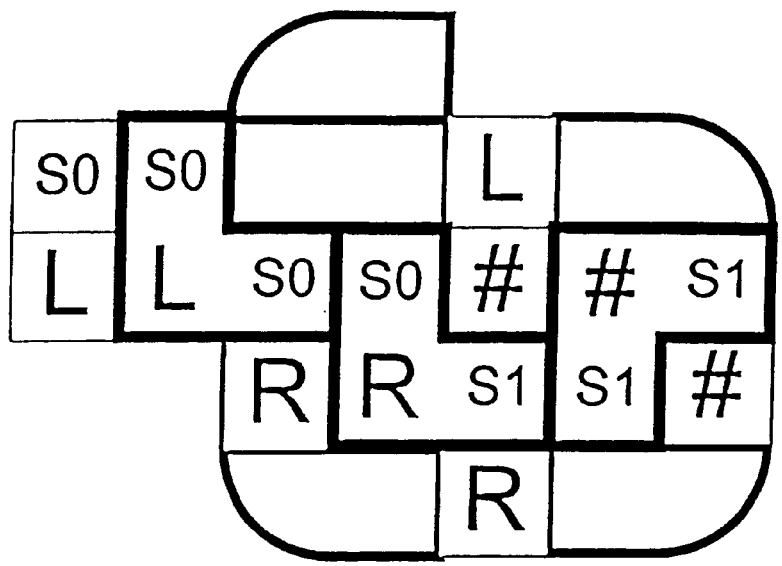
Figure 47:
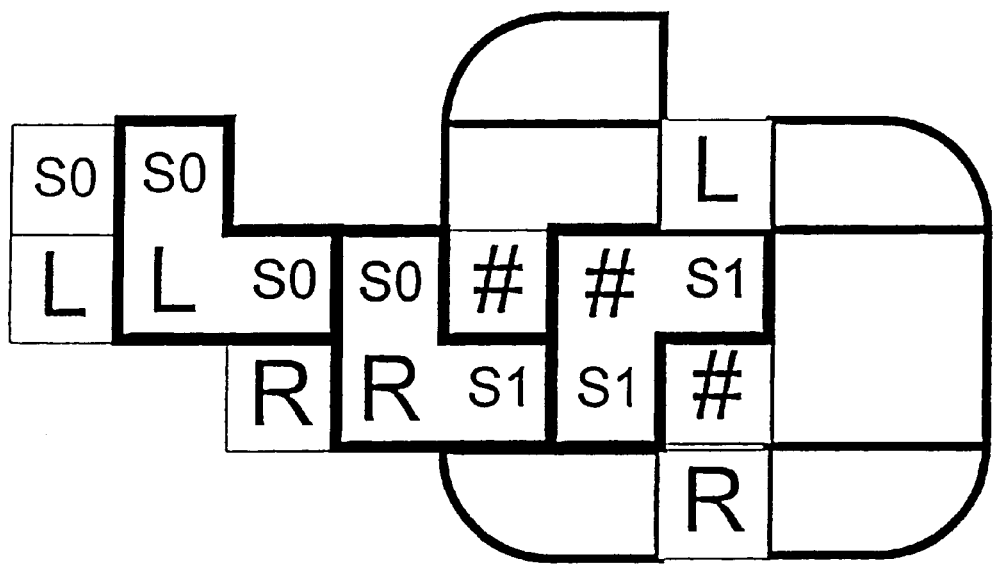

The dimer 46 of FIG. 46 has successfully meshed with the storage tape 28 having passed all of the enzyme discrimination mechanisms. In FIG. 47 the dimer 46 has processed the storage tape 28, displaced the '#' element, replaced it with a '#' element, moved the storage tape 28 read/write head 16 to the left and changed the system state to that of 'S1'.

Figure 48:
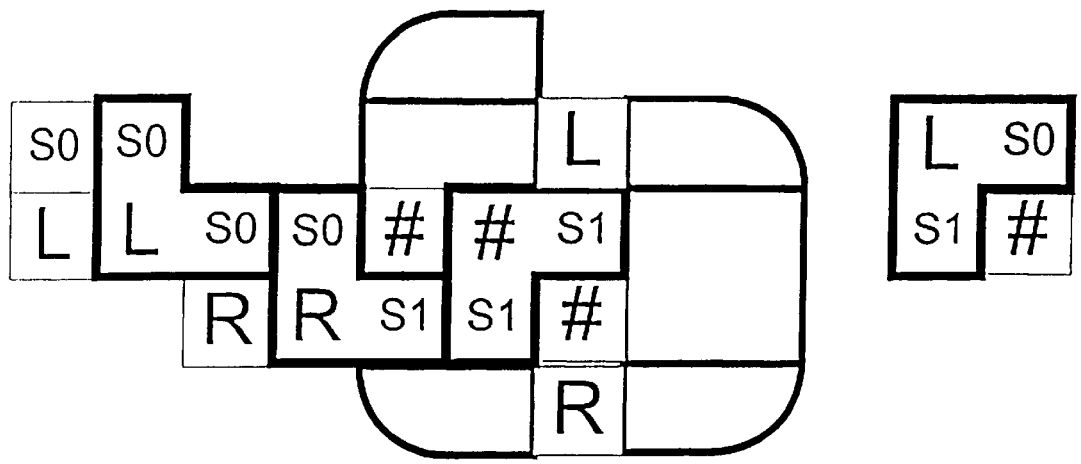
Figure 49:
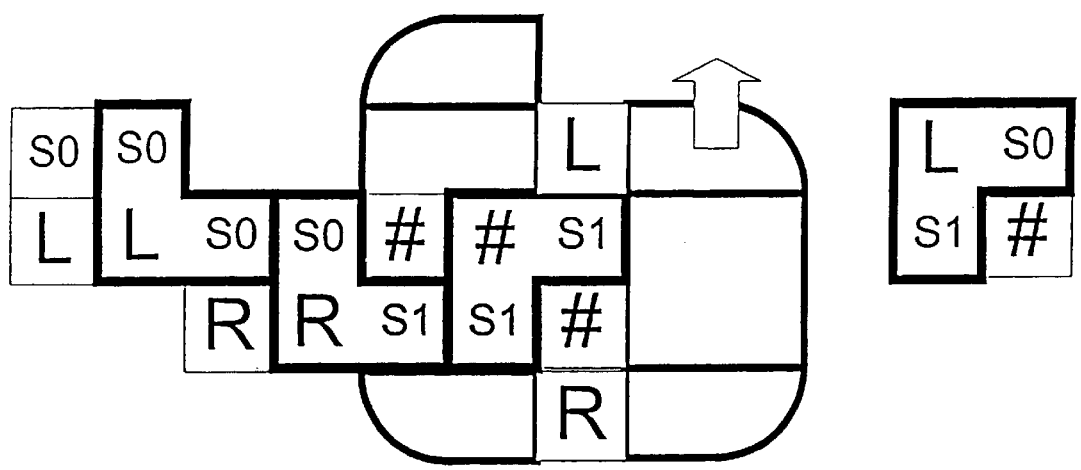

The dimer 46<S1, L, S0, #, left> of FIG. 48 presents itself, however the enzyme 22 is incorrectly formatted to accept it. In FIG. 49, through Brownian motion or other means, the enzyme 22 reconfigures such that the two section enzyme 24 moves relative to the three section enzyme 26 and the storage tape 28.

Figure 50:
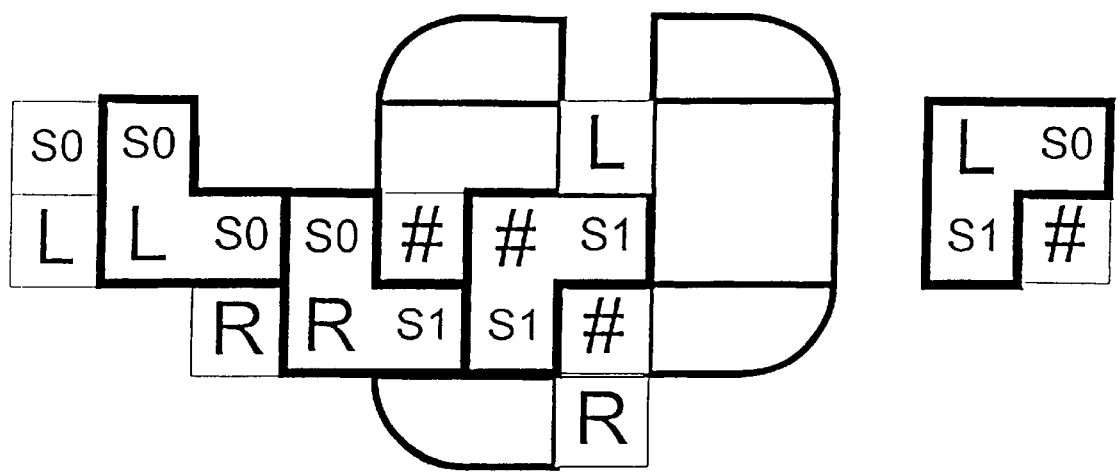
Figure 51:
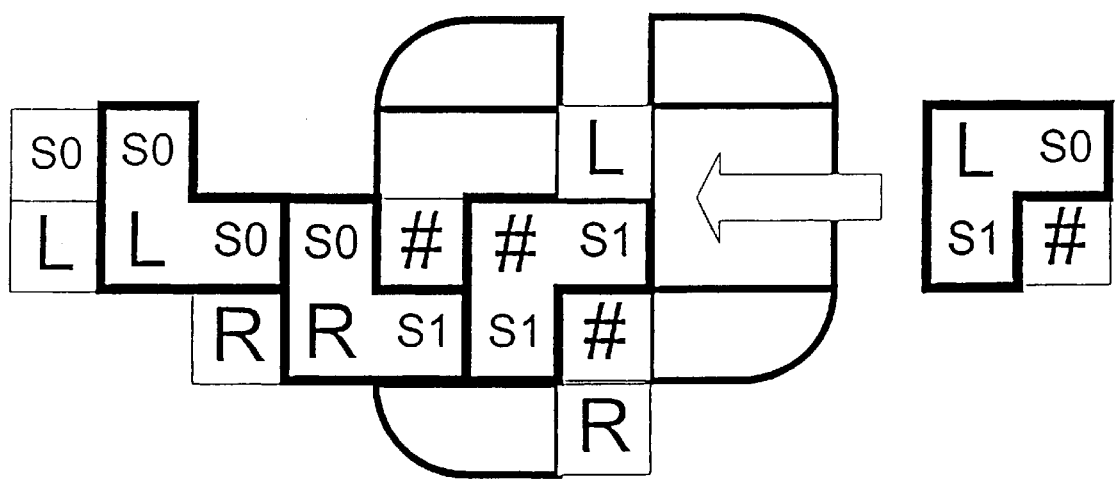

The enzyme 22 of FIG. 50 is now formatted correctly to process the approaching dimer 46. In FIG. 51 the dimer enters the two section enzyme 24

Figure 52:
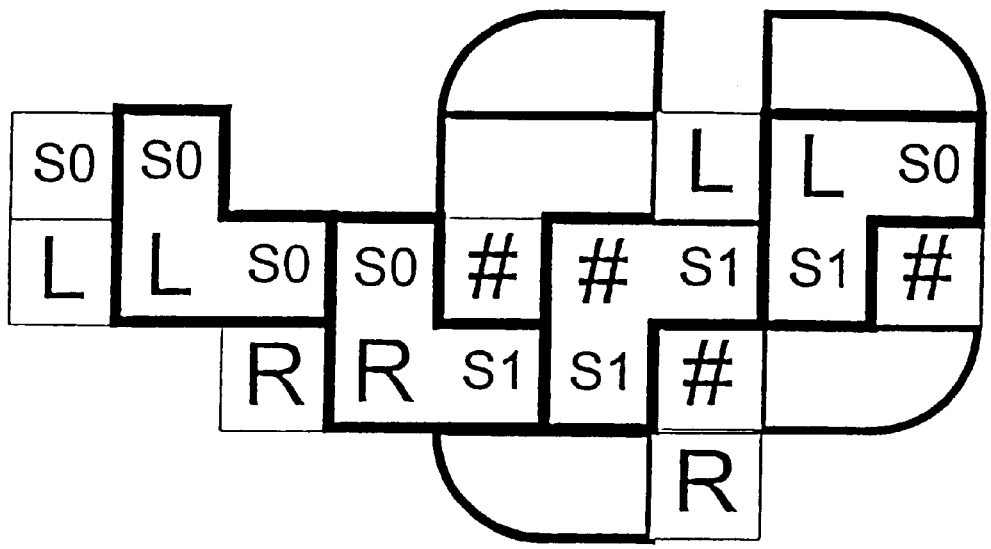
Figure 53:
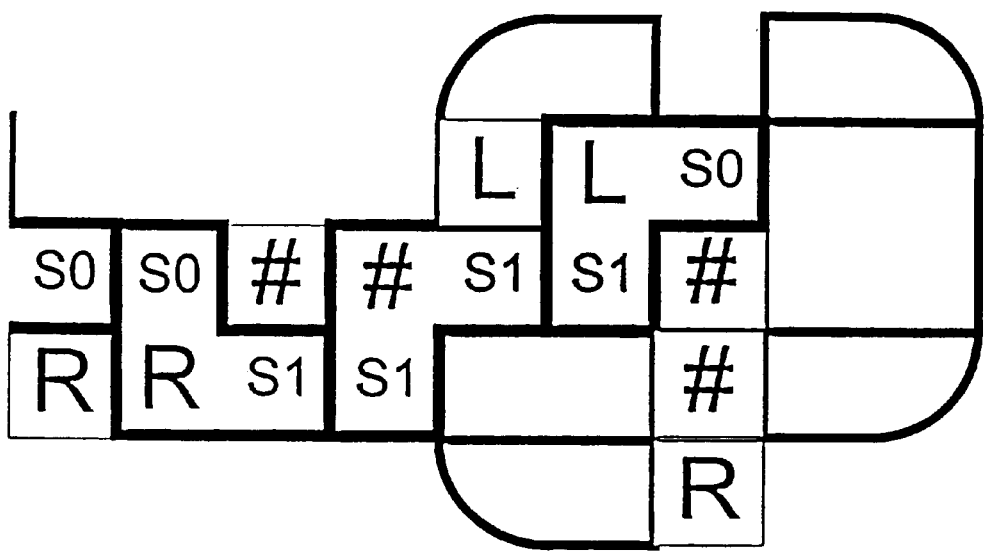

FIG. 52 shows that the dimer 46 has successfully meshed with the storage tape 28, having passed all of the enzyme discrimination mechanisms. In FIG. 53 the dimer 46 has processed the storage tape 28, displaced the 'L' element, replaced it with a '#' element, moved the storage tape 28 read/write head 16 to the left and changed the system state to that of 'S0'.

Figure 54:
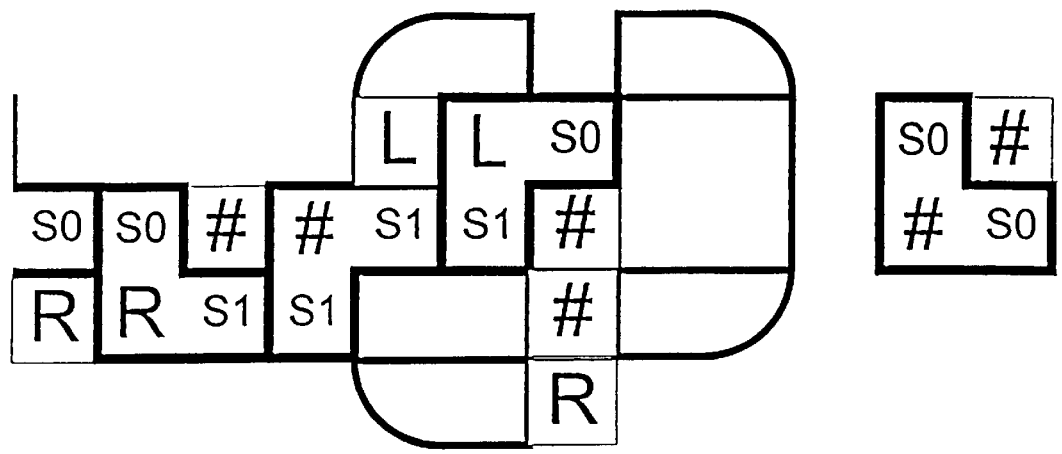
Figure 55:
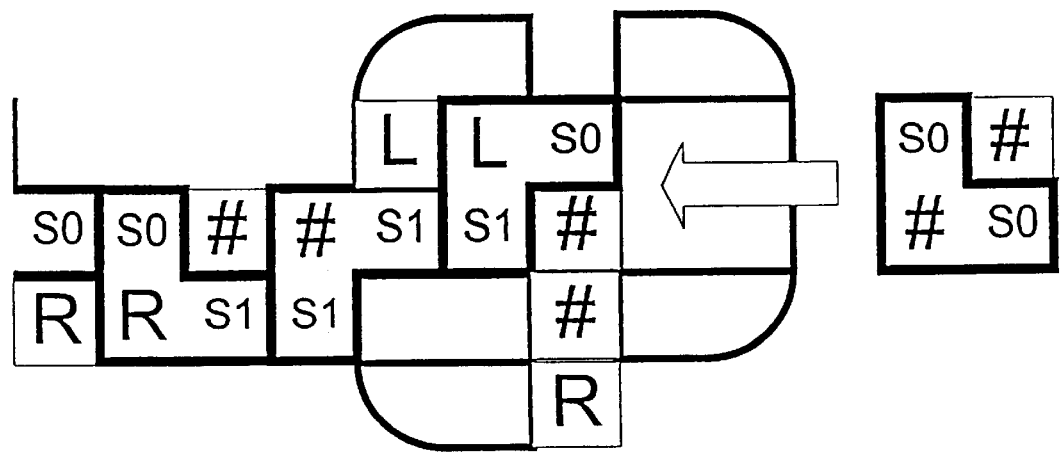
Figure 56:
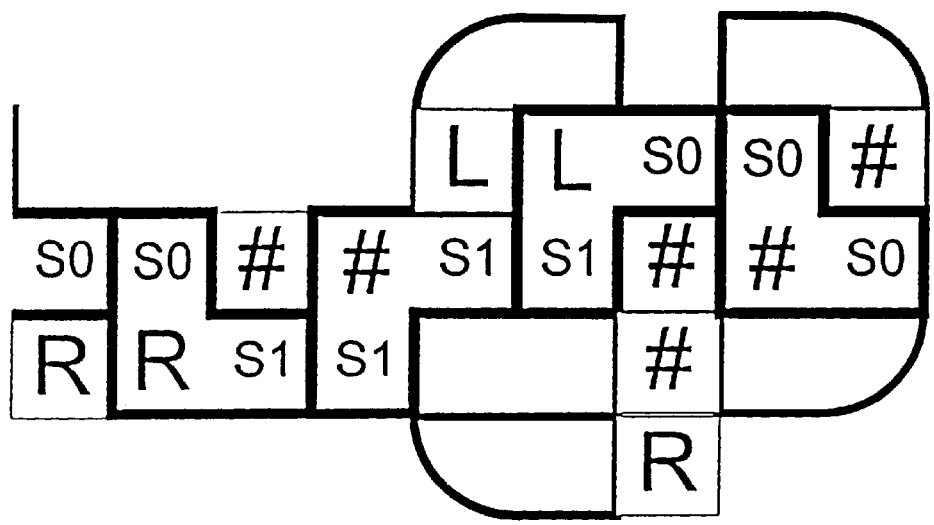

The dimer 46<S0, #, S0, #, right> of FIG. 54 presents itself, in this case the enzyme 22 is correctly formatted to accept this dimer 46. In FIG. 55 the dimer 46 enters the two section enzyme 24. FIG. 56 shows the dimer 46 successfully meshed with the storage tape 28, having passed all of the enzyme discrimination mechanisms.

Figure 57:
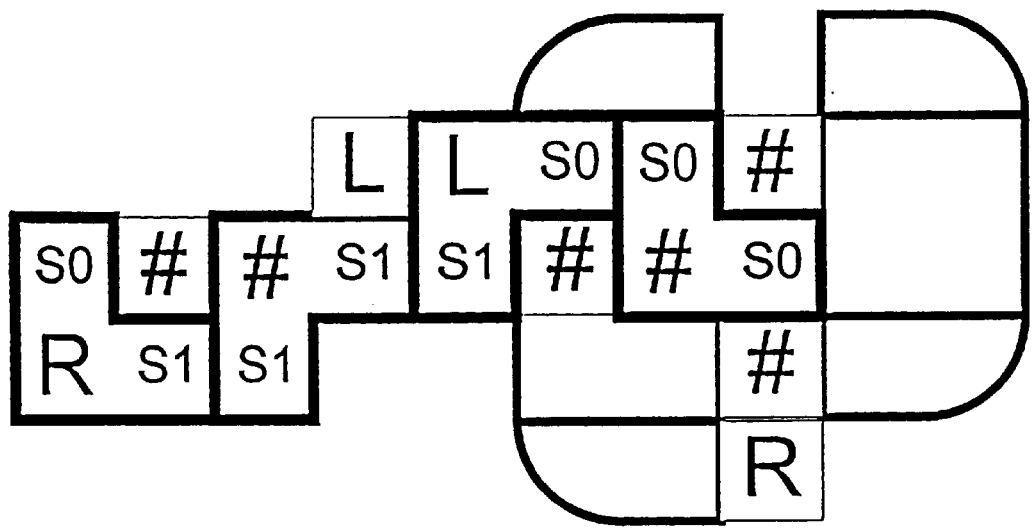
Figure 58:
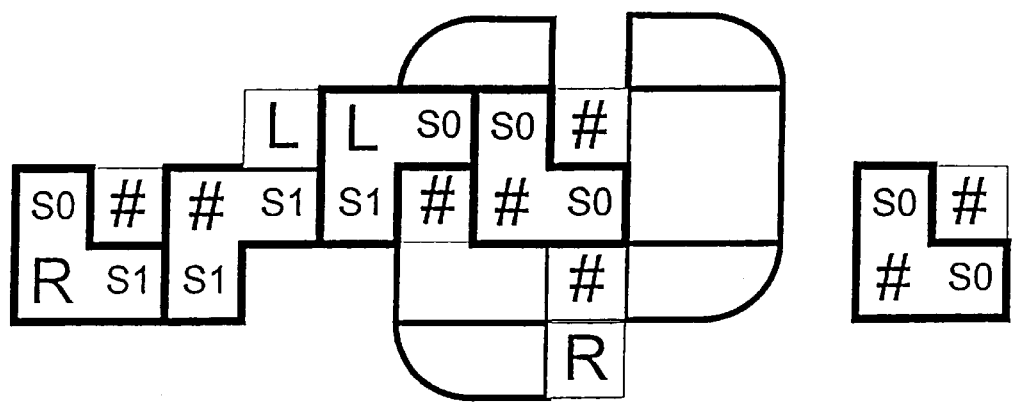
Figure 59:
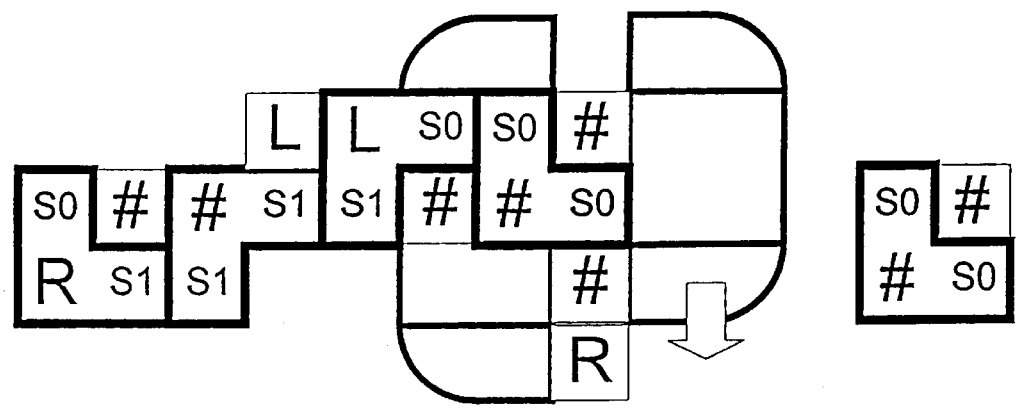

In FIG. 57 the dimer 46 has processed the storage tape 28, displaced the '#' element, replaced it with a '#' element, moved the storage tape 28 read/write head 16 to the right and changed the system state to that of 'S0'. The dimer 46<S0, #, S0, #, right> of FIG. 58 presents itself, however the enzyme 22 is incorrectly formatted to accept it. Through Brownian motion or other means the enzyme 22 of FIG. 59 reconfigures such that the two section enzyme 24 moves relative to the three section enzyme 26 and the storage tape 28.

Figure 60:
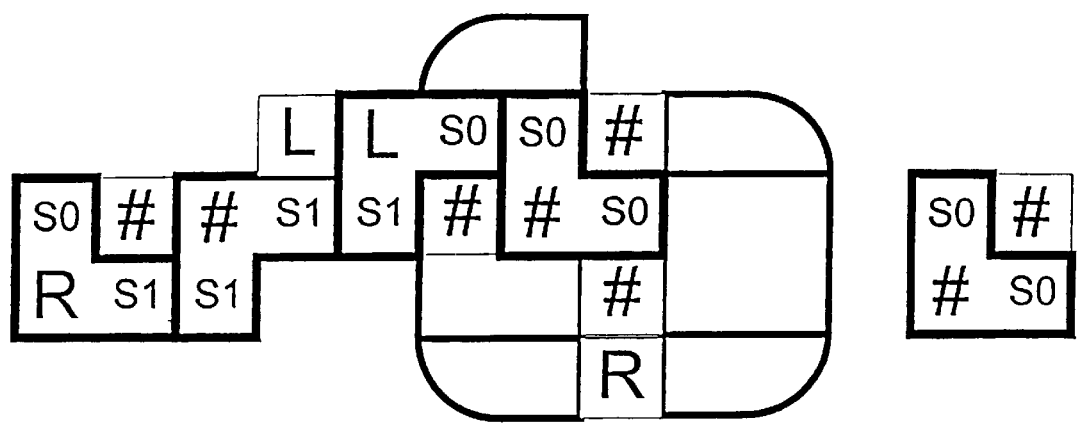
Figure 61:
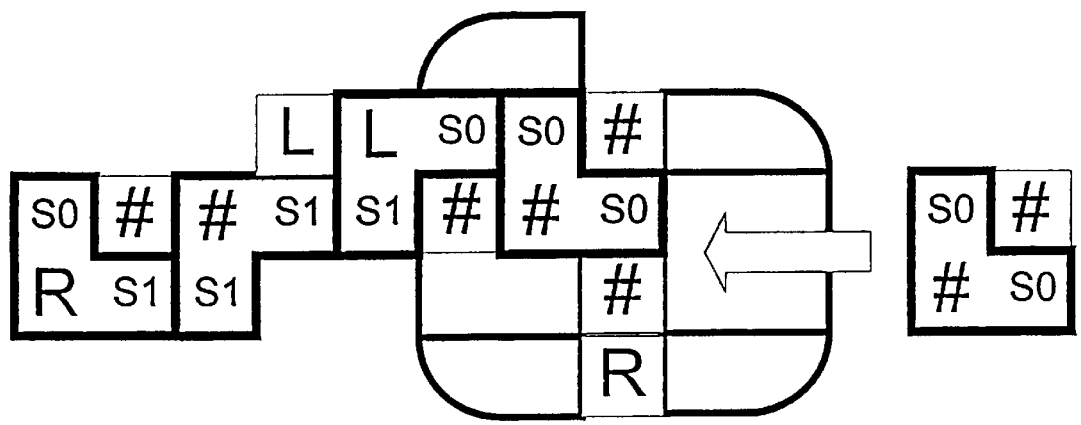
Figure 62:
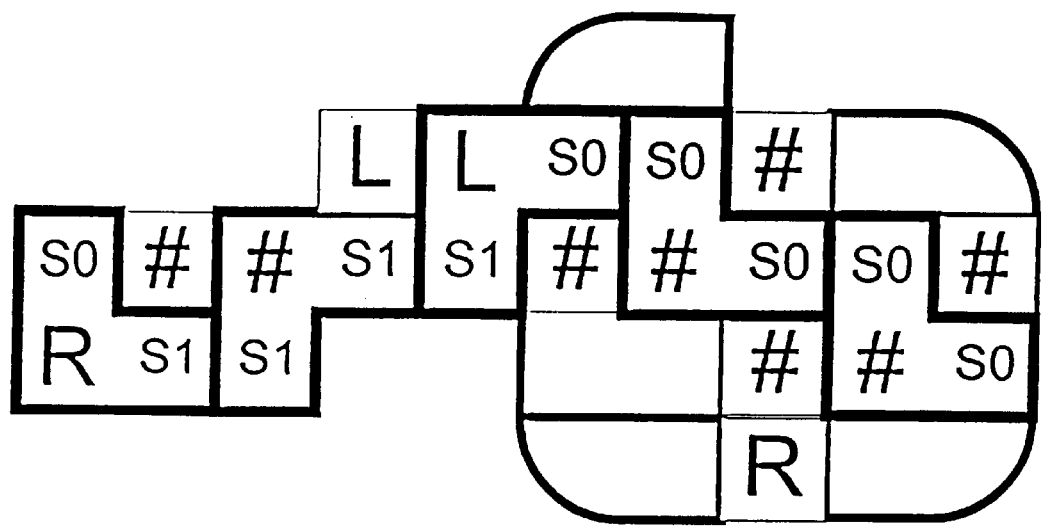

In FIG. 60 the enzyme 22 is now formatted correctly to process the approaching dimer 46. The dimer 46 of FIG. 61 enters the two section enzyme 24. FIG. 62 shows the dimer 46 has successfully meshing with the storage tape 28 having passed all of the enzyme discrimination mechanisms.

Figure 63:
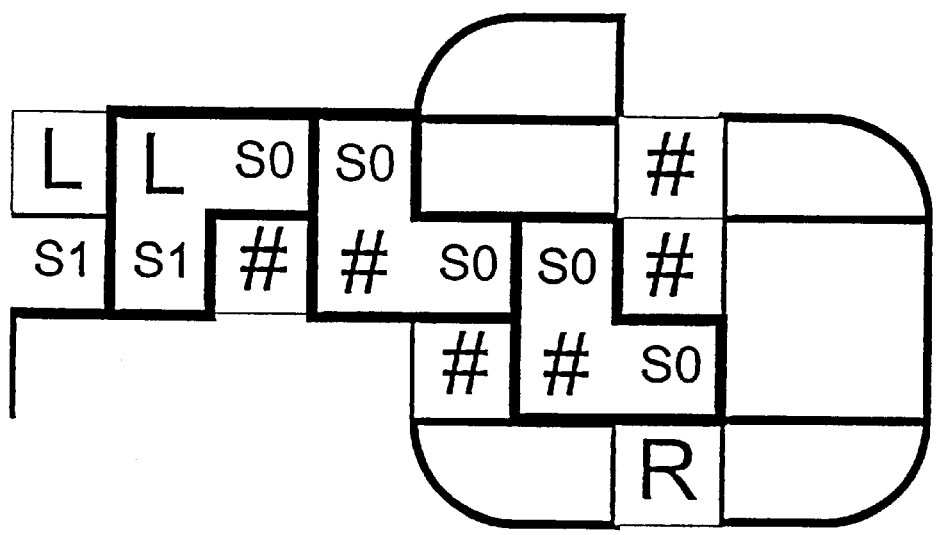
Figure 64:
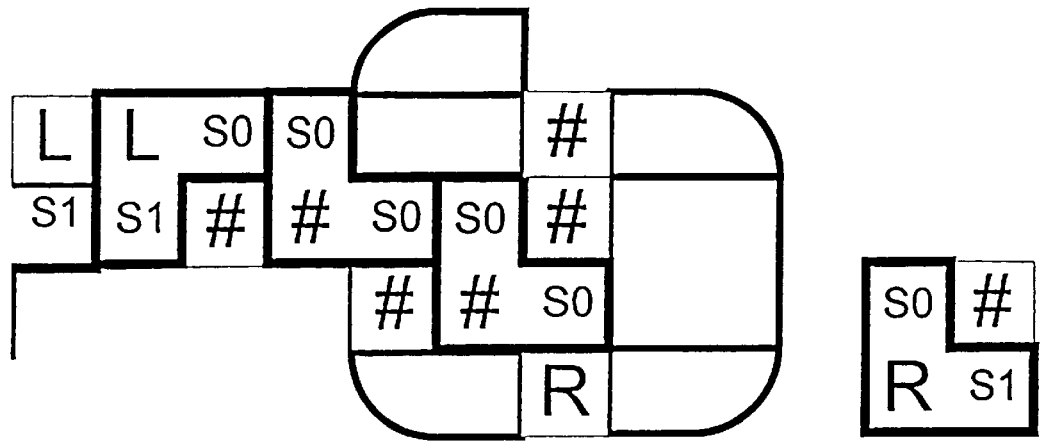

In FIG. 63 the dimer 46 has processed the storage tape 28, has displaced the '#' element, replaced it with a '#' element, moved the storage tape 28 read/write head 16 to the right and changed the system state to that of 'S0'. The dimer 46<S0, R, S1, #, right> of FIG. 64 presents itself, however the enzyme 22 is formatted to accept this.

This case is of special note, the two section enzyme 24 must move down, however it is at the limit of its allowed relative travel to the three section enzyme 26. For processing to occur, the three section enzyme 26 moves first leaving the storage tape 28 and the two section enzyme 24 stationary.

Figure 65:
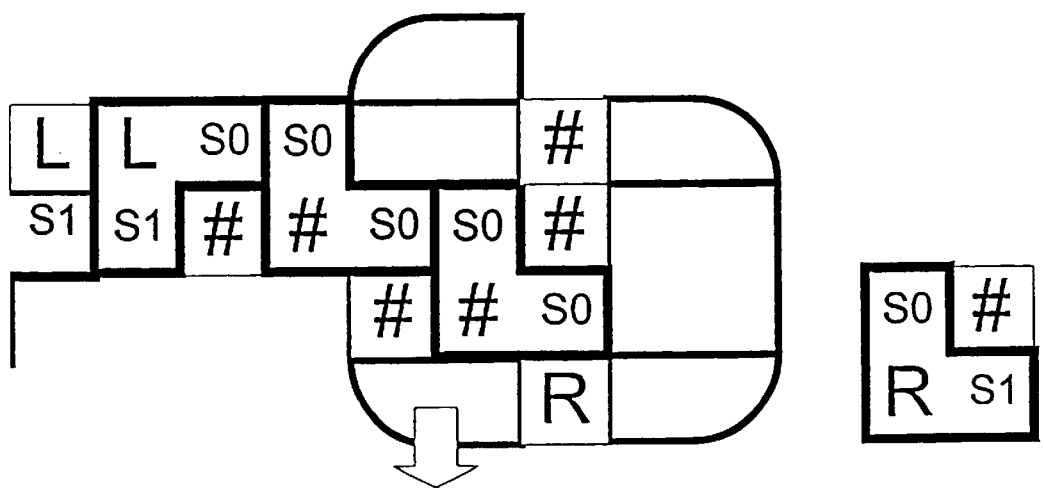
Figure 66:
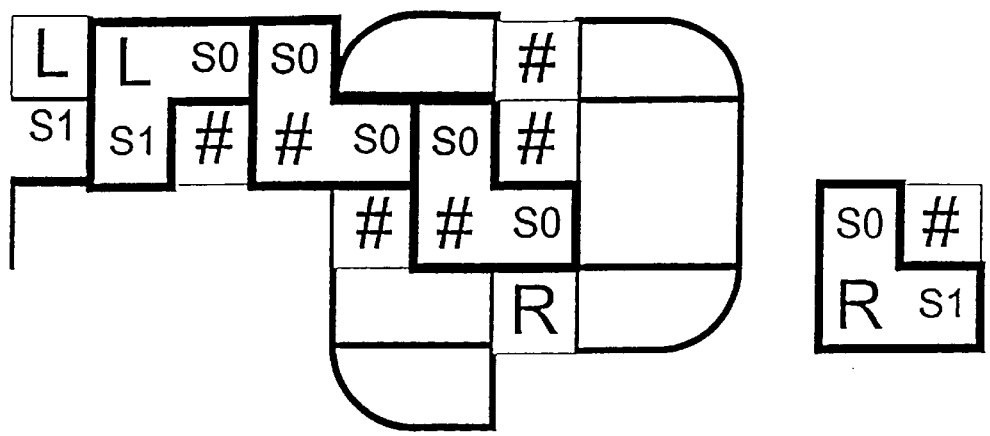
Figure 67:
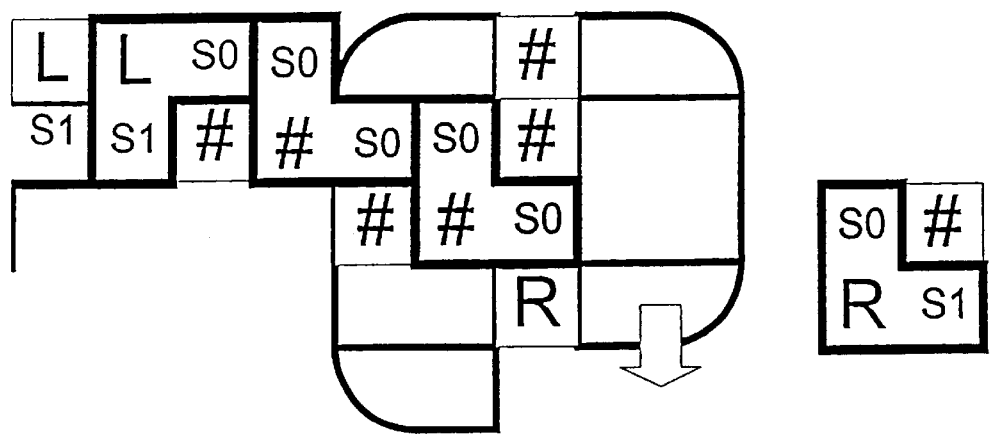

FIG. 65 shows how the three section enzyme 26 moves relative to the storage tape 28 and the two section enzyme 24. In FIG. 66 the three section enzyme 26 has completed its move and in FIG. 67 the two section enzyme 24 moves to facilitate matching of the current approaching dimer 46 and the storage tape 28.

Figure 68:
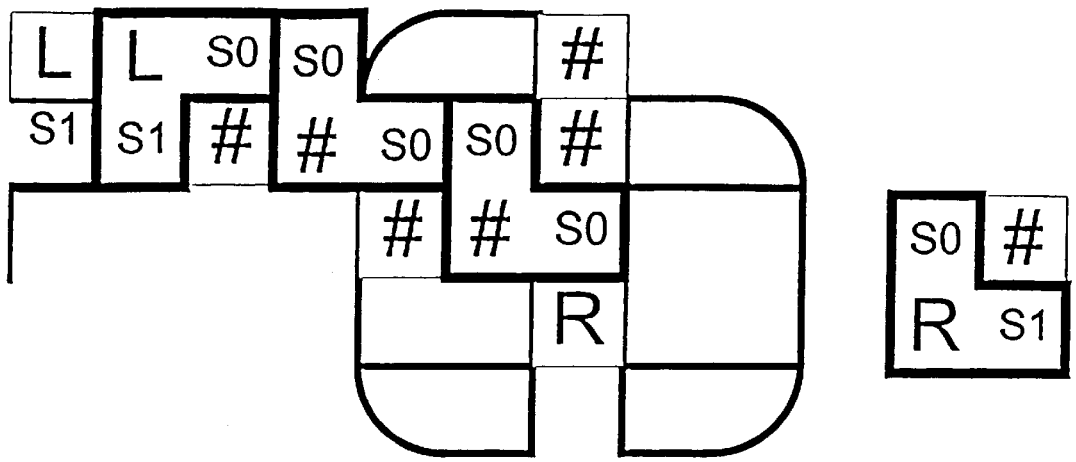

The enzyme 22 in FIG. 68 is correctly formatted to process the approaching dimer 46. It should be noted that in a process not described herein, the enzyme 22 may have reformatted while the dimer 46 was inside the two section enzyme 24. It is additionally noted that essentially at some point the enzyme 22 reformats itself either through sensing the incompatibility of the approaching dimer 46 or through random process.

Furthermore, it is noted that part of this sensing and random process is the compatibility discrimination characteristics of the enzyme 22 itself, where it only processes dimers 46 that are compatible with the storage tape 28 and the current system state.

Figure 69:
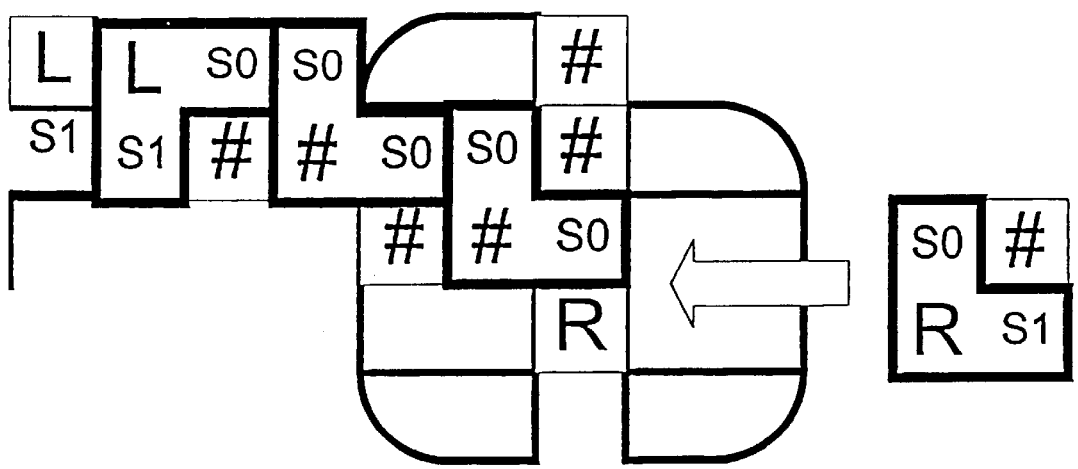
Figure 70:
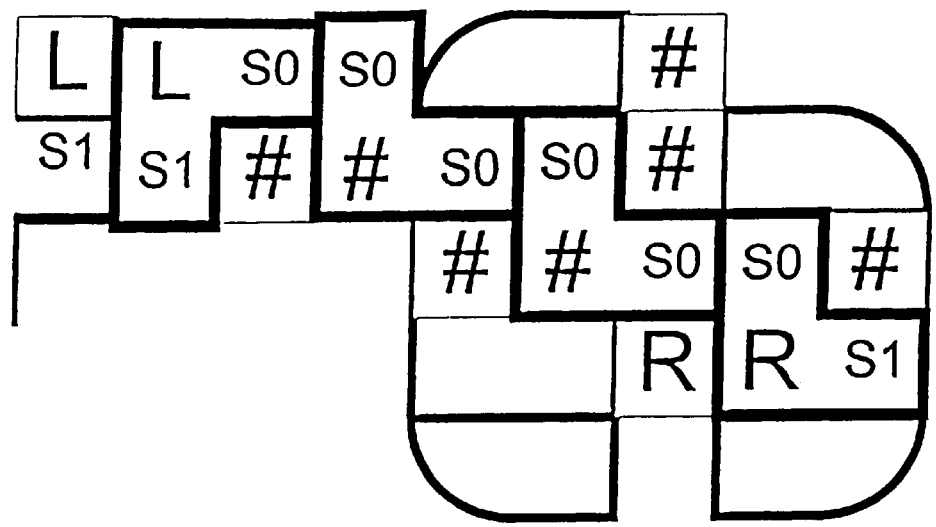
Figure 71:
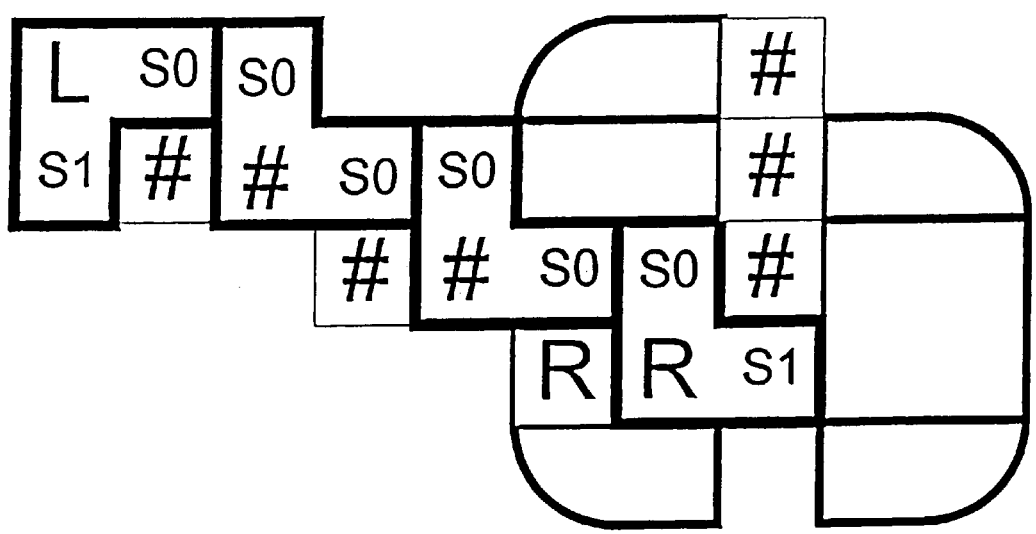

In FIG. 69 the dimer 46 enters the two section enzyme 24. The dimer 46 shown in FIG. 70 has successfully meshed with the storage tape 28, having passed all of the enzyme discrimination mechanisms. The dimer 46 of FIG. 71 has processed the storage tape 28, displaced the 'R' element, replaced it with a '#' element, moved the storage tape 28 read/write head 16 to the right and changed the system state to that of 'S1'.

Figure 72:
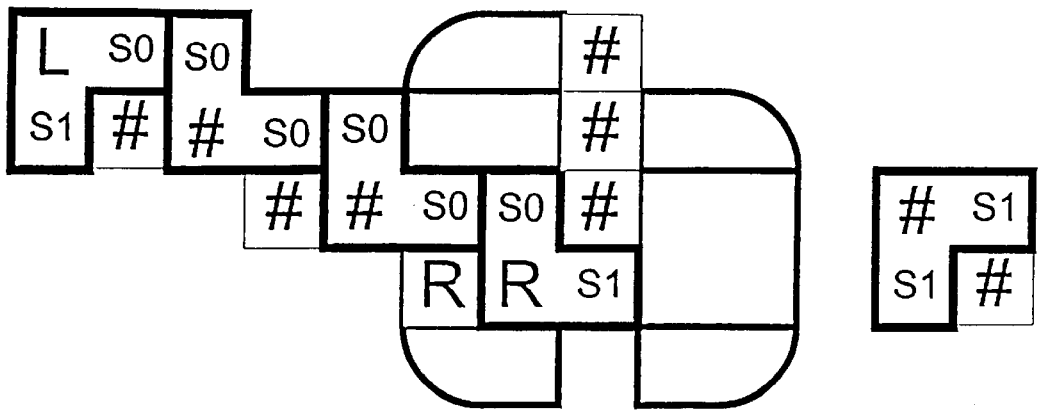
Figure 73:
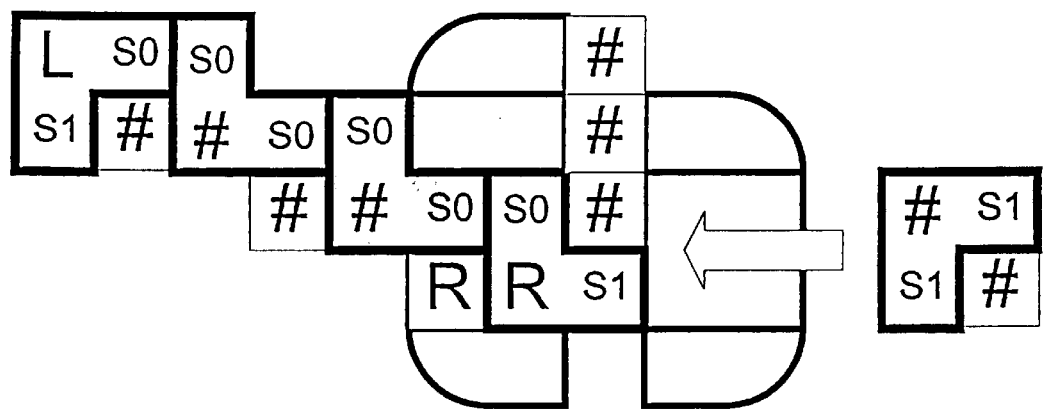
Figure 74:
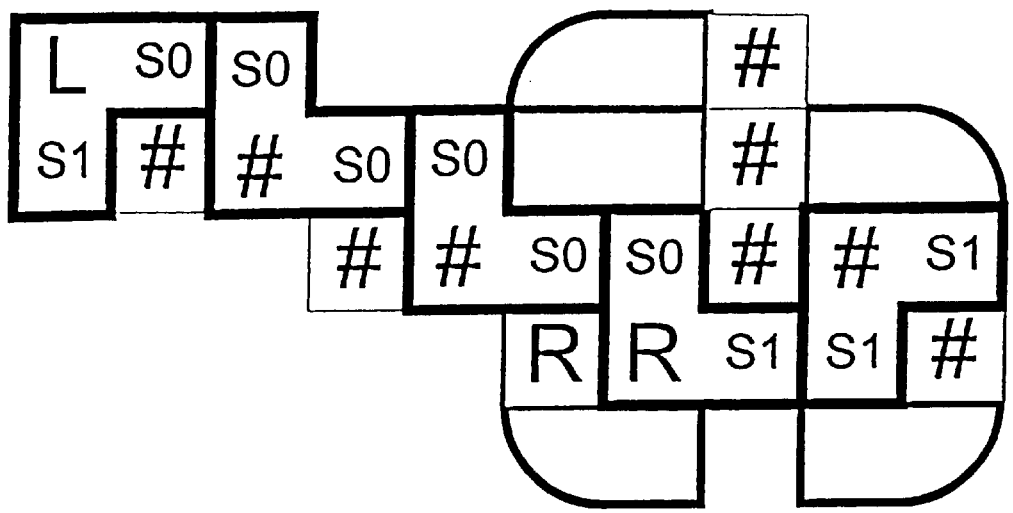

Dimer 46<S1, #, S1, #, left> of FIG. 72 presents itself, and the enzyme 22 is correctly formatted to accept it. In FIG. 73 the dimer 46 enters the two section enzyme 24. The dimer 46 shown in FIG. 74 has successfully meshed with the storage tape 28 having passed all of the enzyme discrimination mechanisms.

Figure 75:
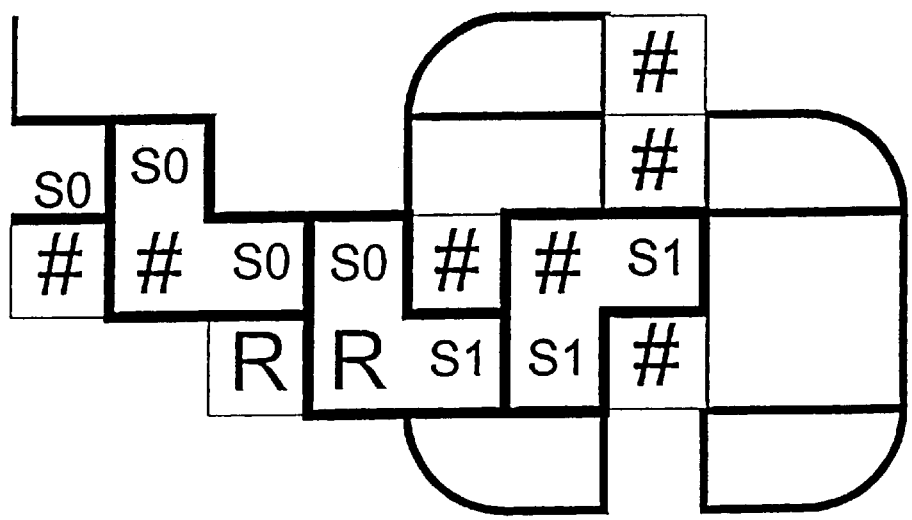
Figure 76:
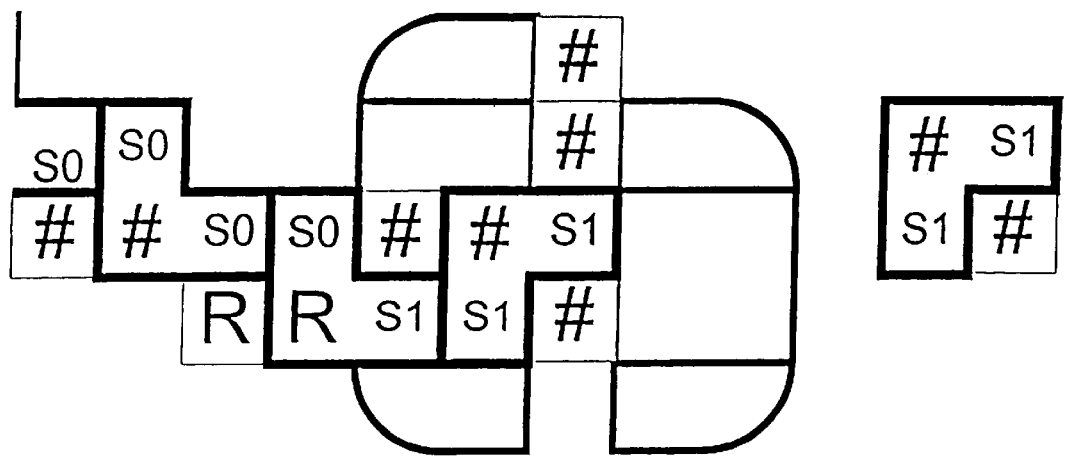

In FIG. 75 the dimer 46 has processed the storage tape 28, displaced the '#' element, replaced it with a '#' element, moved the storage tape 28 read/write head 16 to the left and changed the system state to that of 'S1'. The dimer 46<S1, #, S1, #, left> of FIG. 76 presents itself, however the enzyme 22 is incorrectly formatted to accept it.

Figure 77:
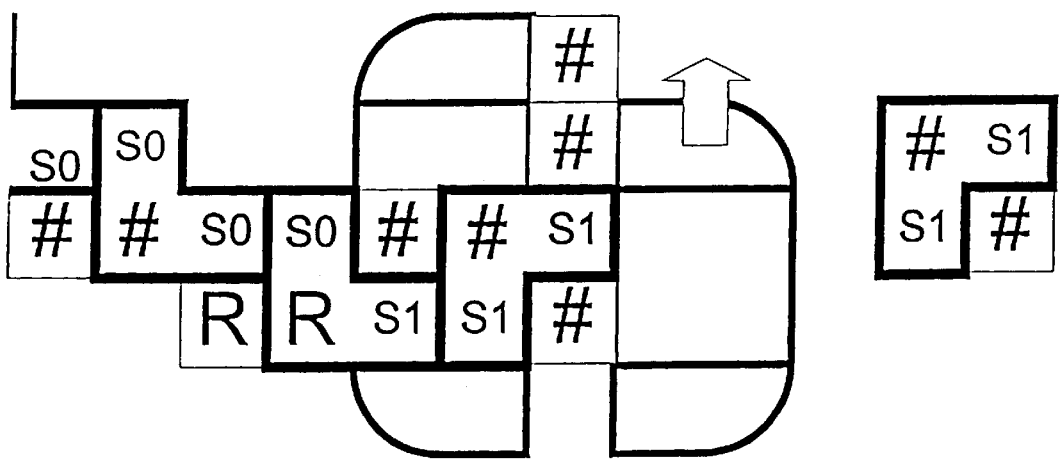
Figure 78:
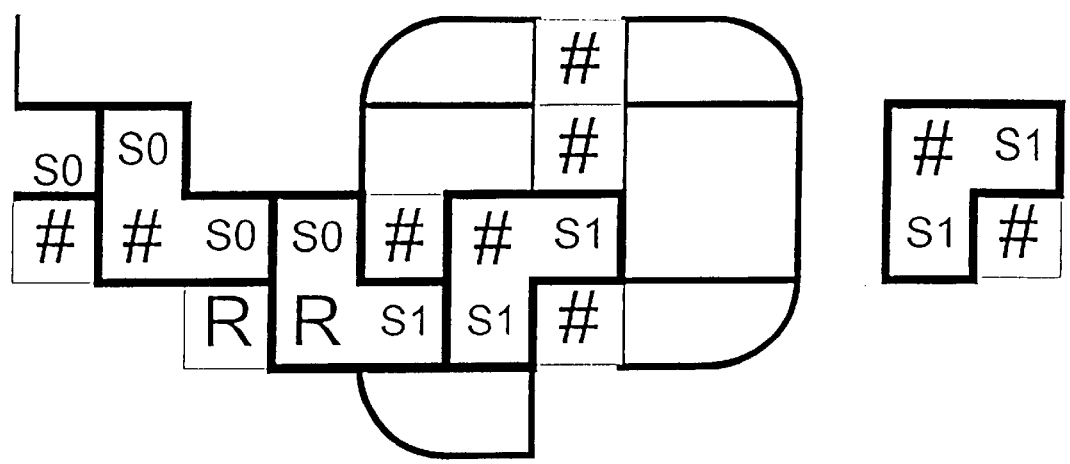
Figure 79:
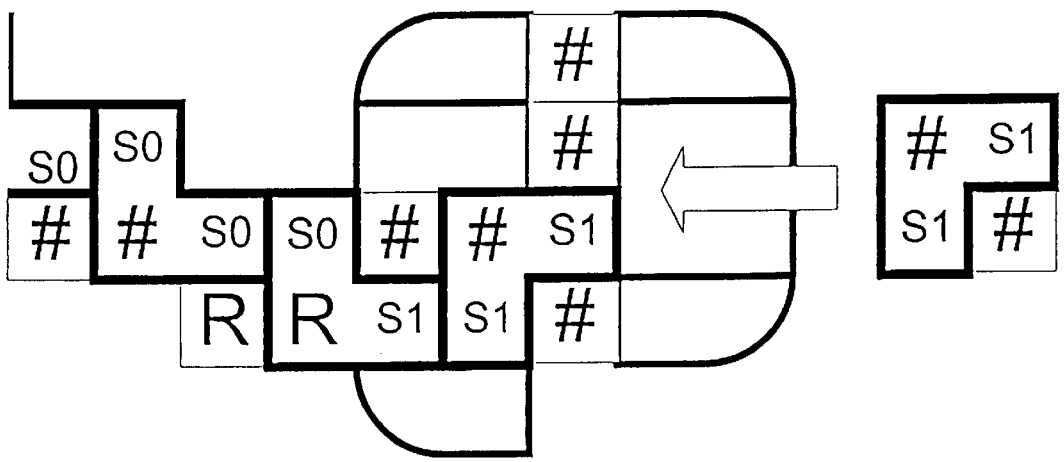
Figure 80:
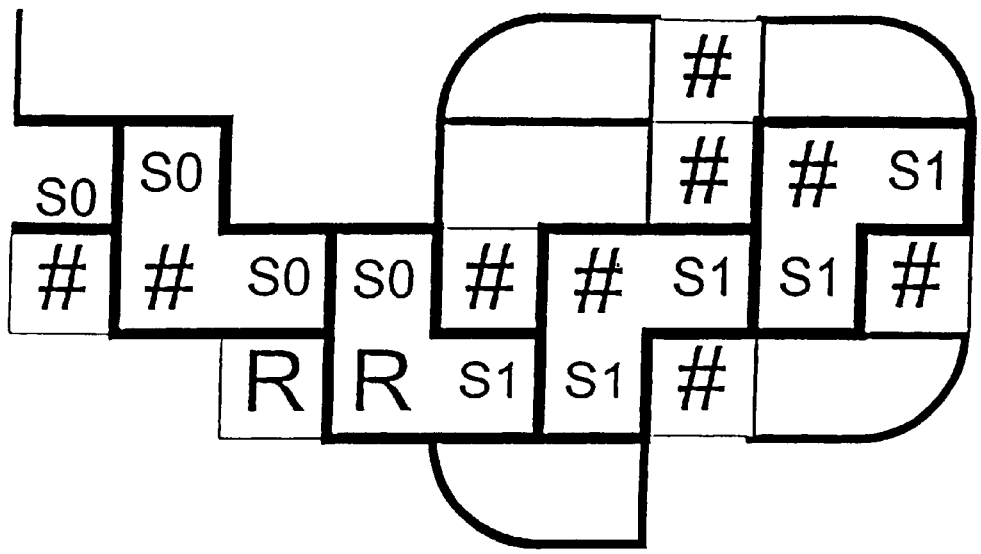

FIG. 77 shows the two section enzyme 24 moving to facilitate the match of the current approaching dimer 46 and the storage tape 28. The enzyme 22 of FIG. 78 is correctly formatted to process the approaching dimer 46. In FIG. 79 the dimer 46 enters the two section enzyme 24. In FIG. 80 the dimer 46 has successfully meshed with the storage tape 28 having passed all of the enzyme discrimination mechanisms.

Figure 81:
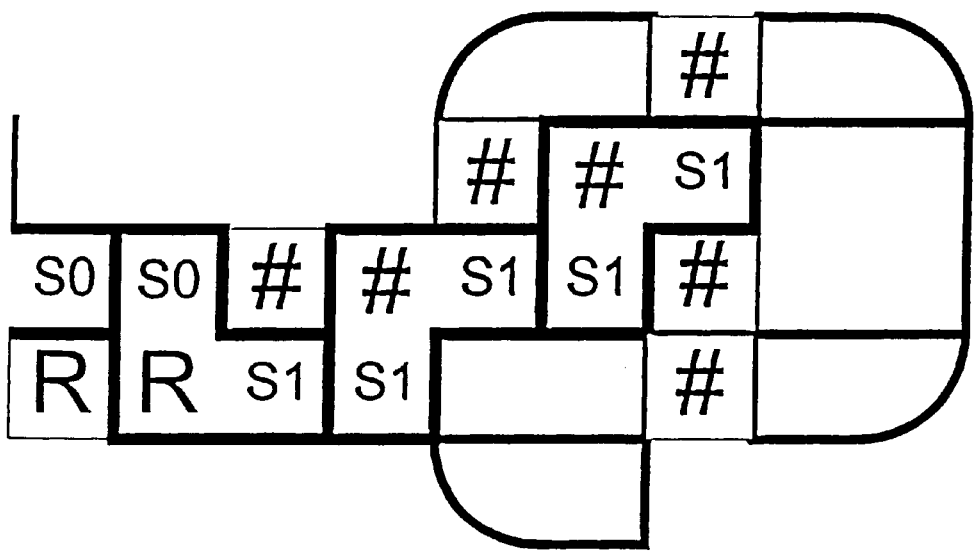

The dimer 46 of FIG. 81 has processed the storage tape 28, displaced the '#' element, replaced it with a '#' element, moved the storage tape 28 read/write head 16 to the left and changed the system state to that of 'S1'.

Figure 82:
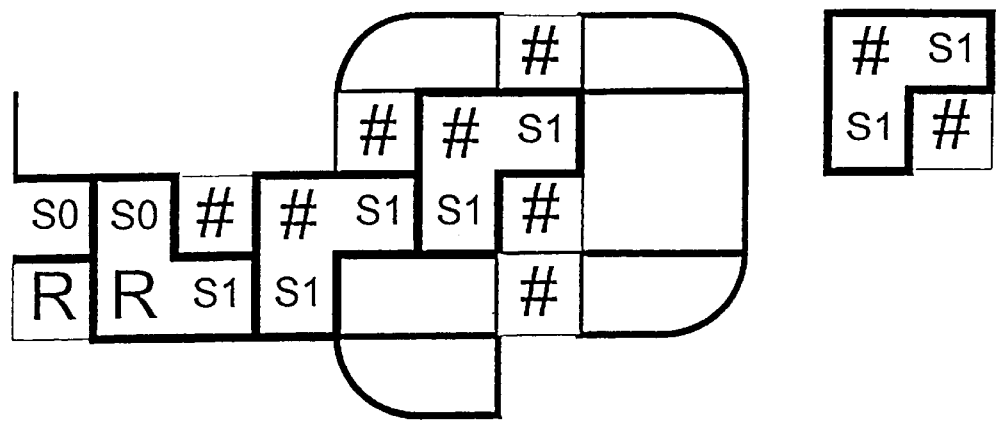

The dimer 46<S1, #, S1, #, left> of FIG. 82 presents itself, however the enzyme 22 is incorrectly formatted to accept it. This case is of special note, the two section enzyme 24 must move down, however it is at the limit of its allowed relative travel to the three section enzyme26. For processing to occur, the three section enzyme 26 moves first leaving the storage tape 28 and the two section enzyme 24 stationary.

Figure 83:
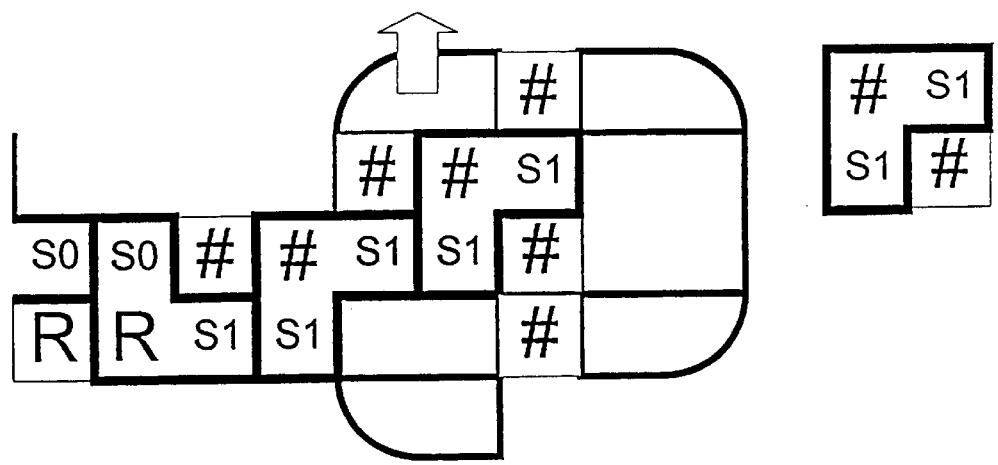
Figure 84:
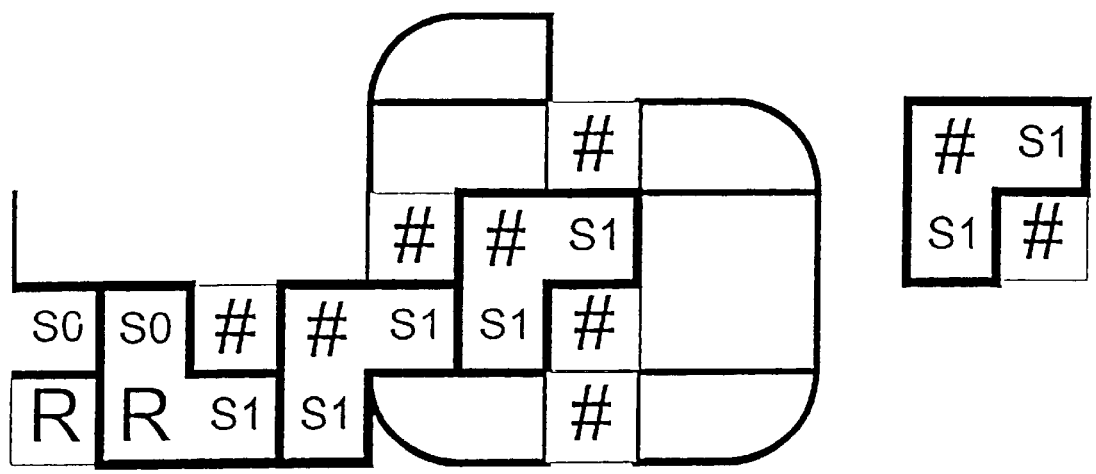
Figure 85:
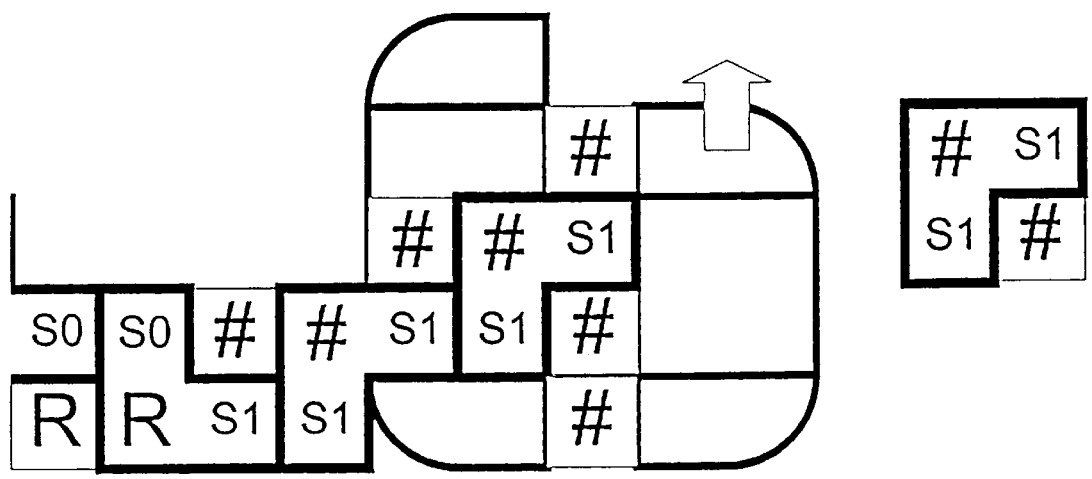

In FIG. 83 the three section enzyme 26 moves relative to the storage tape 28 and the two section enzyme 24. The three section enzyme 26 of FIG. 84 has completed its move. FIG. 85 shows how the two section enzyme 24 moves to facilitate matching of the current approaching dimer 46 and the storage tape 28.

Figure 86:
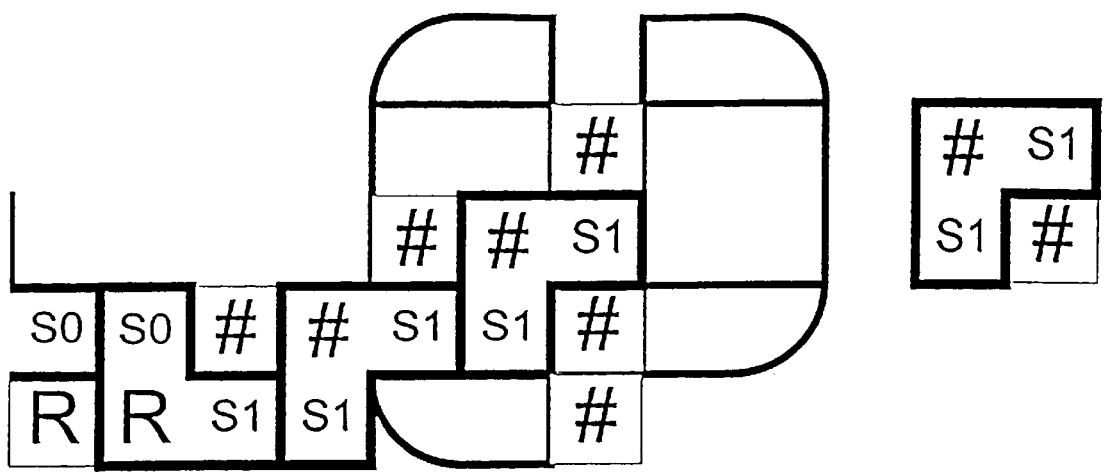

In FIG. 86 the enzyme 22 is correctly formatted to process the approaching dimer 46. It should be noted that although not shown herein the enzyme 22 may have reformatted while the dimer 46 was inside the two section enzyme 24. It is additionally noted that essentially at some point the enzyme 22 reformats itself either through sensing the incompatibility of the approaching dimer 46 or through random process.

Furthermore, note that part of this sensing and random process is the compatibility discrimination characteristics of the enzyme 22 itself, where it only processes dimers 46 that are compatible with the storage tape 28 and the current System State.

Figure 87:
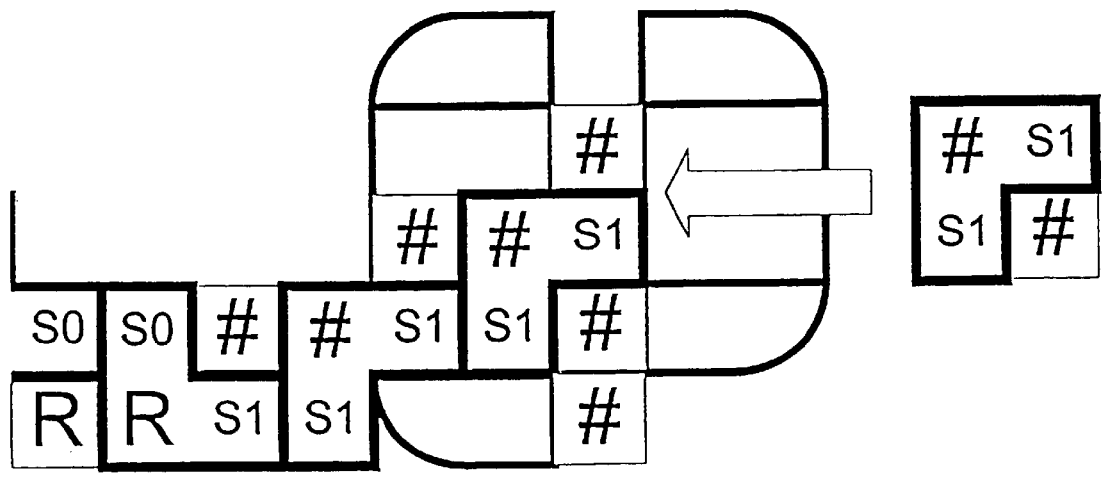
Figure 88:
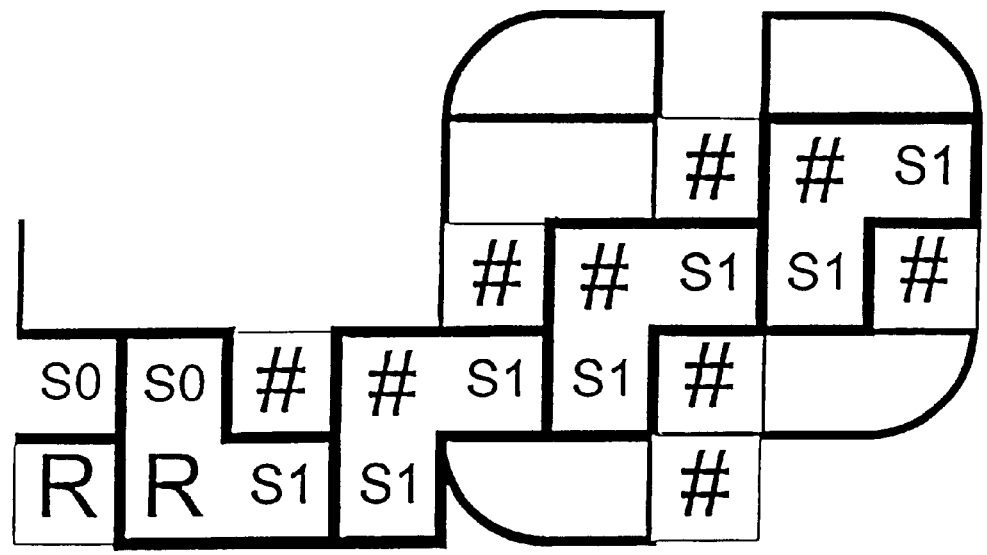

In FIG. 87 the dimer 46 enters the two section enzyme 24. The dimer of FIG. 88 has successfully meshed with the storage tape 28 having passed all of the enzyme discrimination mechanisms. FIG. 89 shows how the dimer 46 has processed the storage tape 28, displaced the '#' element, replaced it with a '#' element, moved the storage tape 28 read/write head 16 to the left and changed the system state to that of 'S1'.

Alternative Embodiment: Molecular Implementation

While we have a completely specified mechanical embodiment, our interest is primarily in a molecular embodiment of the invention, realizing tape monomers, state-transition monomers, and the In and Out parts of the enzyme. It should be apparent to a person skilled in the art that we have optimized the mechanical embodiment to ease its translation into a molecular embodiment. The molecular embodiment incorporates macromolecular structures in place of the mechanical structures described above.

In the context of this invention, a "macromolecule" is considered a polyatomic moiety, such as an oligo- or polynucleotide, an oligo- or polypeptide (including a protein), an oligo- or polysaccharide, or any other polyatomic assembly (for example an organic, inorganic or organometallic species built according to the principles of nanostructure construction. sufficiently large to accommodate the requirements of the device or device subassembly). This is discussed in:

K. E. Drexler. *Proc. Natl. Acad. Sci. USA* 78, No. 9, pp. 5275–5278, 1981.

J. Liu et al. *Science* 280, pp.1253–1256, 1998.

J. M. Michelson et al. *The Fifth Foresight Conference on Molecular Nanotechnology,* Nov. 5–8, 1997; Palo Alto, Calif. [http://www. Zyvex.com/foresight 97/foresight97.htm]

The macromolecule may consist of a linear assembly of monomeric units, where the three dimensional structure is dictated by standard intramolecular interactions (covalent or noncovalent), or a branched structure, e.g., in polysaccharide chemistry.

Any molecular implementation of this device will be readily recognized as such by a person skilled in the art, even if it is (necessarily) different in detail from the mechanical device. For example, it will use intermolecular bonding forces instead of the mechanical concepts (e.g., T slots and T bars) described above.

A complete exposition of the properties of these macromolecules would require enumerating every feature of the mechanical device and restating it as a property of the appropriate macromolecule. For the sake of brevity, we outline here only the key properties of these macromolecules.

Tape monomers are a collection of macromolecules that are different from each other so as to allow discrimination by other macromolecules, yet are similar enough to compose into a polymer. Furthermore, the tape monomers have the ability to bind to each other in order to form arbitrarily long polymers. Examples of such families of monomers as found in normal biological systems include the amino acids, the sugars and the nucleic acids. Binding of tape monomers to each other may be covalent or noncovalent. Covalent binding is preferably reversible under controlled conditions, such as is realizable with polynucleotides, polypeptides or polysaccharides, where one kind of enzyme 22 activity can catalyze polymerization, another kind can catalyze depolymerization at a specific site, or other enzymes which under special circumstances can polymerize or depolymerize.

This is discussed in:

R. E. Offord, in *Protein Design and the Development of New Therapeutics and Vaccines* (J. B. Hook and G. Poste, Eds.), pp. 253–282, Plenum, N.Y., 1990.

H. F. Gaertner et al. *Bioconjugate Chemistry* 5, pp. 333–338, 1994.

Noncovalent binding is for example through metal chelate complex bonding, provided that the state of bonding (on or off) can be precisely controlled. An example would be the use of transition metals (e.g., cobalt) to bridge and link nitrogen- and/or oxygen-rich sections of two monomers. Redox reactions can greatly modify the strength of this bond, for example by controlling the oxidation state of the metal (in this example, Co (II)<->Co(III)).

This is discussed in:

U.S. Pat. No. 5,439,829. L. D. Anderson et al. *"Immobilization of biologically active molecules by changing the oxidation state of a chelated transition metal ion"*. Issued Aug. 8, 1995.

J. E. Hale. *Analytical Biochemistry* 231, pp. 46–49, 1995.

It will be recognized that a tape polymer may be "natural" or "artificial". For example, but not limited to: D-amino acids may be incorporated in place of (or in addition to) L-amino acids, or peptide nucleic acids may be used in place of (or in addition to) naturally occurring nucleic acids.

This is discussed in:

H. Nakajima et al. *Int J Pept Protein Res* 2, pp. 179–85, 1986.

Y. Watanabe et al., *Biochim Biophys Acta* 1337 pp. 40–6, 1997.

P. E. Nielsen et al. *Science* 254, pp. 1497–1500, 1991.

U.S. Pat. No. 5,766,855. O. Buchardt. *"Peptide nucleic acids having enhanced binding affinity and sequence specificity."* Issued Jun. 16, 1998.

They may also include molecular units assembled using nanostructure engineering concepts. Enzymes may be naturally occurring or modified through genetic engineering, or may be synthetic, synthesized either by standard chemical methodology or through nanostructure construction. As such, they may be proteins (classical enzymes) polynucloetides (e.g., ribozymes), nanostructures or they may incorporate a composite of such elements.

It is important to recognize that by controlling microenvironmental conditions, the nature of specificities and catalytic events can be modified. Thus it is feasible, using current combinatorial protein engineering (e.g., phage display) or polynucleotide engineering technology (e.g., SELEX technology), to devise simple recognition and/or catalytic subunits that would operate according to desired specifications under the conditions engineered into the "enzyme" described in this invention.

This is discussed in:

S. F. Parmley and G. P. Smith. *Gene* 73, pp. 305–318, 1988.

P. Soumillion et al. *Appl Biochem Biotechnol* 47, pp. 175–89, 1994.

J. Light and R. A. Lerner. *Bioorg Med Chem.* 7, pp. 955–67, 1995.

U.S. Pat. No. 5,270,163. L. Gold and C. Tuerk. *"Methods for identifying nucleic acid ligands."* Issued Dec. 14, 1993.

Current trends in combinatorial chemistry offer major opportunities for purely synthetic environments to generate structural, binding and catalytic segments of a macromolecule.

State-transition monomers have multiple binding sites. They are able to bind to a tape monomer to form a dimer prior to entering the In tunnel of the enzyme, much the same way as a transfer RNA molecule binds to an amino acid to form a dimer prior to approaching the ribosome. Furthermore, the state-transition monomer has two binding ("recognition") sites on one side, one binding to another state-transition monomer, the other binding to a tape monomer. These bindings are used to discriminate "legal" from "illegal" dimers by the enzyme, as in the mechanical embodiment of the invention. Furthermore, on the opposite side the state-transition monomer has another binding site to a state-transition monomer, which is used in the next transition, as in the mechanical embodiment of the invention.

These binding, or "recognition" reactions are much more easily reversible than those which occur between tape monomers. Sites on complementary surfaces which recognize each other usually involve electrostatic, hydrogen bonding, steric compatibility and van der Waals interactions.

Electrostatic interactions take place between positively and negatively charged surface regions, for example sites rich in the positively charged amino acids lysine and/or arginine or the negatively charged amino acids glutamic acid and/or aspartic acid. One surface with a positive charge will bond with a second surface with a negative charge. Two positive surfaces or two negative surfaces will repel each other.

Hydrogen bonding involves the attraction of a hydrogen atom to small electronegative elements (nitrogen, oxygen, fluorine). Such interactions result in a distortion of charge distribution, which in turn can lead to other cascade events, which might stabilize or destabilize other localized binding reactions.

Steric interactions involve shapes: If one site contains a bulky atom or combination of atoms which cannot fit into a pocket on the other surface, the recognition and binding will not take place. If two surfaces have complementary shapes, that will add to binding forces.

Van der Waals forces (very short range forces) involve attraction between two very close, nonpolar surfaces. In an aqueous environment, nonpolar surfaces do not repel water molecules. Thus when nonpolar surfaces can come together, van der Waals forces permit their interaction and the elimination of water molecules, which contributes to the binding energy. This is called a "hydrophobic" interaction. It can be seen that surface complementarity (steric effects) can have considerable impact on van der Waals interactions.

It will be understood, when discussing component shapes, that the term "side" is used for simplicity, and that shapes of the various parts of the device may vary to accommodate the requirements of the system. It will also be recognized that a macromolecule may vary in shape under different conditions, thus permitting a recognition (binding) site to be displayed only under specific circumstances (for example as a dimer but not as a free monomer).

These recognition, conformation and binding properties of macromolecules are well known in the art.

A change in shape ("conformation") during a binding or state-transition event can be a valuable means of eliminating a "used" component, or of introducing an alternate state. For example, when the dimer formed between a state-transition monomer and a tape monomer completes a state-transition of the tape (for example by substituting its monomer for an existing tape monomer), a conformational change in either the state-transition monomer or the tape monomer might result in removal of the state-transition monomer from the device. Alternatively, it might initiate the display of an alternate state.

The enzyme 22 consists of two macromolecules, each of which may be composed of one or more polymers, composed, for example, of oligonucleotides (RNA, DNA or a modified polymer, such as peptide nucleic acid), polypeptides, or other polymers. The In part and the Out part are loosely coupled not unlike two parts of a ribosome. The In part and the Out part may be two separate macromolecule polymers, or they may be two separate "domains" of the same polymer or polymer complex. Between these two parts there is a tunnel through which the tape polymer is strung, not unlike the way messenger RNA is strung between the two parts of a ribosome. Another tunnel that goes through both the In part and the Out part of the enzyme 22 allows dimers consisting of state-transition monomer and a tape monomer to enter through the In part, and displaced state-transition monomers and tape monomers to leave through the Out part. A discrimination mechanism, which may have some similarities to the discrimination mechanism of the ribosome, prevents "illegal" dimers from entering and displacing the existing state-transition monomer. It will be noted that a molecular implementation of the device may also include additional molecular species, such as cofactors to facilitate recognition or reaction events. It will also be recognized that a "tunnel" may include a literal passage through a section of the enzyme, or it may be represented as a surface "groove" (not necessarily linear) or a partially buried capture and transport system.

One example (but not limited to this example) of a device might include a solution containing one or preferably many "enzyme" macromolecules. In addition, it contains one or preferably many initial state tapes. Finally, there are many transition state monomers and many tape monomers displaying various optional codes ("alphabetic characters"). As examples, the state-transition monomers could be t-RNA (transfer-RNA) molecules or proteins or other polymer equivalents. Each specific state-transition monomer would bind to its complementary tape monomer, for example, as in the case of amino acids, such as serine, threonine, glutamic acid, etc. This recognition and binding reaction could occur through simple Brownian motion in the solution, which could be facilitated through other mechanisms, for example, by heat or ultrasound.

The components of the solution are not limited to these components, but may, depending on the requirements of a particular embodiment, include cofactors, energy providing reagents, buffers to maintain a proper environment, etc.

The "enzyme", which could be free in solution or bound to a solid support, would periodically encounter a tape monomer. The tape monomer would enter the enzyme 22 through the appropriate "tunnel." The size of the tunnel could be controlled by the interactions between different components. For example, a "loose" fit between the In and Out sections of the enzyme 22 might offer a large opening, then after entry of the tape, that opening might be triggered to close, thus presenting the tape for further operation. Alternatively, a surface "groove" may change shape either actively (through controlled—e.g., cofactor induced) or natural—e.g., molecular dynamics—events.

As a dimer formed between a state-transition monomer and a tape monomer approaches an enzyme-tape complex, and encounters its appropriate "tunnel," recognition sites determine whether the two presented tape monomers are appropriate to act upon. Once again, the combination of the dimer with the enzyme 22 might be effected through simple Brownian motion, or it might be facilitated by other forces, such as ultrasound or an electric field.

It will be appreciated that the affinity of the dimer to the enzyme, in as biological system, may be effected by conditions prevailing in the solution, which are relevant to the specific molecules involved in the reaction. Such conditions are ionic strength of the solution, PH etc.

If the two presented tape monomer recognition elements (monomer and state) are not appropriate for action, the dimer is rejected. If they are appropriate, a transition complex is formed between the dimer and the tape segment. A cleavage site, which could be on either the enzyme 22 or on the state-transition monomer, or both, excises the existing monomer and a second, linkage reaction substitutes the new tape monomer.

Options are available at this point. Changes in the nature of the state-transition monomer and/or in the nature of the new tape monomer may result in release of the state-transition monomer, which passes out of the enzyme, as does the replaced tape monomer. The state-transition monomer may then bind to a new copy of its complementary tape monomer and participate in further events.

As a result of the removal of the previous tape monomer, the adjacent (L or R) monomer may be induced to display an activated "state" status (e.g., S0 or S1), or the enzyme 22 itself may display this state (for example, via a conformational change or a cofactor). The combination of the new monomer and the new state information will serve as recognition elements for the next (state-transition-monomer-tape-monomer) dimer.

Alternatively, as a result of excision of the previous tape monomer and insertion of its complementary tape monomer, the state-transition monomer may remain as a connected element of the tape. The next tape monomer would then be required to recognize the state signal provided by this state-transition monomer in order to be recruited for the next operation.

Again, options are available: The "used" state-transition monomer, after the implementation of the next event, may be released, for example via conformational changes, to either waste or to participate in further dimerization events, or it may remain as an element of a new chain produced as a result of the previous events. In the latter case, this new polymer would provide historical information regarding the chain of logical events.

At the end of the reaction, the products may be analyzed by many different means to determine the results of the calculation. Tapes may be read individually with an atomic force microscope, for example, or monomers may be cleaved one by one to sequence the tape, or proteases or restriction enzymes may be used to determine the sequences of tape polymers. These and other options will be recognized by one skilled in the arts, and further options will develop in this rapidly evolving field.

While this example demonstrates various options available to standard solution reactions, it will be recognized by one skilled in the art that the field of nanostructure engineering (see above) is devising micromechanical structures at the molecular level that may operate either in vacuum or in a gaseous environment. Under such conditions, different bonding and reaction mechanisms would apply, and molecular robotics would replace Brownian motion, but the application to this invention is obvious as a result of these teachings.

One limitation to this approach is the potential for error in processing, which is well recognized in normal biological reactions. It is possible that new developments in molecular engineering could overcome the tendency toward errors. For example, the errors are normally a product of the natural dynamics of a recognition/reaction system. Nanoconstruction technologies, using molecular placements and carefully engineered reproduction templates, may eliminate or minimize such errors. There are two alternatives, however, for normal solution reactions.

One option is to provide a validation mechanism. One example of such a mechanism would be to read the sequence of elements of the "history" tape. Any error found during the computation would result either in termination of the computation or in an attempt to correct the calculation. In the latter case, an error would stimulate an alternate calculation, which would correct the resulting tape.

Where the error results in inappropriate recognition between a state-transition monomer and a tape monomer, a validation unit would either dissociate the complex or inactivate it.

A second option would be to carry out a large number of parallel calculations—made feasible by this invention. The resulting population of tapes would then provide a distribution of sequences, where the largest number of identical tapes would represent the true solution, and a minor background population of diverse sequences (lost in the noise) would represent errors.

It will be appreciated by one skilled in the art that there are a great many possible molecular implementations of this invention. In the most obvious implementation, the molecular device may be used to perform complex computations. Additional, and more exciting application of this invention is to couple the computational device to a biological effector mechanism. For example, the presence of a polymer (e.g., a polynucleotide or polypeptide) might initiate the computational sequence, and the end tape monomer product (e.g., a polynucleotide or polypeptide) would carry out a biological action. In the case of a polynucleotide, the end product could be an antisense polymer, which would modify a biological expression activity, and thus a biological activity, a direct coding polymer, which might also impact biological functions, including transcription, replication, or further calculation, or a polypeptide, which would directly carry out a specific function.

Additionally, intermediate steps in a calculation might trigger certain events, for example biological processes and/or actual control of the calculation (for example, through interactions of biochemicals with calculation components, such as the enzyme 22 itself or subassemblies, through additional recognition sites on the components or by interfering with existing recognition reactions. Cascade processes in the biological system might then re-trigger the computational process, which would then lead to the next biological control phase.

Such applications of the invention will be recognized to provide opportunities to link computational events. In other words, the cascade events in one computation may interlink with events in multiple other computational events. Standard biological processes provide examples of such potential, where a perturbation in one metabolic pathway can impact various other metabolic processes.

It will readily be seen that this invention has applications in rational evolution (where the computational processes are encoded directly, via genetic engineering, into genomic material), in genetic engineering applications where a calculation reverses a negative mutation or stimulates a positive mutation, in control of disease processes, either through management of normal biological processes or through incorporation of therapeutic interventions (e.g., through control of pharmaceutical delivery processes), and in ex vivo reactions, such as control of biomanufacturing processes.

It will be appreciated by persons skilled in the art that the present invention is not limited by what has been particularly shown and described herein above.

What is claimed is:

1. A Brownian Turing machine comprising:
   a multiplicity of alphabet elements defining a plurality of different types of information;
   multiple state transition elements defining how said machine can change state;
   a single enzymatic unit for receiving dimers one at a time, wherein each dimer is comprised of one state transition element combined to one alphabet element, for determining if a dimer is an allowable next dimer and, if it is, for connecting the state transition element of the allowed dimer to a history tape of the history of at least one change of state and for modifying an alphabet tape, comprising at least two alphabet elements connected together, with the alphabet element of the allowed dimer in accordance with the state transition defined by the state transition element of the allowed dimer,
   wherein said alphabet elements and said state transition elements are mechanical blocks and said enzymatic unit is formed of mechanical parts.

2. A Turing machine according to claim 1,
   wherein said alphabet element is one unit wide, one unit deep and one unit high,
   wherein said state transition element is two units wide, two units high and one unit deep but a portion of the shape is not present,
   wherein there are left and right state transition elements, each type of which has different portions missing,
   wherein said enzymatic unit has first and second sections and an active site,
   wherein said first section has an incoming dimer tunnel of two units wide and one unit deep,
   wherein said second section has an outgoing dimer tunnel of three units wide and one unit deep,
   wherein the first and second sections meet at said active site and move such that the incoming tunnel is aligned with a first side or a second side of said outgoing tunnel,
   wherein, at said active site, said first and second sections form an alphabet tunnel of one unit high and one unit deep which is perpendicular to said dimer tunnel.

3. A Turing machine according to claim 1 and wherein each said alphabet element is a block comprising:
   a block having three pairs of opposing surfaces, wherein the first and second, third and fourth and fifth and sixth surfaces are paired;
   at least one T-slot on said first surface and at least one T-bar on said second surface which enable said alphabet element to be connected to other alphabet elements in said alphabet tape; and
   a protruding element on said third surface and an indented element on said fourth surface opposite to the third surface, wherein said protruding and indented elements identify the type of said alphabet element.

4. Turing machine according to claim 1 and wherein each said state transition element comprises:
   an L-shaped block having upper, middle and lower surfaces, a first surface perpendicular to said upper surface and between said upper and middle surfaces, a second surface perpendicular to said lower surface and between said lower and middle surfaces, a back surface opposite to said first and second surfaces and two side surfaces;
   at least one T-slot on said lower surface and at least one T-bar on said upper surface which enable said state transition element to be connected to other state transition elements in said history tape;

at least one T-bar on said middle surface which enable said state transition element to be connected to an alphabet element to create said dimer;

a state protruding element on said second surface and a state indented element on said back surface opposite to said second surface, wherein said state protruding and indented elements identify the type of said state transition element; and an protruding element on a third surface and an indented element on said back surface opposite to said third surface, wherein said alphabet protruding and indented elements identify the type of alphabet to be connected to said state transition element.

5. A Turing machine according to claim 4 and wherein each said alphabet element additionally includes means for interlocking pairs of alphabet elements to maintain said alphabet tape.

6. A Turing machine according to claim 1 and wherein said enzymatic unit comprises:

a first portion and a second portion slidably connected together;

an operation area, at the intersection of said first and second portions;

a top passageway, in said first portion, which enables the entry of said dimers to said operation area;

left and right passageways formed to the left and right of said operation area and between said first and second portions which enable the movement of said alphabet tape to the left and right, respectively, of said operation area;

a bottom passageway, in said second portion, which enables the exit of said history tape and of overwritten alphabet monomers from said operation area, wherein said first portion can slide to the left or right of said second portion in accordance with the state transition defined by the state transition element of said allowed dimer.

7. A Turing machine according to claim 6 and wherein each alphabet monomer has a width of one unit and each state transition monomer has a width of two units, the left and right passageways are each one unit deep, the top passageway is two units wide and the bottom passageway is three units wide.

8. A Turing machine according to claim 6 and wherein said enzymatic unit includes discrimination features in said operation area to discriminate against non-matched dimers.

* * * * *